US007691981B2

(12) United States Patent
Gao et al.

(10) Patent No.: US 7,691,981 B2
(45) **Date of Patent: *Apr. 6, 2010**

(54) GROWTH FACTOR HOMOLOG ZVEGF3

(75) Inventors: Zeren Gao, Redmond, WA (US); Charles E. Hart, Woodinville, WA (US); Christopher S. Piddington, Thousand Oaks, CA (US); Paul O. Sheppard, Granite Falls, WA (US); Kimberly E. Shoemaker, Bellevue, WA (US)

(73) Assignee: ZymoGenetics, Inc., Seattle, WA (US)

( * ) Notice: Subject to any disclaimer, the term of this patent is extended or adjusted under 35 U.S.C. 154(b) by 628 days.

This patent is subject to a terminal disclaimer.

(21) Appl. No.: 11/552,378

(22) Filed: Oct. 24, 2006

(65) Prior Publication Data

US 2007/0060507 A1 Mar. 15, 2007

Related U.S. Application Data

(63) Continuation of application No. 11/021,088, filed on Dec. 22, 2004, now Pat. No. 7,387,885, which is a continuation of application No. 09/541,752, filed on Mar. 31, 2000, now Pat. No. 6,887,982, which is a continuation-in-part of application No. 09/457,066, filed on Dec. 7, 1999, now Pat. No. 6,432,673.

(60) Provisional application No. 60/111,173, filed on Dec. 7, 1998, provisional application No. 60/142,576, filed on Jul. 6, 1999, provisional application No. 60/161,653, filed on Oct. 21, 1999, provisional application No. 60/165,255, filed on Nov. 12, 1999.

(51) Int. Cl.
*C12N 15/00* (2006.01)

(52) U.S. Cl. .......................... 530/399; 435/69.5; 435/6; 435/320.1; 435/325; 435/69.1; 530/351

(58) Field of Classification Search ....................... None
See application file for complete search history.

(56) References Cited

U.S. PATENT DOCUMENTS

| | | | | |
|---|---|---|---|---|
| 4,946,778 | A | 8/1990 | Ladner et al. | |
| 6,391,311 | B1 | 5/2002 | Ferrara et al. | |
| 6,432,673 | B1 * | 8/2002 | Gao et al. | 435/69.1 |

FOREIGN PATENT DOCUMENTS

| | | |
|---|---|---|
| WO | 95/14772 | 6/1995 |
| WO | 99/37671 | 7/1999 |
| WO | 99/47677 | 9/1999 |
| WO | 00/04183 | 1/2000 |
| WO | 00/18212 | 4/2000 |
| WO | 00/24774 | 5/2000 |
| WO | 00/32221 | 6/2000 |
| WO | 00/37641 | 6/2000 |
| WO | 00/39284 | 7/2000 |
| WO | 00/53753 | 9/2000 |
| WO | 00/53756 | 9/2000 |
| WO | 00/53758 | 9/2000 |
| WO | 00/53760 | 9/2000 |
| WO | 00/59940 | 10/2000 |
| WO | 00/70050 | 11/2000 |

OTHER PUBLICATIONS

The Institute for Genomic Research, EST 40974, Jul. 3, 1997.
The Institute for Genomic Research, EST W21436, Jul. 3, 1997.
Hillier et al., EST 528192, May 9, 1996.
Adams et al., EST 977627, Apr. 21, 1997.
Marra et al., EST 1759738, Jun. 16, 1998.
Marra et al., EST 2236990, Februay 10, 1999.
National Cancer Institute, Cancer Genome Anatomy Project, EST 2290164, Mar. 3, 1999.
Marra et al., EST 2425258, Apr. 15, 1999.
Ottenwaelder et al., EST 2476351, Apr. 30, 1999.
Duesterhoeft et al., EST 2888195, Jul. 7, 1999.
Ottenwaelder et al, EST 2890217, Jul. 8, 1999.
National Cancer Institute, Cancer Genome Anatomy Project, EST 3182898, Sep. 20, 1999.
Marra et al., EST 3555592, Dec. 3, 1999.
Tsai et al., GenBank Accession No. AF091434, Oct. 1, 1999.
Marra et al., The WashU-HHMI Mouse EST Project, EST 744345, Sep. 23, 1996.
LIFESEQ™ Information Results, Incyte Pharmaceuticals, Inc., INC1302516, May 1999.
LIFESEQ™ Information Results, Incyte Pharmaceuticals, Inc., INC1303909, May 1999.
LIFESEQ™ Information Results, Incyte Pharmaceuticals, Inc., INC2453444, May 1999.
LIFESEQ™ Information Results, Incyte Pharmaceuticals, Inc., INC2451669, May 1999.
LIFESEQ™ Information Results, Incyte Pharmaceuticals, Inc., INC3440025, Jul. 8, 1997.
LIFESEQ™ Information Results, Incyte Pharmaceuticals, Inc., INC2547850, Feb. 4, 1997.
LIFESEQ™ Information Results, Incyte Pharmaceuticals, Inc., INC2962366, Sep. 8, 1997.
LIFESEQ™ Information Results, Incyte Pharmaceuticals, Inc., INC3598059, Sep. 8, 1997.
LIFESEQ™ Information Results, Incyte Pharmaceuticals, Inc., INC3073703, Mar. 12, 1998.
LIFESEQ™ Information Results, Incyte Pharmaceuticals, Inc., INC4825396, Jul. 9, 1998.

(Continued)

*Primary Examiner*—Lorraine Spector
(74) *Attorney, Agent, or Firm*—Nicholas V. Sherbina; Gary E. Parker

(57) ABSTRACT

Polypeptide growth factors, methods of making them, polynucleotides encoding them, antibodies to them, and methods of using them are disclosed. The polypeptides comprise an amino acid segment that is at least 90% identical to residues 46-163 of SEQ ID NO:2 or residues 235-345 of SEQ ID NO:2. Multimers of the polypeptides are also disclosed. The polypeptides, multimeric proteins, and polynucleotides can be used in the study and regulation of cell and tissue development, as components of cell culture media, and as diagnostic agents.

8 Claims, 12 Drawing Sheets

OTHER PUBLICATIONS

LIFESEQ™ Information Results, Incyte Pharmaceuticals, Inc., INC5832763, Feb. 20, 1999.

Li et al "PDGF-C is a new protease-activated ligand for the PDGF α-receptor," *Nature Cell Biol. 2*:302-309, 2000.

* cited by examiner

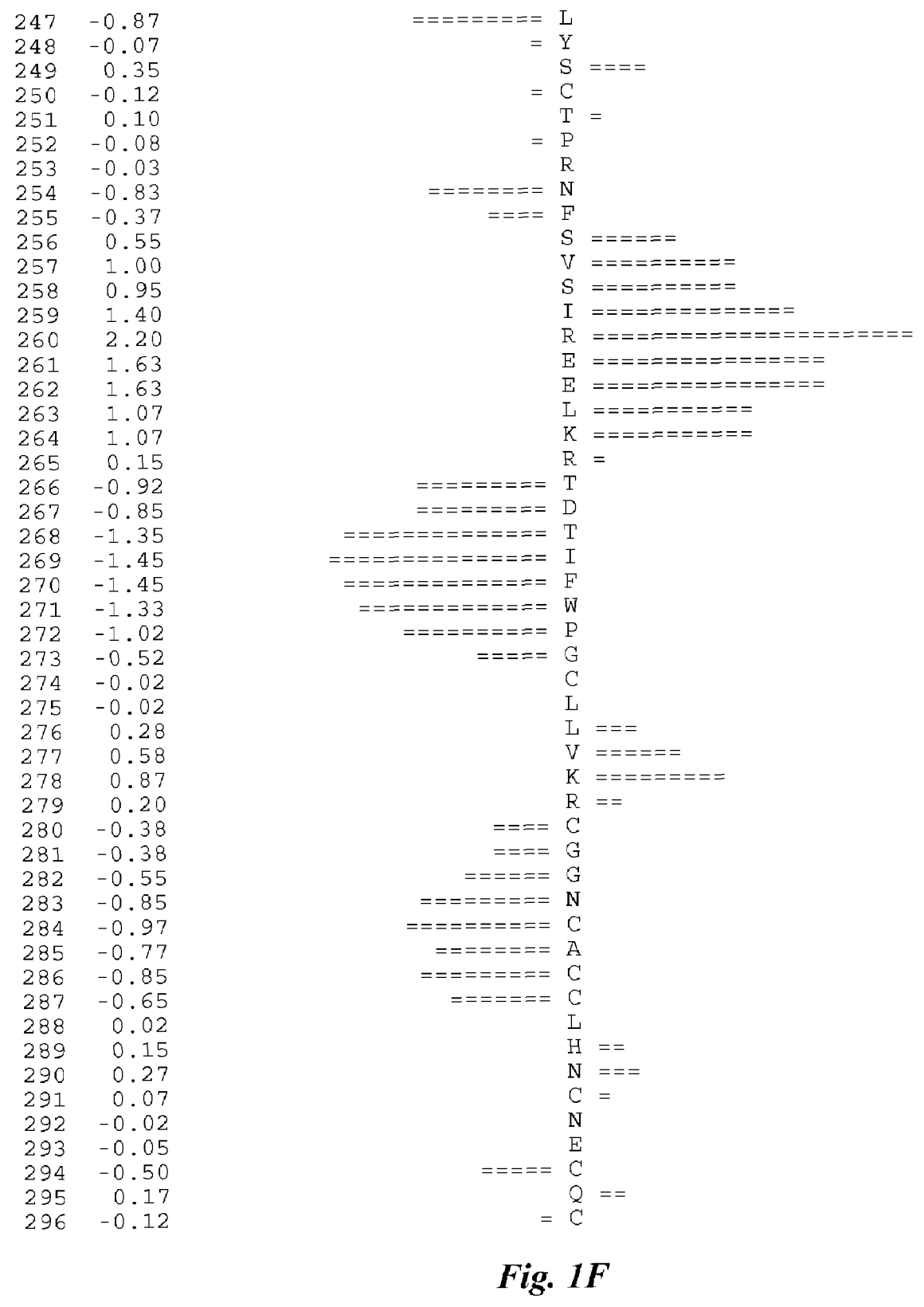

| Position | Value | Residue |
|---|---|---|
| 247 | -0.87 | L |
| 248 | -0.07 | Y |
| 249 | 0.35 | S |
| 250 | -0.12 | C |
| 251 | 0.10 | T |
| 252 | -0.08 | P |
| 253 | -0.03 | R |
| 254 | -0.83 | N |
| 255 | -0.37 | F |
| 256 | 0.55 | S |
| 257 | 1.00 | V |
| 258 | 0.95 | S |
| 259 | 1.40 | I |
| 260 | 2.20 | R |
| 261 | 1.63 | E |
| 262 | 1.63 | E |
| 263 | 1.07 | L |
| 264 | 1.07 | K |
| 265 | 0.15 | R |
| 266 | -0.92 | T |
| 267 | -0.85 | D |
| 268 | -1.35 | T |
| 269 | -1.45 | I |
| 270 | -1.45 | F |
| 271 | -1.33 | W |
| 272 | -1.02 | P |
| 273 | -0.52 | G |
| 274 | -0.02 | C |
| 275 | -0.02 | L |
| 276 | 0.28 | L |
| 277 | 0.58 | V |
| 278 | 0.87 | K |
| 279 | 0.20 | R |
| 280 | -0.38 | C |
| 281 | -0.38 | G |
| 282 | -0.55 | G |
| 283 | -0.85 | N |
| 284 | -0.97 | C |
| 285 | -0.77 | A |
| 286 | -0.85 | C |
| 287 | -0.65 | C |
| 288 | 0.02 | L |
| 289 | 0.15 | H |
| 290 | 0.27 | N |
| 291 | 0.07 | C |
| 292 | -0.02 | N |
| 293 | -0.05 | E |
| 294 | -0.50 | C |
| 295 | 0.17 | Q |
| 296 | -0.12 | C |

*Fig. 1F*

```
MSLFGLLLLTSALAGQRQGTQAESNLSSKFQFSSNKEQNGVQDPQHERIITVSTNGSIHS

MLLLGLLLLTSALAGQRTGTRAESNLSSKLQLSSDKEQNGVQDPRHERVVTISGNGSIHS
        10        20        30        40        50        60

PRFPHTYPRNTVLVWRLVAVEENVWIQLTFDERFGLEDPEDDICKYDFVEVEEPSDGTIL

PKFPHTYPRNMVLVWRLVAVDENVRIQLTFDERFGLEDPEDDICKYDFVEVEEPSDGSVL
        70        80        90       100       110       120

GRWCGSGTVPGKQISKGNQIRIRFVSDEYFPSEPGFCIHYNIVMPQFTEAVSPSVLPPSA

GRWCGSGTVPGKQTSKGNHIRIRFVSDEYFPSEPGFCIHYSIIMPQVTETTSPSVLPPSS
       130       140       150       160       170       180

LPLDLLNNAITAFSTLEDLIRYLEPERWQLDLEDLYRPTWQLLGKAFVFGRKSRVVDLNL

LSLDLLNNAVTAFSTLEELIRYLEPDRWQVDLDSLYKPTWQLLGKAFLYGKKSKVVNLNL
       190       200       210       220       230       240

LTEEVRLYSCTPRNFSVSIREELKRTDTIFWPGCLLVKRCGGNCACCLHNCNECQCVPSK

LKEEVKLYSCTPRNFSVSIREELKRTDTIFWPGCLLVKRCGGNCACCLHNCNECQCVPRK
       250       260       270       280       290       300

VTKKYHEVLQLRPKTGVRGLHKSLTDVALEHHEECDCVCRGSTGG (SEQ ID NO:2)

VTKKYHEVLQLRPKTGVKGLHKSLTDVALEHHEECDCVCRGNAGG (SEQ ID NO:43)
       310       320       330       340
```

*Fig. 6*

GROWTH FACTOR HOMOLOG ZVEGF3

CROSS-REFERENCE TO RELATED APPLICATIONS

This application is a continuation of U.S. application Ser. No. 11/021,088, filed Dec. 22, 2004, now U.S. Pat. No. 7,387,885, which is a continuation of U.S. application Ser. No. 09/541,752, filed Mar. 31, 2000, now U.S. Pat. No. 6,887,982, which is a continuation-in-part of U.S. application Ser. No. 09/457,066, filed Dec. 7, 1999, now U.S. Pat. No. 6,432,673, which claims the benefit of U.S. Provisional Applications Ser. No. 60/111,173, filed Dec. 7, 1998, Ser. No. 60/142,576, filed Jul. 6, 1999, Ser. No. 60/161,653, filed Oct. 21, 1999, and Ser. No. 60/165,255, filed Nov. 12, 1999, all of which are herein incorporated by reference.

BACKGROUND OF THE INVENTION

In multicellular animals, cell growth, differentiation, and migration are controlled by polypeptide growth factors. These growth factors play a role in both normal development and pathogenesis, including the development of solid tumors.

Polypeptide growth factors influence cellular events by binding to cell-surface receptors, many of which are tyrosine kinases. Binding initiates a chain of signalling events within the cell, which ultimately results in phenotypic changes, such as cell division, protease production, and cell migration.

Growth factors can be classified into families on the basis of structural similarities. One such family, the PDGF (platelet derived growth factor) family, is characterized by a dimeric structure stabilized by disulfide bonds. This family includes PDGF, the placental growth factors (PlGFs), and the vascular endothelial growth factors (VEGFs). The individual polypeptide chains of these proteins form characteristic higher-order structures having a bow tie-like configuration about a cystine knot, formed by disulfide bonding between pairs of cysteine residues. Hydrophobic interactions between loops contribute to the dimerization of the two monomers. See, Daopin et al., *Science* 257:369, 1992; Lapthom et al., *Nature* 369:455, 1994. Members of this family are active as both homodimers and heterodimers. See, for example, Heldin et al., *EMBO J.* 7:1387-1393, 1988; Cao et al., *J. Biol. Chem.* 271:3154-3162, 1996. The cystine knot motif and bow tie fold are also characteristic of the growth factors transforming growth factor-beta (TGF-β) and nerve growth factor (NGF), and the glycoprotein hormones. Although their amino acid sequences are quite divergent, these proteins all contain the six conserved cysteine residues of the cystine knot.

Four vascular endothelial growth factors have been identified: VEGF, also known as vascular permeability factor (Dvorak et al., *Am. J. Pathol.* 146:1029-1039, 1995); VEGF-B (Olofsson et al., *Proc. Natl. Acad. Sci. USA* 93:2567-2581, 1996; Hayward et al., WIPO Publication WO 96/27007); VEGF-C (Joukov et al., *EMBO J.* 15:290-298, 1996); and VEGF-D (Oliviero, WO 97/12972; Achen et al., WO 98/07832). Five VEGF polypeptides (121, 145, 165, 189, and 206 amino acids) arise from alternative splicing of the VEGF mRNA.

VEGFs stimulate the development of vasculature through a process known as angiogenesis, wherein vascular endothelial cells re-enter the cell cycle, degrade underlying basement membrane, and migrate to form new capillary sprouts. These cells then differentiate, and mature vessels are formed. This process of growth and differentiation is regulated by a balance of pro-angiogenic and anti-angiogenic factors. Angiogenesis is central to normal formation and repair of tissue, occurring in embryo development and wound healing. Angiogenesis is also a factor in the development of certain diseases, including solid tumors, rheumatoid arthritis, diabetic retinopathy, macular degeneration, and atherosclerosis.

A number of proteins from vertebrates and invertebrates have been identified as influencing neural development. Among those molecules are members of the neuropilin family and the semaphorin/collapsin family. Neuronal cell outgrowths, known as processes, grow away from the cell body to form synaptic connections. Long, thin processes that carry information away from the cell body are called axons, and short, thicker processes which carry information to and from the cell body are called dendrites. Axons and dendrites are collectively referred to as neurites. Neurites are extended by means of growth cones, the growing tips of neurites, which are highly motile and are ultimately responsible for increasing and extending the neuronal network in the body.

Three receptors for VEGF have been identified: KDR/Flk-1 (Matthews et al., *Proc. Natl. Acad. Sci. USA* 88:9026-9030, 1991), Flt-1 (de Vries et al., *Science* 255:989-991, 1992), and neuropilin-1 (Soker et al., *Cell* 92:735-745, 1998). Neuropilin-1 is a cell-surface glycoprotein that was initially identified in *Xenopus* tadpole nervous tissues, then in chicken, mouse, and human. The primary structure of neuropilin-1 is highly conserved among these vertebrate species. Neuropilin-1 has been demonstrated to be a receptor for various members of the semaphorin family including semaphorin III (Kolodkin et al., *Cell* 90:753-762, 1997), Sema E and Sema IV (Chen et al., *Neuron* 19:547-559, 1997). A variety of activities have been associated with the binding of neuropilin-1 to its ligands. For example, binding of semaphorin III to neuropilin-1 can induce neuronal growth cone collapse and repulsion of neurites in vitro (Kitsukawa et al., *Neuron* 19: 995-1005, 1997).

In mice, neuropilin-1 is expressed in the cardiovascular system, nervous system, and limbs at particular developmental stages. Chimeric mice over-expressing neuropilin-1 were found to be embryonic lethal (Kitsukawa et al., *Development* 121:4309-4318, 1995). The chimeric embryos exhibited several morphological abnormalities, including excess capillaries and blood vessels, dilation of blood vessels, malformed hearts, ectopic sprouting and defasciculation of nerve fibers, and extra digits. All of these abnormalities occurred in the organs in which neuropilin-1 is expressed in normal development. Mice lacking the neuropilin-1 gene have severe cardiovascular abnormalities, including impairment of vascular network formation in the central and peripheral nervous systems (Takashima et al., American Heart Association 1998 Meeting, Abstract # 3178).

Neuropilin-1 has been identified as a cell-surface receptor for VEGF (Soker et al., ibid.), and displays selective binding activity for $VEGF_{165}$ over $VEGF_{121}$. It has been shown to be expressed on vascular endothelial cells and tumor cells in vitro. When neuropilin-1 is co-expressed in cells with KDR, neuropilin-1 enhances the binding of $VEGF_{165}$ to KDR and $VEGF_{165}$-mediated chemotaxis. Conversely, inhibition of $VEGF_{165}$ binding to neuropilin-1 inhibits its binding to KDR and its mitogenic activity for endothelial cells (Soker, et al., ibid.). Neuropilin-1 is also a receptor for PlGF-2 (Migdal et al., *J. Biol. Chem.* 273: 22272-22278, 1998). A second semaphorin receptor, neuropilin-2, exhibits homology with neuropilin-1 but has differs in binding specificity (Chen et al. *Neuron* 19: 547-559, 1997).

Semaphorins are a large family of molecules which share the defining semaphorin domain of approximately 500 amino acids. This family can be subdivided into multiple subfamilies that contain both secreted and membrane-bound proteins.

Select members of these subfamilies, class III (SemD) and class IV (SemD), form homodimers linked by disulfide bridges. In the case of SemD, there is additional proteolytic processing that creates a 65-kDa isoform that lacks the 33-kDa carboxyl-terminal sequence. Dimerization is believed to be important for functional activity (Klostermann et al., *J. Biol. Chem.* 273:7326-7331, 1998). Collapsin-1, the first identified vertebrate member of the semaphorin family of axon guidance proteins, has also been shown to form covalent dimers, with dimerization necessary for collapse activity (Koppel et al., *J. Biol. Chem.* 273:15708-15713, 1998).

Semaphorin III has been associated in vitro with regulating growth clone collapse and chemorepulsion of neurites. In vivo it has also been shown to be required for correct sensory afferent innervation and other aspects of development, including skeletal and cardiac defects (Fehar et al., Nature 383:525-528, 1996). Other members of the semaphorin family have been shown to be associated with other forms of biology. The human semaphorin E gene is expressed in rheumatoid synovial cells and is thought to play an immunosuppressive role via inhibition of cytokines (Mangasser-Stephan et al., *Biochem. Biophys. Res. Comm.* 234:153-156, 1997). CD100, a leukocyte semaphorin, promotes B-cell aggregation and differentiation (Hall et al., *Proc. Natl. Acad. Sci. USA* 93:11780-11785, 1996). CD100 has also been shown to be expressed in many T-cell lymphomas and may be a marker of malignant T-cell neoplasms (Dorfinan et al., *Am. J. Pathol.* 153:255-262, 1998). Semaphorin homologues have also been identified in DNA viruses (Lang, *Genomics* 51:340-350, 1998) and in poxvirus (Comeau, et al. *Immunity* 8:473-482, 1998). Transcription of the mouse semaphorin gene, M-semaH, correlates with metastatic ability of mouse tumor cell lines (Christensen et al., *Cancer Res.* 58:1238-1244, 1998).

The role of growth factors, other regulatory molecules, and their receptors in controlling cellular processes makes them likely candidates and targets for therapeutic intervention. Platelet-derived growth factor, for example, has been disclosed for the treatment of periodontal disease (U.S. Pat. No. 5,124,316), gastrointestinal ulcers (U.S. Pat. No. 5,234,908), and dermal ulcers (Robson et al., *Lancet* 339:23-25, 1992; Steed et al., *J. Vasc. Surg.* 21:71-81, 1995). Inhibition of PDGF receptor activity has been shown to reduce intimal hyperplasia in injured baboon arteries (Giese et al., Restenosis Summit VIII, Poster Session #23, 1996; U.S. Pat. No. 5,620,687). Vascular endothelial growth factors (VEGFs) have been shown to promote the growth of blood vessels in ischemic limbs (Isner et al., *The Lancet* 348:370-374, 1996), and have been proposed for use as wound-healing agents, for treatment of periodontal disease, for promoting endothelialization in vascular graft surgery, and for promoting collateral circulation following myocardial infarction (WIPO Publication No. WO 95/24473; U.S. Pat. No. 5,219,739). VEGFs are also useful for promoting the growth of vascular endothelial cells in culture. A soluble VEGF receptor (soluble flt-1) has been found to block binding of VEGF to cell-surface receptors and to inhibit the growth of vascular tissue in vitro (*Biotechnology News* 16(17):5-6, 1996).

In view of the proven clinical utility of hormones, there are needs in the art for additional such molecules for use as therapeutic agents, diagnostic agents, and research tools and reagents. These and other needs are addressed by the present invention.

DESCRIPTION OF THE INVENTION

The present invention provides an isolated polypeptide of at least 15 amino acid residues comprising an epitope-bearing portion of a protein of SEQ ID NO:2. Within certain embodiments, the polypeptide comprises a segment that is at least 90% identical to residues 46-163 of SEQ ID NO:2 or residues 235-345 of SEQ ID NO:2. Within additional embodiments, the polypeptide is selected from the group consisting of residues 15-163 of SEQ ID NO:2, residues 46-163 of SEQ ID NO:2, residues 15-170 of SEQ ID NO:2, residues 46-170 of SEQ ID NO:2, residues 15-234 of SEQ ID NO:2, residues 46-234 of SEQ ID NO:2, residues 15-229 amide of SEQ ID NO:2, residues 15-230 of SEQ ID NO:2, residues 15-345 of SEQ ID NO:2, residues 46-345 of SEQ ID NO:2, residues 235-345 of SEQ ID NO:2, and residues 226-345 of SEQ ID NO:2.

The invention also provides an isolated polypeptide comprising a sequence of amino acids of the formula $R1_x$-$R2_y$-$R3_z$, wherein R1 comprises a polypeptide of from 100 to 120 residues in length that is at least 90% identical to residues 46-163 of SEQ ID NO:2, and comprises a sequence motif C[KR]Y[DNE][WYF]X{11,15}G[KR][WYF]C (SEQ ID NO:4) corresponding to residues 104-124 of SEQ ID NO:2; R2 is a polypeptide at least 90% identical to residues 164-234 of SEQ ID NO:2; R3 is a polypeptide at least 90% identical in amino acid sequence to residues 235-345 of SEQ ID NO:2 and comprises cysteine residues at positions corresponding to residues 250, 280, 284, 296, 335, and 337 of SEQ ID NO:2, a glycine residue at a position corresponding to residue 282 of SEQ ID NO:2, and a sequence motif CX{18, 33}CXGXCX{6,33}CX{20,40}CXC (SEQ ID NO:3) corresponding to residues 250-337 of SEQ ID NO:2; and each of x, y, and z is individually 0 or 1, subject to the limitations that at least one of x and z is 1, and, if x and z are each 1, then y is 1. There are thus provided isolated polypeptides of the above formula wherein (a) x=1, (b) z=1, and (c) x=1 and z=1. Within certain embodiments, x=1 and R1 is at least 90% identical to residues 18-163 of SEQ ID NO:2. Within related embodiments, x=1 and R1 comprises residues 46-163 of SEQ ID NO:2. Within other embodiments, z=1, and R3 comprises residues 235-345 of SEQ ID NO:2. Within additional embodiments, x=1, z=1, and the polypeptide comprises residues 46-229 of SEQ ID NO:2, residues 164-345 of SEQ ID NO:2, or residues 46-345 of SEQ ID NO:2. The isolated polypeptide may further comprise cysteine residues at positions corresponding to residues 286, 287, 291, and 294 of SEQ ID NO:2. Within other embodiments, the isolated polypeptide further comprises an affinity tag. Within a related embodiment, the isolated polypeptide comprises an immunoglobulin constant domain.

The present invention also provides an isolated protein comprising a first polypeptide operably linked to a second polypeptide, wherein the first polypeptide comprises a sequence of amino acids of the formula $R1_x$-$R2_y$-$R3_z$ as disclosed above. The protein modulates cell proliferation, differentiation, metabolism, or migration. Within one embodiment, the protein is a heterodimer. Within related embodiments, the second polypeptide is selected from the group consisting of VEGF, VEGF-B, VEGF-C, VEGF-D, zvegf4, PlGF, PDGF-A, and PDGF-B. Within another embodiment, the protein is a homodimer.

There is also provided an isolated protein produced by a method comprising the steps of (a) culturing a host cell containing an expression vector comprising the following operably linked elements: a transcription promoter; a DNA segment encoding a polypeptide selected from the group consisting of (i) residues 46-345 of SEQ ID NO:2, (ii) residues 46-234 of SEQ ID NO:2, (iii) residues 164-345 of SEQ ID NO:2, and (iv) residues 235-345 of SEQ ID NO:2; and a transcription terminator, under conditions whereby the DNA segment is expressed; and (b) recovering from the cell the protein product of expression of the DNA construct.

Within another aspect of the invention there is provided an isolated polynucleotide of up to approximately 4 kb in length, wherein said polynucleotide encodes a polypeptide as disclosed above. Within one embodiment of the invention, the polynucleotide is DNA.

Within a further aspect of the invention there is provided an expression vector comprising the following operably linked elements: (a) a transcription promoter; (b) a DNA polynucleotide as disclosed above; and (c) a transcription terminator. The vector may further comprise a secretory signal sequence operably linked to the DNA polynucleotide.

Also provided by the invention is a cultured cell into which has been introduced an expression vector as disclosed above, wherein the cell expresses the polypeptide encoded by the DNA segment. The cultured cell can be used within a method of producing a polypeptide, the method comprising culturing the cell and recovering the expressed polypeptide.

The proteins provided herein can be combined with a pharmaceutically acceptable vehicle to provide a pharmaceutical composition.

The invention also provides an antibody that specifically binds to an epitope of a polypeptide as disclosed above. Antibodies of the invention include, inter alia, monoclonal antibodies and single chain antibodies, and may be linked to a reporter molecule.

The invention further provides a method for detecting a genetic abnormality in a patient, comprising the steps of (a) obtaining a genetic sample from a patient, (b) incubating the genetic sample with a polynucleotide comprising at least 14 contiguous nucleotides of SEQ ID NO:1 or the complement of SEQ ID NO:1, under conditions wherein said polynucleotide will hybridize to complementary polynucleotide sequence, to produce a first reaction product, and (c) comparing the first reaction product to a control reaction product, wherein a difference between the first reaction product and the control reaction product is indicative of a genetic abnormality in the patient.

Within an additional aspect, the invention provides a method of stimulating the growth of fibroblasts or smooth muscle cells comprising applying to the cells an effective amount of a protein as disclosed above.

Within another aspect the invention provides methods for modulating cell growth or other cellular processes. Within one embodiment there is provided a method of stimulating the growth of fibroblasts or smooth muscle cells comprising applying to the cells an effective amount of a protein as disclosed above. Within another embodiment there is provided a method of activating a cell-surface PDGF alpha receptor, comprising exposing a cell comprising a cell-surface PDGF alpha receptor to a polypeptide or protein as disclosed above, whereby the polypeptide or protein binds to and activates the receptor. Within a further embodiment there is provided a method of inhibiting a PDGF alpha receptor-mediated cellular process, comprising exposing a cell comprising a cell-surface PDGF alpha receptor to a compound that inhibits binding of a polypeptide or protein as disclosed above to the receptor.

Within a further method of the invention there is provided a method of inhibiting zvegf3 activity in a mammal comprising administering to the mammal an effective amount of a zvegf3 antagonist. Within certain embodiments the antagonist is an antibody, a receptor, a ligand-binding receptor fragment, or a receptor IgG-Fc fusion protein.

Within another aspect of the invention there is provided an isolated, antisense polynucleotide that is the complement of a polynucleotide encoding a polypeptide comprising a sequence of amino acids of the formula $R1_x$-$R2_y$-$R3_z$, wherein R1 comprises a polypeptide of from 100 to 120 residues in length that is at least 90% identical to residues 46-163 of SEQ ID NO:2, and comprises a sequence motif C[KR]Y[DNE][WYF]X{11,15}G[KR][WYF]C (SEQ ID NO:4) corresponding to residues 104-124 of SEQ ID NO:2; R2 is a polypeptide at least 90% identical to residues 164-234 of SEQ ID NO:2; R3 is a polypeptide at least 90% identical in amino acid sequence to residues 235-345 of SEQ ID NO:2 and comprises cysteine residues at positions corresponding to residues 250, 280, 284, 296, 335, and 337 of SEQ ID NO:2, a glycine residue at a position corresponding to residue 282 of SEQ ID NO:2, and a sequence motif CX{18, 33}CXGXCX{6,33}CX{20,40}CXC (SEQ ID NO:3) corresponding to residues 250-337 of SEQ ID NO:2; and each of x, y, and z is individually 0 or 1, subject to the limitations that at least one of x and z is 1, and, if x and z are each 1, then y is 1. Within one embodiment the antisense polynucleotide further comprises operably linked transcription promoter and terminator sequences. The antisense polynucleotide can be used within a method of inhibiting zvegf3 production in a cell comprising administering to the cell the antisense polynucleotide.

These and other aspects of the invention will become evident upon reference to the following detailed description of the invention and the attached drawings. In the drawings:

Figure 1B:
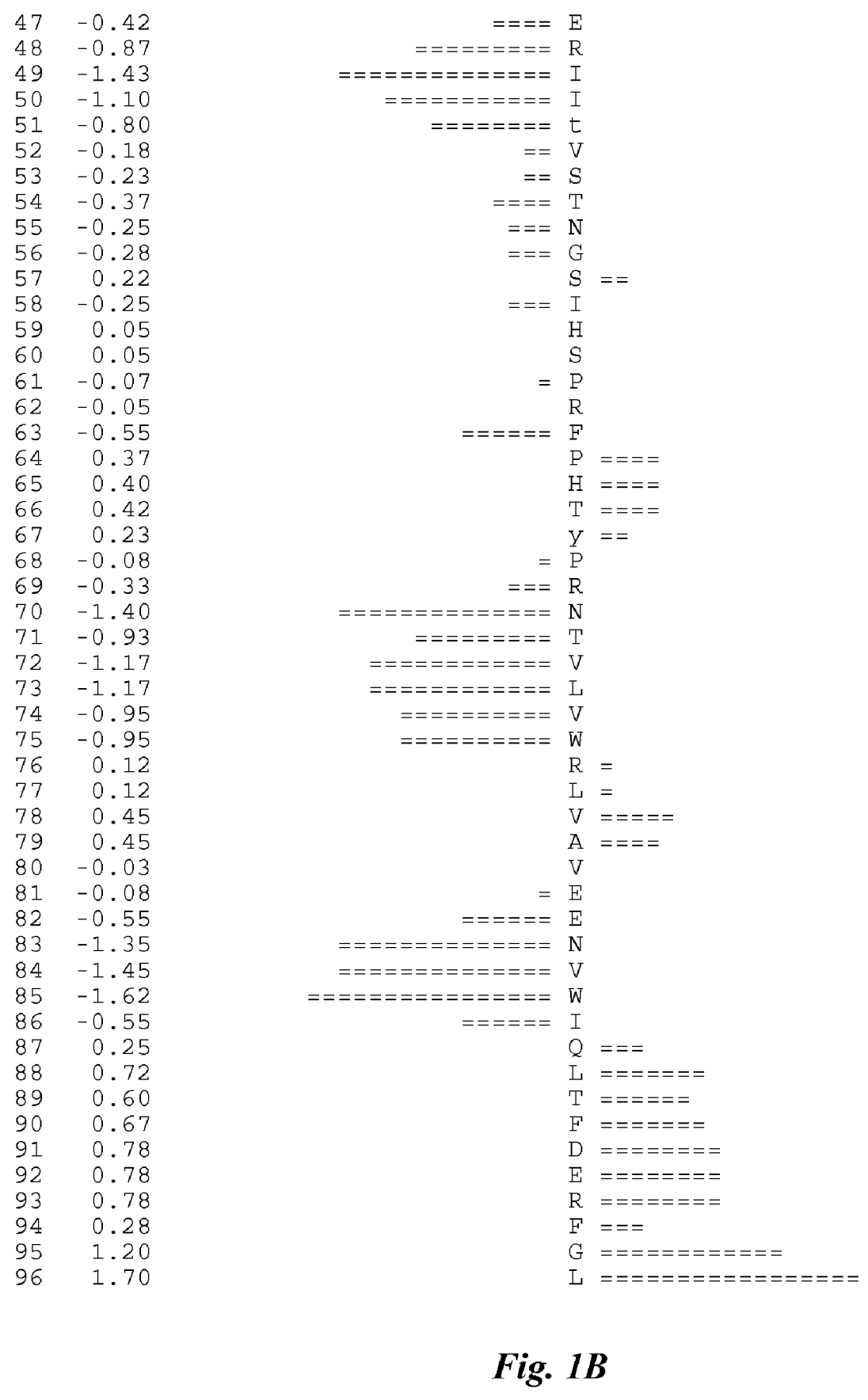
Figure 1C:
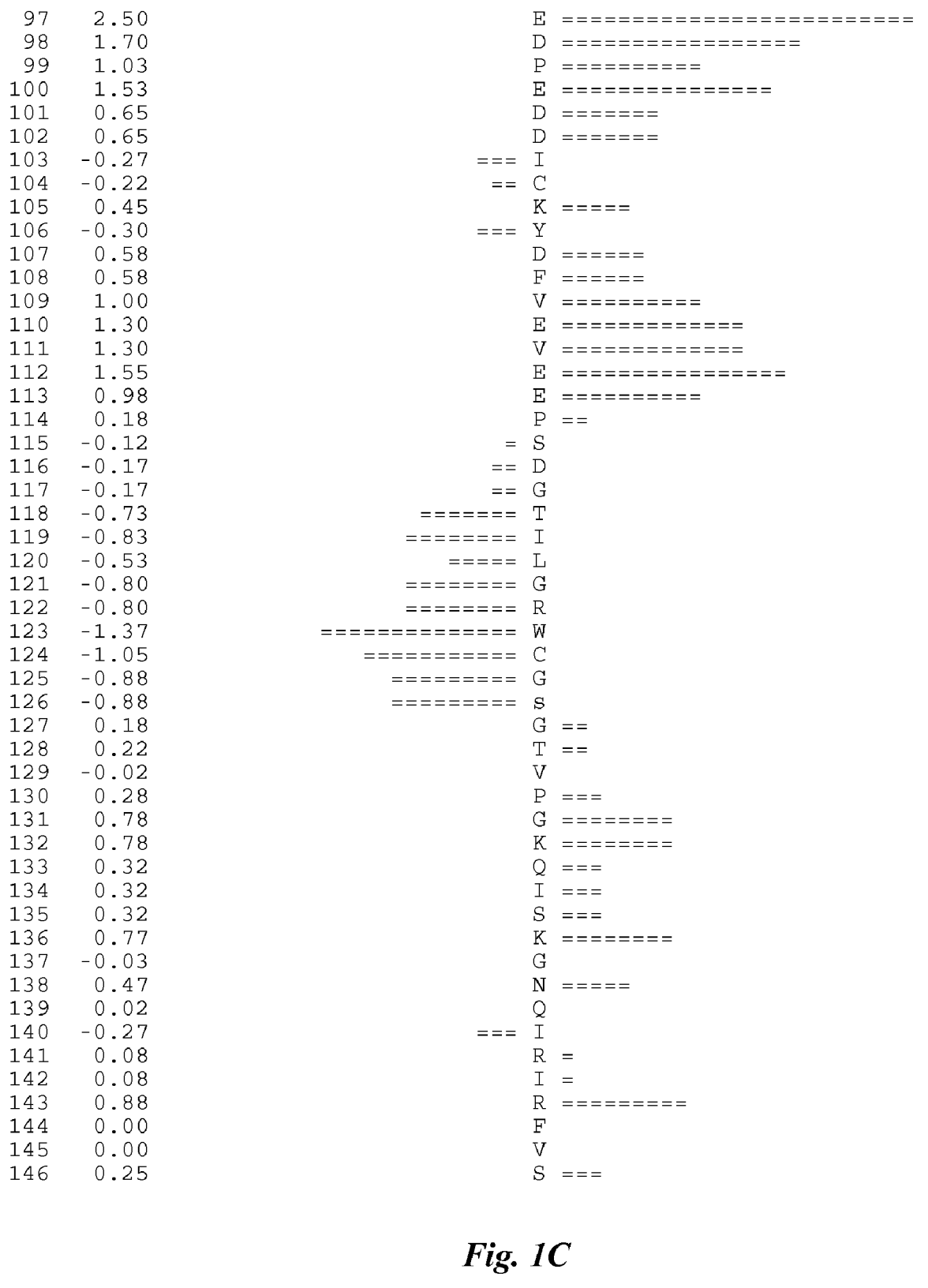
Figure 1D:
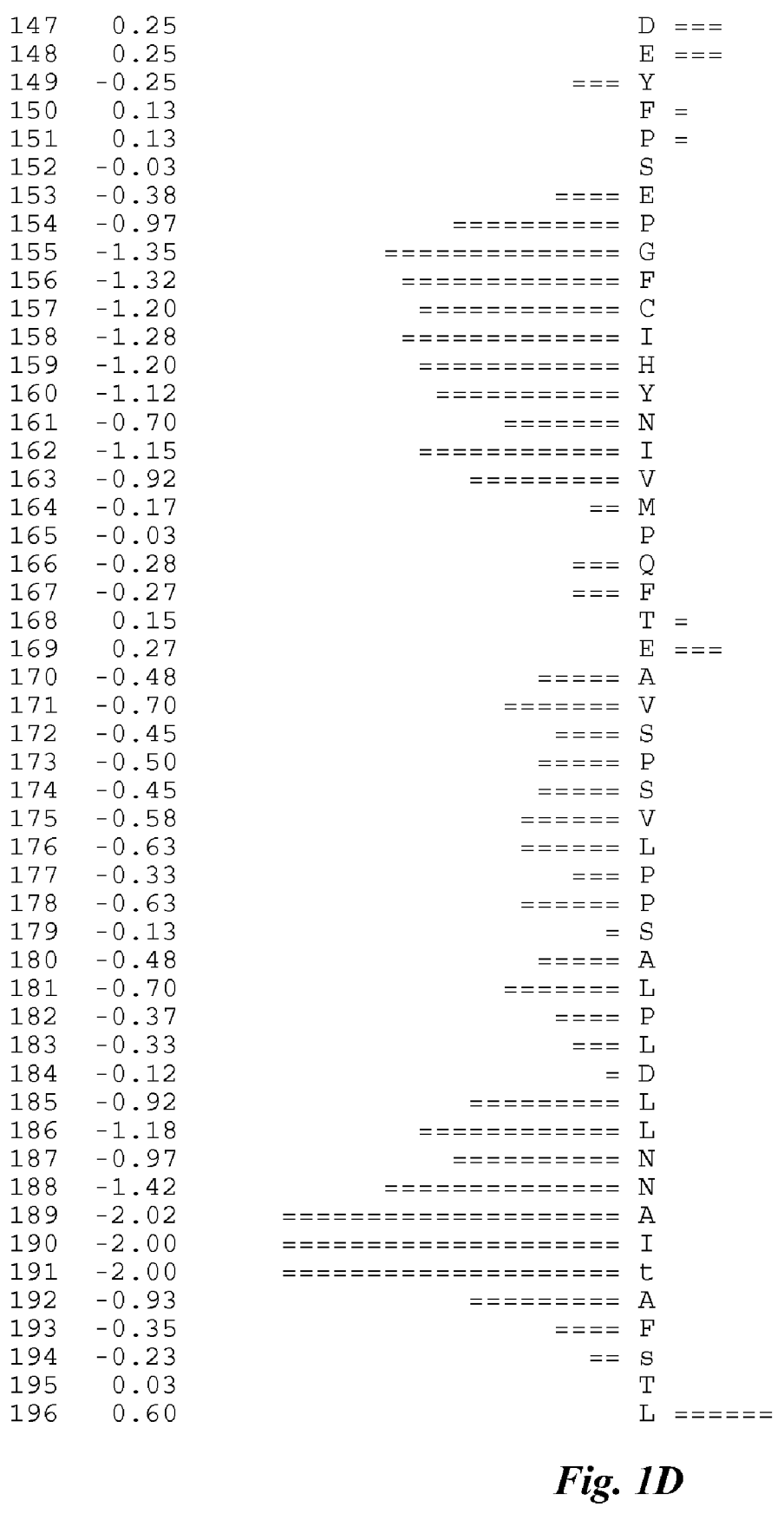
Figure 1E:
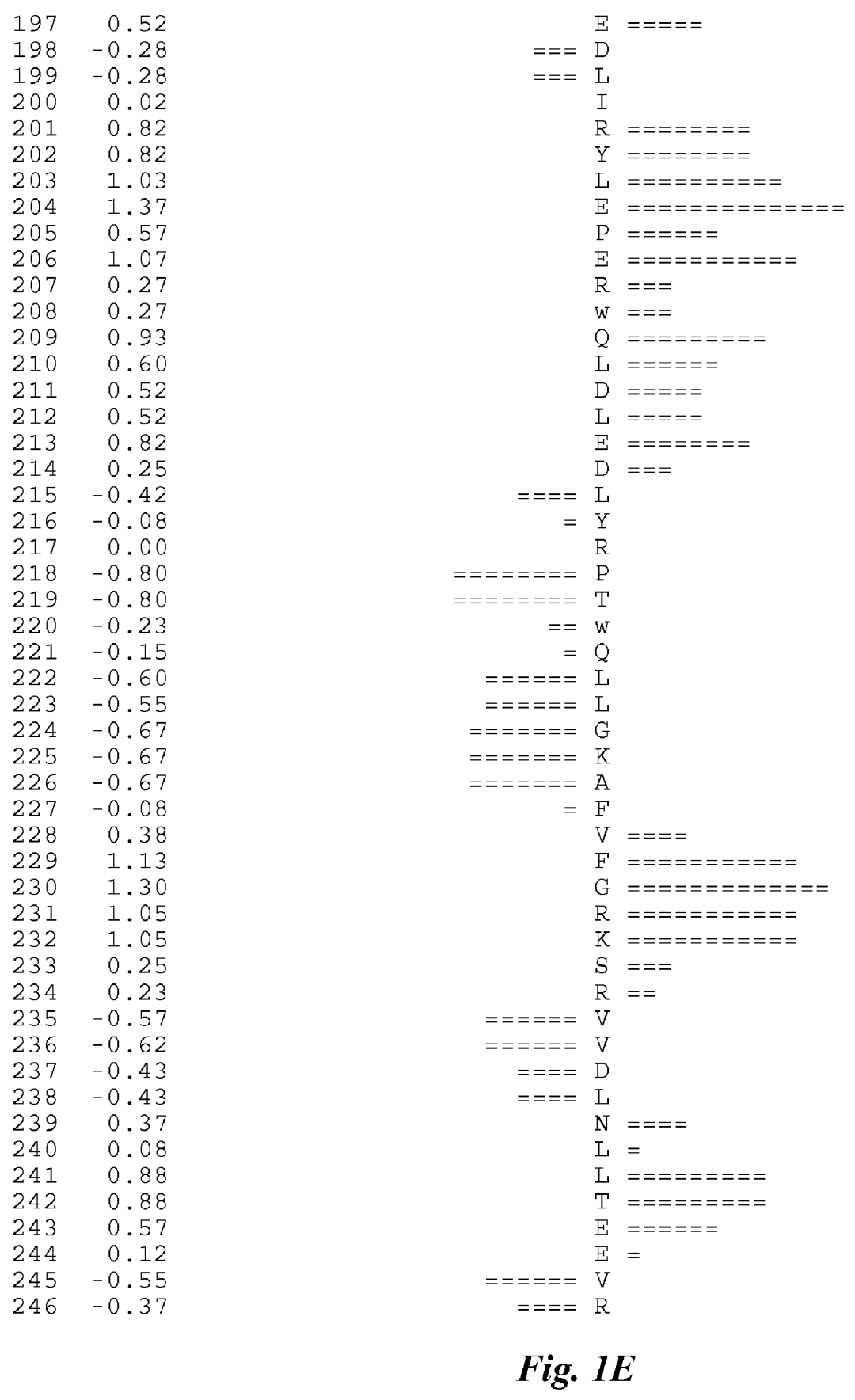

FIGS. 1A-1G are a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

FIG. 6 is an alignment of human (SEQ ID NO:2) and mouse (SEQ ID NO:43) amino acid sequences.

Figure 1A:
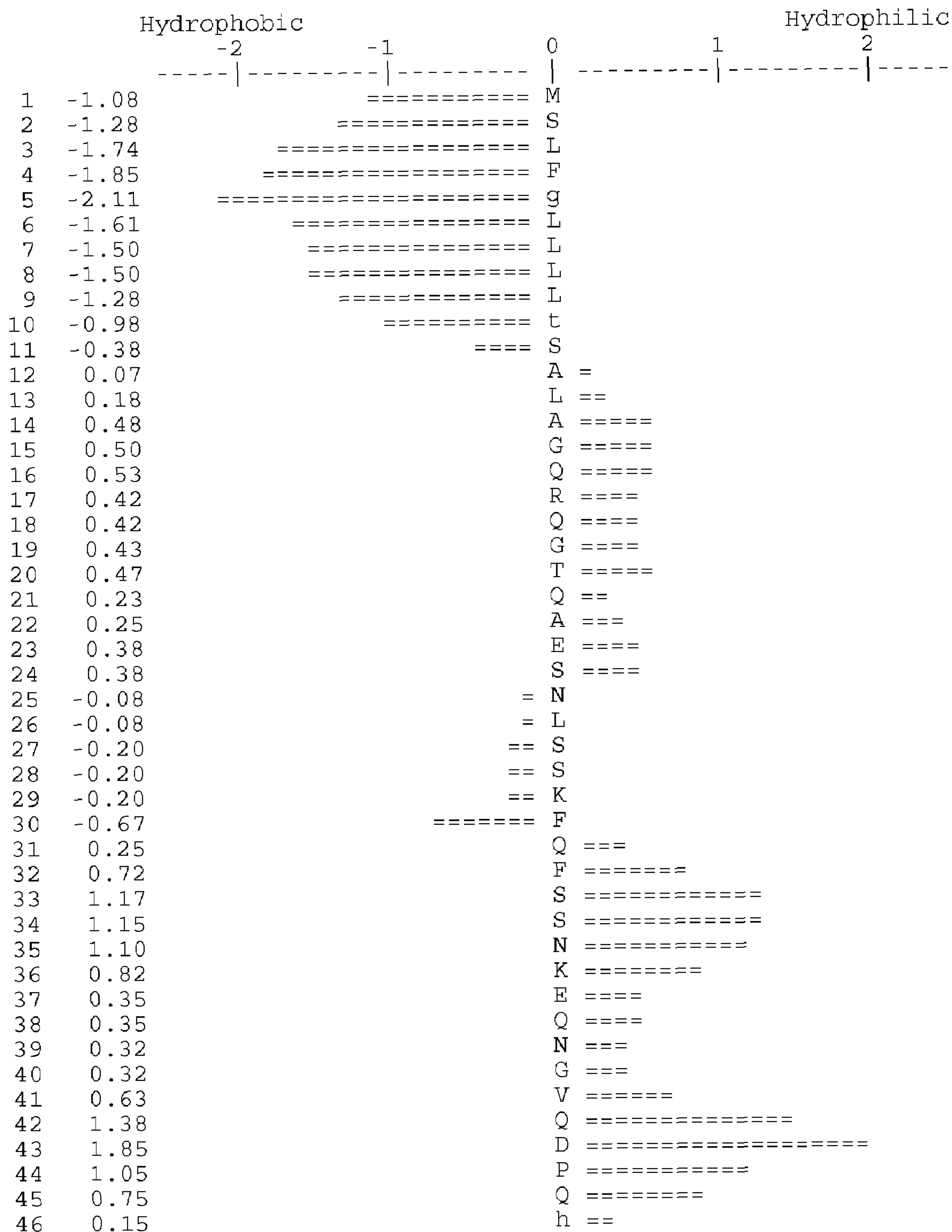
Figure 1G:
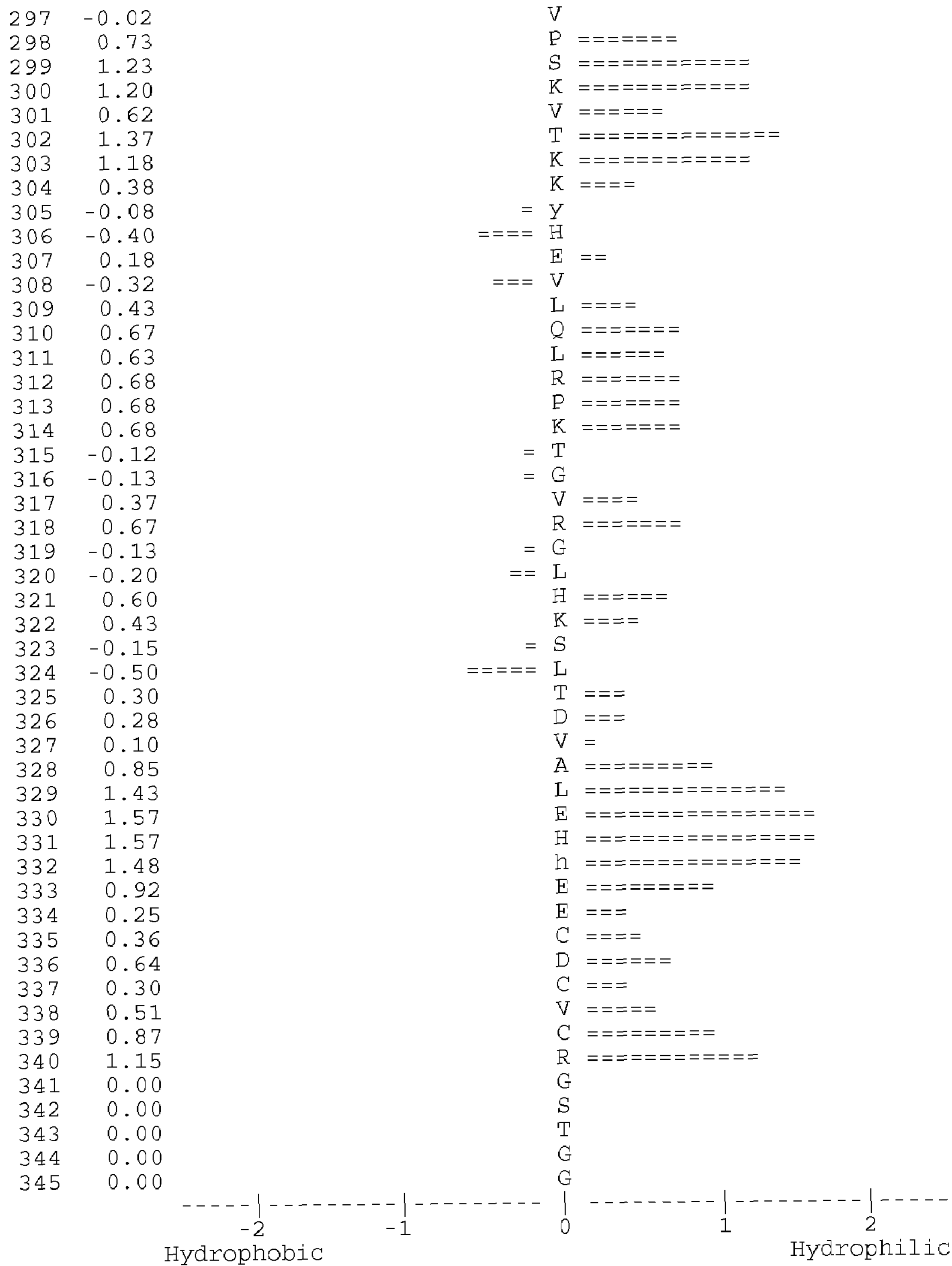

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459-463, 1982;

Guan et al., *Gene* 67:21-30, 1987), Glu-Glu affinity tag (Grussenmeyer et al., *Proc. Natl Acad. Sci. USA* 82:7952-4, 1985; see SEQ ID NO:5), substance P, Flag™ peptide (Hopp et al., *Biotechnology* 6:1204-10, 1988), streptavidin binding peptide, thioredoxin, ubiquitin, cellulose binding protein, T7 polymerase, or other antigenic epitope or binding domain. See, in general, Ford et al., *Protein Expression and Purification* 2: 95-107, 1991. DNAs encoding affinity tags and other reagents are available from commercial suppliers (e.g., Pharmacia Biotech, Piscataway, N.J.; New England Biolabs, Beverly, Mass. and Eastman Kodak, New Haven, CT).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "beta-strand-like region" is a region of a protein characterized by certain combinations of the polypeptide backbone dihedral angles phi ($\phi$) and psi ($\psi$). Regions wherein $\phi$ is less than $-60°$ and $\psi$ is greater than 90° are beta-strand-like. Those skilled in the art will recognize that the limits of a $\beta$-strand are somewhat imprecise and may vary with the criteria used to define them. See, for example, Richardson and Richardson in Fasman, ed., Prediction of Protein Structure and the Principles of Protein Conformation, Plenum Press, New York, 1989; and Lesk, *Protein Architecture: A Practical Approach*, Oxford University Press, New York, 1991.

A "complement" of a polynucleotide molecule is a polynucleotide molecule having a complementary base sequence and reverse orientation as compared to a reference sequence. For example, the sequence 5'ATGCACGGG 3' is complementary to 5' CCCGTGCAT 3'.

"Corresponding to", when used in reference to a nucleotide or amino acid sequence, indicates the position in a second sequence that aligns with the reference position when two sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. Within one form, the isolated polypeptide or protein is substantially free of other polypeptides or proteins, particularly other polypeptides or proteins of animal origin. Polypeptides and proteins can be provided in a highly purified form, i.e. greater than 95% pure or greater than 99% pure. When used in this context, the term "isolated" does not exclude the presence of the same polypeptide or protein in alternative physical forms, such as dimers or alternatively glycosylated or derivatized forms.

A "motif" is a series of amino acid positions in a protein sequence for which certain amino acid residues are required. A motif defines the set of possible residues at each such position.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "ortholog" denotes a polypeptide or protein obtained from one species that is the functional counterpart of a polypeptide or protein from a different species. Sequence differences among orthologs are the result of speciation.

A "PDGF alpha receptor-mediated cellular process" is a cellular process that occurs in response to activation of a PDGF alpha receptor. Such processes include, without limitation, cell division, chemotaxis, cell differentiation, and production or release of macromolecules.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±20%.

All references cited herein are incorporated by reference in their entirety.

The present invention is based in part upon the discovery of a novel DNA molecule that encodes a polypeptide comprising a growth factor domain and a CUB domain. The growth factor domain is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295-307, 1991; Soker et al., ibid.), human bone morphogenetic protein-I (Wozney et al., *Science* 242:1528-1534, 1988), porcine seminal plasma protein and bovine acidic seminal fluid protein (Romero et al., *Nat. Struct. Biol.* 4:783-788, 1997), and *X. laevis* tolloid-like protein (Lin et al., *Dev. Growth Differ.* 39:43-51, 1997). Analysis of the tissue distribution of the mRNA corresponding to this novel DNA showed that expression was widespread in adult human tissues, and that expression occured up to day 15 in mouse embryo. The polypeptide has been designated "zvegf3 " in view of its homology to the VEGFs in the growth factor domain.

Structural predictions based on the zvegf3 sequence and its homology to other growth factors suggests that the polypeptide can form homomultimers or heteromultimers that act on tissues to control organ development by modulating cell proliferation, migration, differentiation, or metabolism. Zvegf3 heteromultimers may comprise a polypeptide from another member of the PDGFNVEGF family of proteins, including VEGF, VEGF-B, VEGF-C, VEGF-D, zvegf4 (SEQ ID NOS: 36 and 37), PlGF (Maglione et al., *Proc. Natl. Acad. Sci. USA* 88:9267-9271, 1991), PDGF-A (Murray et al., U.S. Pat. No. 4,899,919; Heldin et al., U.S. Pat. No. 5,219,759), or PDGF-B (Chiu et al., *Cell* 37:123-129, 1984; Johnsson et al., *EMBO J.* 3:921-928, 1984). Members of this family of polypeptides regulate organ development and regeneration, post-developmental organ growth, and organ maintenance, as well as tissue maintenance and repair processes. These factors are also involved in pathological processes where therapeutic treatments are required, including cancer, rheumatoid arthritis, diabetic retinopathy, ischemic limb disease, peripheral vascular disease, myocardial ischemia, vascular intimal hyperplasia, atherosclerosis, and hemangioma formation. To treat these pathological conditions it will often be required to develop compounds to antagonize the members of the PDGF/VEGF family of proteins, or their respective receptors. This may include the development of neutralizing antibodies, small molecule antagonists, modified forms of the growth factors that maintain receptor binding activity but lack receptor activating activity, soluble receptors, or antisense or ribozyme molecules to block polypeptide production.

SEQ ID NO:2 is the sequence of a representative polypeptide of the present invention. Analysis of the amino acid sequence shown in SEQ ID NO:2 indicates that residues 1 to 14 form a secretory peptide. The CUB domain extends from residue 46 to residue 163. A propeptide-like sequence extends from residue 164 to residue 234, and includes two potential cleavage sites at its carboxyl terminus, a dibasic site at residues 231-232 and a target site for furin or a furin-like protease at residues 231-234. The growth factor domain extends from residue 235 to residue 345. Those skilled in the art will recognize that domain boundaries are somewhat imprecise and can be expected to vary by up to ±5 residues from the specified positions. Potential proteolytic cleavage sites occur at residues 232 and 234. Processing of recombinant zvegf3 produced in BHK cells has been found to occur between residues 225 and 226. Signal peptide cleavage is predicted to occur after residue 14 (±3 residues). This analysis suggests that the zvegf3 polypeptide chain may be cleaved to produce a plurality of monomeric species as shown in Table 1. Cleavage after Arg-234 is expected to result in subsequent removal of residues 231-234, with possible conversion of Gly-230 to an amide. Cleavage after Lys-232 is expected to result in subsequent removal of residue 231, again with possible conversion of Gly-230 to an amide. In addition, it may be advantageous to include up to seven residues of the interdomain region at the carboxyl terminus of the CUB domain. The interdomain region can be truncated at its amino terminus by a like amount. See Table 1.

TABLE 1

| Monomer | Residues (SEQ ID NO: 2) |
|---|---|
| Cub domain | 15-163 |
| | 46-163 |
| | 15-170 |
| | 46-170 |
| CUB domain + interdomain region | 15-234 |
| | 46-234 |
| | 15-229 |
| | amide |
| | 15-230 |
| Cub domain + interdomain region + growth factor domain | 15-345 |
| | 46-345 |
| Growth factor domain | 235-345 |
| | 226-345 |
| Growth factor domain + interdomain region | 164-345 |
| | 171-345 |

Also included within the present invention are polypeptides that are at least 90% identical or at least 95% identical to the polypeptides disclosed in Table 1, wherein these additional polypeptides retain certain characteristic sequence motifs as disclosed below.

Zvegf3 polypeptides are designated herein with a subscript indicating the amino acid residues. For example, the CUB domain polypeptides disclosed in Table 1 are designated "zvegf3$_{15-163}$", "zvegf3$_{46-163}$", "zvegf3$_{15-170}$", and "zvegf3$_{46-170}$".

Higher order structure of zvegf3 polypeptides can be predicted by sequence alignment with known homologs and computer analysis using available software (e.g., the Insight II® viewer and homology modeling tools; MSI, San Diego, Calif.). Analysis of SEQ ID NO:2 predicts that the secondary structure of the growth factor domain is dominated by the cystine knot, which ties together variable beta strand-like regions and loops into a bow tie-like structure. Sequence alignment indicates that Cys residues within the growth factor domain at positions 250, 280, 284, 296, 335, and 337, and Gly 282 are highly conserved within the family. Further analysis suggests pairing (disulfide bond formation) of Cys residues 250 and 296, 280 and 335, and 284 and 337 to form the cystine knot. This arrangement of conserved residues can be represented by the formula CX{18,33}CXGXCX{6,33}CX{20, 40}CXC (SEQ ID NO:3), wherein amino acid residues are represented by the conventional single-letter code, X is any amino acid residue, and {y,z} indicates a region of variable residues (X) from y to z residues in length. A consensus bow tie structure is formed as: amino terminus to cystine knot→beta strand-like region 1→variable loop 1→beta strand-like region 2→cystine knot→beta strand-like region 3→variable loop 2→beta strand-like region 4→cystine knot→beta strand-like region 5→variable loop 3→beta strand-like region 6 →cystine knot. Variable loops 1 and 2 form one side of the bow tie, with variable loop 3 forming the other side. The structure of the zvegf3 growth factor domain appears to diverge from the consensus structure of other family members in loop 2 and beta strand-like regions 3 and 4, wherein all are abbreviated and essentially replaced by a cysteine cluster comprising residues 285 (Ala) through 295 (Gln), which includes Cys residues at positions 286, 287, 291, and 294 of SEQ ID NO:2. The approximate boundaries of the beta strand-like regions in SEQ ID NO:2 are: region 1, residues 251-259; region 2, residues 275-279; region 5, residues 297-301; region 6, residues 329-334. Loops separate regions 1 and 2, and regions 5 and 6.

The CUB domain of zveg3 is believed to form a beta barrel structure with nine distinct beta strand-like regions. These regions comprise residues 48-51, 55-59, 72-78, 85-90, 92-94, 107-112, 119-123, 139-146, and 156-163 of SEQ ID NO:2. A multiple alignment of CUB domains of *Xenopus laevis* neuropilin precursor (Takagi et al., ibid.), human BMP-1 (Wozney et al., ibid.), and *X. laevis* tolloid-like protein (Lin et al., ibid.) indicates the presence of a conserved motif corresponding to residues 104-124 of SEQ ID NO:2. This motif is represented by the formula C[KR]Y[DNE][WYF]X{11, 15}G[KR][WYF]C (SEQ ID NO:4), wherein square brackets indicate the allowable residues at a given position and X{y,z} is as defined above.

The proteins of the present invention include proteins comprising CUB domains homologous to the CUB domain of zvegf. These homologous domains are from 100 to 120 residues in length and comprise a motif of the sequence C[KR] Y[DNE][WYF]X{11,15}G[KR][WYF]C (SEQ ID NO:4) corresponding to residues 104-124 of SEQ ID NO:2. These homologous CUB domains are at least 90% identical to residues 46-163 of SEQ ID NO:2 or at least 95% identical to residues 46-163 of SEQ ID NO:2.

CUB domain-containing proteins of the present invention may further include a zvegf3 interdomain region or homolog thereof. The interdomain region is at least 90% identical to residues 164 to 234 of SEQ ID NO:2.

Additional proteins of the present invention comprise the zvegf3 growth factor domain or a homolog thereof. These proteins thus comprise a polypeptide segment that is at least 90% or 95% identical to residues 235-345 of SEQ ID NO:2, wherein the polypeptide segment comprises Cys residues at positions corresponding to residues 250, 280, 284, 296, 335, and 337 of SEQ ID NO:2; a glycine at a position corresponding to residue 284 of SEQ ID NO:2; and the sequence motif CX{18,33}CXGXCX{6,33}CX{20,40}CXC (SEQ ID NO:3) corresponding to residues 250-337 of SEQ ID NO:2.

Additional proteins comprising combinations of the CUB domain, interdomain region, and growth factor domain are shown above in Table 1. In each case, the invention also includes homologous proteins comprising homologous domains as disclosed above.

Structural analysis and homology predict that zvegf3 polypeptides complex with a second polypeptide to form multimeric proteins. These proteins include homodimers and heterodimers. In the latter case, the second polypeptide can be a truncated or other variant zvegf3 polypeptide or another polypeptide, such as a PlGF, PDGF-A, PDGF-B, VEGF, VEGF-B, VEGF-C, VEGF-D, or zvegf4 polypeptide. Among the dimeric proteins within the present invention are dimers formed by non-covalent association (e.g., hydrophobic interactions) with a second subunit, either a second zvegf3 polypeptide or other second subunit, or by covalent association stabilized by intermolecular disulfide bonds between cysteine residues of the component monomers. Within SEQ ID NO:2, the Cys residues at positions 274, 286, 287, 291, 294, and 339 may form intramolecular or intermolecular disulfide bonds. It is likely that residues 274 and 287 form interchain disulfide bonds. In homodimers, the component polypeptides (designated A and B) may be joined in an anti-parallel arrangement with a pattern of interchain disulfide bonds A274-B287, A287-B274. The data further suggest that additional intrachain disulfides are formed by the pairing of Cys286 with Cys291, and Cys294 with Cys339, although some or all of these four residues may be involved in interchain pairing.

The present invention thus provides a variety of multimeric proteins comprising a zvegf3 polypeptide as disclosed above. These zvegf3 polypeptides include $zvegf3_{15-234}$, $zvegf3_{46-234}$, $zvegf3_{15-229}$ amide, $zvegf3_{15-230}$, $zvegf3_{15-345}$, $zvegf3_{46-345}$, and $zvegf3_{235-345}$, as well as variants and derivatives of these polypeptides as disclosed herein.

Percent sequence identity is determined by conventional methods. See, for example, Altschul et al., *Bull. Math. Bio.* 48:603-616, 1986, and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "BLOSUM62"scoring matrix of Henikoff and Henikoff (ibid.) as shown in Table 2 (amino acids are indicated by the standard one-letter codes). The percent identity is then calculated as:

$$\frac{\text{Total number of identical matches}}{\left[\begin{array}{l}\text{length of the longer sequence plus the}\\ \text{number of gaps introduced into the longer}\\ \text{sequence in order to align the two sequences}\end{array}\right]}\times 100$$

TABLE 2

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The level of identity between amino acid sequences can be determined using the "FASTA" similarity search algorithm disclosed by Pearson and Lipman (*Proc. Natl. Acad. Sci. USA* 85:2444, 1988) and by Pearson (*Meth. Enzymol.* 183:63, 1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The present invention includes polypeptides having one or more conservative amino acid changes as compared with the amino acid sequence of SEQ ID NO:2. The BLOSUM62 matrix (Table 2) is an amino acid substitution matrix derived from about 2,000 local multiple alignments of protein sequence segments, representing highly conserved regions of more than 500 groups of related proteins (Henikoff and Henikoff, ibid.). Thus, the BLOSUM62 substitution frequencies can be used to define conservative amino acid substitutions that may be introduced into the amino acid sequences of the present invention. As used herein, the term "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least one 1 (e.g., 1, 2 or 3), while more preferred conservative amino acid substitutions are characterized by a BLOSUM62 value of at least 2 (e.g., 2 or 3).

The proteins of the present invention can further comprise amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20-25 residues, or a polypeptide extension that facilitates purification (an affinity tag) as disclosed above. Two or more affinity tags may be used in combination. Polypeptides comprising affinity tags can further comprise a polypeptide linker and/or a proteolytic cleavage site between the zvegf3 polypeptide and the affinity tag. Exemplary cleavage sites include thrombin cleavage sites and factor Xa cleavage sites.

The present invention further provides a variety of other polypeptide fusions and related multimeric proteins comprising one or more polypeptide fusions. For example, a zvegf3 polypeptide can be prepared as a fusion to a dimerizing protein as disclosed in U.S. Pat. Nos. 5,155,027 and 5,567,584. Exemplary dimerizing proteins in this regard include immunoglobulin constant region domains. Dimerization can also be stabilized by fusing a zvegf3 polypeptide to a leucine zipper sequence (Riley et al., *Protein Eng.* 9:223-230, 1996; Mohamed et al., *J. Steroid Biochem. Mol. Biol.* 51:241-250, 1994). Immunoglobulin-zvegf3 polypeptide fusions and leucine zipper fusions can be expressed in genetically engineered cells to produce a variety of multimeric zvegf3 analogs. Auxiliary domains can be fused to zvegf3 polypeptides to target them to specific cells, tissues, or macromolecules (e.g., collagen). For example, a zvegf3 polypeptide or protein can be targeted to a predetermined cell type by fusing a zvegf3 polypeptide to a ligand that specifically binds to a receptor on the surface of the target cell. In this way, polypeptides and proteins can be targeted for therapeutic or diagnostic purposes. A zvegf3 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

Polypeptide fusions of the present invention will generally contain not more than about 1,500 amino acid residues, often not more than about 1,200 residues, often not more than about 1,000 residues, and will in many cases be considerably smaller. For example, a zvegf3 polypeptide of 331 residues (residues 15-345 of SEQ ID NO:2) can be fused to *E. coli* β*galactosidase* (1,021 residues; see Casadaban et al., *J. Bacteriol.* 143:971-980, 1980), a 10-residue spacer, and a 4-residue factor Xa cleavage site to yield a polypeptide of 1366 residues. In a second example, residues 235-345 of SEQ ID NO:2 can be fused to maltose binding protein (approximately 370 residues), a 4-residue cleavage site, and a 6-residue polyhistidine tag.

A polypeptide comprising the zvegf3 growth factor domain (e.g., $zvegf3_{235-345}$ or $zvegf3_{64-345}$) can be fused to a non-zvegf3 CUB domain. Within a related embodiment of the invention, a zvegf3 polypeptide comprising zvegf3 growth factor and CUB domains is fused to a non-zvegf3 CUB domain, such as a CUB-domain comprising neuropilin polypeptide.

The present invention further provides polypeptide fusions comprising the zvegf3 CUB domain (e.g., $zvegf3_{45-163}$). The CUB domain, with its homology to neuropilin-1, may be used to target zvegf3 or other proteins containing it to cells having cell-surface semaphorins, including endothelial cells, neuronal cells, lymphocytes, and tumor cells. The zvegf3 CUB domain can thus be joined to other moities, including polypeptides (e.g., other growth factors, antibodies, and enzymes) and non-peptidic moieties (e.g., radionuclides, contrast agents, and the like), to target them to cells expressing cell-surface semaphorins. The dibasic and furin-like sites between the CUB and growth factor domains of zvegf3 may allow for proteolytic release of the growth factor domain or other moiety through existing local proteases within tissues, or by proteases added from exogenous sources. The release of the targetted moiety may provide more localized biological effects.

Proteins comprising the wild-type zvegf3 CUB domain and variants thereof may be used to modulate activities mediated by cell-surface semaphorins. While not wishing to be bound by theory, zvegf3 may bind to semaphorins via its CUB domain. The observation that semaphorin III is involved in vascular development suggests that members of the vascular growth factor family of proteins may also be involved, especially due to the co-binding activity of VEGF and semaphorin III to neuropilin-1. Zvegf3 may thus be used to design agonists and antagonist of neuropilin-semaphorin interactions. For example, the zvegf3 sequence disclosed herein provides a starting point for the design of molecules that antagonize semaphorin-stimulated activities, including neurite growth, cardiovascular development, cartilage and limb development, and T and B-cell function. Additional applications include intervention in various pathologies, including rheumatoid arthritis, various forms of cancer, autoimmune disease, inflammation, retinopathies, hemangiomas, ischemic events within tissues including the heart, kidney and peripheral arteries, neuropathies, acute nerve damage, and diseases of the central and peripheral nervous systems.

The isolated CUB domain of zvegf3 (and multimers thereof) may also be useful to block binding of other zvegf3 molecules (e.g., full-length polypeptide, isolated growth factor domain, or multimers thereof) to cell-surface molecules and/or extracellular binding sites by itself binding to such molecules or sites.

Amino acid sequence changes are made in zvegf3 polypeptides so as to minimize disruption of higher order structure essential to biological activity. In general, conservative amino acid changes are preferred. Changes in amino acid residues will be made so as not to disrupt the cystine knot and "bow tie" arrangement of loops in the growth factor domain that is characteristic of the protein family. Conserved motifs will also be maintained. The effects of amino acid sequence changes can be predicted by computer modeling as disclosed above or determined by analysis of crystal structure (see, e.g., Lapthom et al., ibid.). A hydrophobicity profile of SEQ ID NO:2 is shown in FIGS. 1A-1G. Those skilled in the art will recognize that this hydrophobicity will be taken into account when designing alterations in the amino acid sequence of a zvegf3 polypeptide, so as not to disrupt the overall profile. Additional guidance in selecting amino acid subsitutions is provided by the alignment of mouse and human zvegf3 sequences shown in FIG. 6.

The polypeptides of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents.

Proteins are purified by chromatography. See, for example, Robertson et al., *J. Am. Chem. Soc.* 113:2722, 1991; Ellman et al., *Methods Enzymol.* 202:301, 1991; Chung et al., Science 259:806-809, 1993; and Chung et al., *Proc. Natl. Acad. Sci. USA* 90:10145-10149, 1993). In a second method, translation is carried out in *Xenopus* oocytes by microinjection of mutated mRNA and chemically aminoacylated suppressor tRNAs (Turcatti et al., *J. Biol. Chem.* 271:19991-19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

Essential amino acids in the polypeptides of the present invention can be identified according to procedures known in the art, such as site-directed mutagenesis or alanine-scanning mutagenesis (Cunningham and Wells, *Science* 244, 1081-1085, 1989; Bass et al., *Proc. Natl. Acad. Sci. USA* 88:4498-4502, 1991). In the latter technique, single alanine mutations are introduced at every residue in the molecule, and the resultant mutant molecules are tested for biological activity of other properties to identify amino acid residues that are critical to the activity of the molecule.

Multiple amino acid substitutions can be made and tested using known methods of mutagenesis and screening, such as those disclosed by Reidhaar-Olson and Sauer (Science 241: 53-57, 35 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., DNA 7:127, 1988).

Variants of the disclosed zvegf3 DNA and polypeptide sequences can be generated through DNA shuffling as disclosed by Stemmer, *Nature* 370:389-391, 1994 and Stemmer, *Proc. Natl. Acad. Sci. USA* 91:10747-10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high volume or high-throughput screening methods to detect biological activity of zvegf3 variant polypeptides, in particular biological activity in modulating cell proliferation or cell differentiation. For example, mitogenesis assays that measure dye incorporation or $^3$H-thymidine incorporation can be carried out on large numbers of samples, as can cell-based assays that detect expression of a reporter gene (e.g., a luciferase gene). Mutagenesis of the CUB domain can be used to modulate its binding to members of the semaphorin family, including enhancing or inhibiting binding to selected family members. A modified spectrum of binding activity may be desirable for optimizing therapeutic and/or diagnostic utility of proteins comprising a zvegf3 CUB domain. Direct binding utilizing labeled CUB protein can be used to monitor changes in CUB domain binding activity to selected semaphorin family members. Semaphorins of interest in this regard include isolated proteins, proteins present in cell membranes, and proteins present on cell-surfaces. The CUB domain can be labeled by a variety of methods including radiolabeling with isotopes, such as $^{125}$I, conjugation to enzymes such as alkaline phosphatase or horseradish peroxidase, conjugation with biotin, and conjugation with various fluorescent markers including FITC. These and other assays are disclosed in more detail below. Mutagenized DNA molecules that encode active zvegf3 polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are homologous to the zvegf3 polypeptides disclosed above in Table 1 and retain the biological properties of the wild-type protein. Such polypeptides can also include additional polypeptide segments as generally disclosed above.

The present invention also provides polynucleotide molecules, including DNA and RNA molecules, that encode the zvegf3 polypeptides disclosed above. The polynucleotides of the present invention include the sense strand; the anti-sense strand; and the DNA as double-stranded, having both the sense and anti-sense strand annealed together by hydrogen bonds. A representative DNA sequences encoding zvegf3 polypeptides is set forth in SEQ ID NO:1. Additional DNA sequences encoding zvegf3 polypeptides can be readily generated by those of ordinary skill in the art based on the genetic code. Counterpart RNA sequences can be generated by substitution of U for T.

Those skilled in the art will readily recognize that, in view of the degeneracy of the genetic code, considerable sequence variation is possible among polynucleotide molecules encoding zvegf3 polypeptides. SEQ ID NO:6 is a degenerate DNA sequence that encompasses all DNAs that encode the zvegf3 polypeptide of SEQ ID NO:2. Those skilled in the art will recognize that the degenerate sequence of SEQ ID NO:6 also provides all RNA sequences encoding SEQ ID NO:2 by substituting U for T. Thus, zvegf3 polypeptide-encoding polynucleotides comprising nucleotides 1-1035, 1-489, 43-489, 136-489, 43-702, 136-702, 43-690, 43-1035, 136-1035, and 703-1035 of SEQ ID NO:6 and their RNA equivalents are contemplated by the present invention. Table 3 sets forth the one-letter codes used within SEQ ID NO:6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 3

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:6, encompassing all possible codons for a given amino acid, are set forth in Table 4, below.

TABLE 4

| Amino Acid | One-Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | · | TAA TAG TGA | TRR |
| Asn\|Asp | B | | RAY |
| Glu\|Gln | Z | | SAR |
| Any | X | | NNN |
| Gap | — | --- | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequences may encode variant amino acid sequences, but one of ordinary skill in the art can easily identify such variant sequences by reference to the amino acid sequence of SEQ ID NO: 2. Variant sequences can be readily tested for functionality as described herein.

Within certain embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point $T_m$ for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. Complementary DNA (cDNA) clones are prepared from RNA that is isolated from a tissue or cell that produces large amounts of zvegf3 RNA. Such tissues and cells are identified by Northern blotting (Thomas, *Proc. Natl. Acad. Sci. USA* 77:5201, 1980), and include thyroid, spinal cord, and adrenal gland. Total RNA can be prepared using guanidine HCl extraction followed by isolation by centrifugation in a CsCl gradient (Chirgwin et al., *Biochemistry* 18:52-94, 1979). Poly (A)+RNA is prepared from total RNA using the method of Aviv and Leder (*Proc. Natl. Acad. Sci. USA* 69:1408-1412, 1972). Complementary DNA (cDNA) is prepared from poly(A)+RNA using known methods. In the alternative, genomic DNA can be isolated. For some applications (e.g., expression in transgenic animals) it may be preferable to use a genomic clone, or to modify a cDNA clone to include at least one genomic intron. Methods for identifying and isolating cDNA and genomic clones are well known and within the level of ordinary skill in the art, and include the use of the sequence disclosed herein, or parts thereof, for probing or priming a library. Polynucleotides encoding zvegf3 polypeptides are identified and isolated by, for example, hybridization or polymerase chain reaction ("PCR", Mullis, U.S. Pat. No. 4,683,202). Expression libraries can be probed with antibodies to zvegf3, receptor fragments, or other specific binding partners.

Those skilled in the art will recognize that the sequences disclosed in SEQ ID NOS:1 and 2 represent a single allele of human zvegf3. Allelic variants of these sequences can be cloned by probing cDNA or genomic libraries from different individuals according to standard procedures. Alternatively spliced forms of zvegf3 are also expected to exist.

The zvegf3 polynucleotide sequence disclosed herein can be used to isolate polynucleotides encoding other zvegf3 proteins. Such other polynucleotides include allelic variants, alternatively spliced cDNAs and counterpart polynucleotides from other species (orthologs). These orthologous polynucleotides can be used, inter alia, to prepare the respective orthologous proteins. Other species of interest include, but are not limited to, mammalian, avian, amphibian, reptile, fish, insect and other vertebrate and invertebrate species. Of particular interest are zvegf3 polynucleotides and proteins from other mammalian species, including non-human primate, murine, porcine, ovine, bovine, canine, feline, and equine polynucleotides and proteins. Non-human ztbg1 polypeptides and polynucleotides, as well as antagonists thereof and other related molecules, can be used, inter alia, in veterinary medicine. Orthologs of human zvegf3 can be cloned using information and compositions provided by the present invention in combination with conventional cloning techniques. For example, a cDNA can be cloned using mRNA obtained from a tissue or cell type that expresses zvegf3 as disclosed herein. Suitable sources of mRNA can be identified by probing Northern blots with probes designed from the sequences disclosed herein. A library is then prepared from mRNA of a positive tissue or cell line. A zvegf3-encoding cDNA can then be isolated by a variety of methods, such as by probing with a complete or partial human cDNA or with one or more sets of degenerate probes based on the disclosed sequences. Hybridization will generally be done under low stringency conditions, wherein washing is carried out in 1 ×SSC with an initial wash at 40° C. and with subsequent washes at 5° C. higher intervals until background is suitably reduced. A cDNA can also be cloned using the polymerase chain reaction, or PCR (Mullis, U.S. Pat. No. 4,683,202), using primers designed from the representative human zvegf3 sequence disclosed herein. Within an additional method, the cDNA library can be used to transform or transfect host cells, and expression of the cDNA of interest can be detected with an antibody to zvegf3 polypeptide. Similar techniques can also be applied to the isolation of genomic clones.

For any zvegf3 polypeptide, including variants and fusion proteins, one of ordinary skill in the art can readily generate a fully degenerate polynucleotide sequence encoding that variant using the information set forth in Tables 3 and 4, above.

Conserved regions of zvegf3, identified by alignment with sequences of other family members, can be used to identify related polynucleotides and proteins. For instance, reverse transcription-polymerase chain reaction (RT-PCR) and other techniques known in the art can be used to amplify sequences encoding the conserved motifs present in zvegf3 from RNA obtained from a variety of tissue sources. In particular, highly degenerate primers as shown below in Table 5 (designed from an alignment of zvegf3 with PDGF A and B chains, VEGF, VEGF-B, VEGF-C, and VEGF-D) are useful for cloning polynucleotides encoding homologous growth factor domains. Primers shown in Table 6, designed from an alignment of zvegf3 with *X. laevis* neuropilin precursor, human BMP-1, and *X. laevis* tolloid-like protein, are useful for cloning polynucleotides encoding CUB domains. The primers of Tables 6 and 7 can thus be used to obtain additional polynucleotides encoding homologs of the zvegf3 sequence of SEQ ID NO:1 and NO:2.

TABLE 5

| | | |
|---|---|---|
| **zvegf3 residues 279-284** | | |
| degenerate: | MGN TGY GGN GGN AAY TG | (SEQ ID NO:7) |
| consensus: | MGN TGY DSN GGN WRY TG | (SEQ ID NO:8) |
| complement: | CAR YWN CCN SHR CAN CK | (SEQ ID NO:9) |
| **zvegf3 residues 270-275** | | |
| degenerate: | TTY TGG CCN GGN TGY YT | (SEQ ID NO:10) |
| consensus: | NTN DDN CCN NSN TGY BT | (SEQ ID NO:11) |
| complement: | AVR CAN SNN GGN HHN AN | (SEQ ID NO:12) |
| **zvegf3 residues 332-337** | | |
| degenerate | CAY GAR GAR TGY GAY TG | (SEQ ID NO:13) |
| consensus: | CAY NNN NVN TGY VVN TG | (SEQ ID NO:14) |
| complement: | CAN BBR CAN BNN NNR TG | (SEQ ID NO:15) |
| **zvegf3 residues 250-255** | | |
| degenerate: | TGY ACN CCN MGN AAY TT | (SEQ ID NO:16) |
| consensus: | TGY HNN MCN MKN RMN DH | (SEQ ID NO:17) |
| complement: | DHN KYN MKN GKN NDR CA | (SEQ ID NO:18) |

TABLE 6

| | | |
|---|---|---|
| **zvegf3 residues 104-109** | | |
| consensus: | TGY AAR TAY GAY TWY GT | (SEQ ID NO:19) |
| complement: | ACR WAR TCR TAY TTR CA | (SEQ ID NO:20) |
| **zvegf3 residues 120-125** | | |
| consensus: | YWN GGN MRN TDB TGY GG | (SEQ ID NO:21) |
| complement: | CCR CAV HAN YKN CCN WR | (SEQ ID NO:22) |

TABLE 6-continued

| | | |
|---|---|---|
| **zvegf3 residues 63-68** | | |
| consensus: | TDB CCN MAN DVN TAY CC | (SEQ ID NO:23) |
| complement: | GGR TAN BHN TKN GGV HA | (SEQ ID NO:24) |

Zvegf3 polynucleotide sequences disclosed herein can also be used as probes or primers to clone 5' non-coding regions of a zvegf3 gene, including promoter sequences. These flanking sequences can be used to direct the expression of zvegf3 and other recombinant proteins. In addition, 5' flanking sequences can be used as targetting sites for regulatory constructs to activate or increase expression of endogenous zvegf3 genes as disclosed by Treco et al., U.S. Pat. No. 5,641,670.

The polynucleotides of the present invention can also be prepared by automated synthesis. The current method of choice is the phosphoramidite method. If chemically synthesized, double-stranded DNA is required, each complementary strand is made separately. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See, in general, Glick and Pastemak, *Molecular Biotechnology, Principles & Applications of Recombinant DNA*, ASM Press, Washington, D.C., 1994; Itakura et al., *Ann. Rev. Biochem.* 53: 323-56, 1984; and Climie et al., *Proc. Natl. Acad. Sci. USA* 87:633-7, 1990.

The polypeptides of the present invention, including full-length polypeptides, biologically active fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms).

Techniques for manipulating cloned DNA molecules and introducing exogenous DNA into a variety of host cells are disclosed by Sambrook et al., *Molecular Cloning: A Laboratory Manual, $2^{nd}$* ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a zvegf3 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zvegf3 polypeptide into the secretory pathway of a host cell, a secretory signal sequence (also known as a leader sequence, prepro sequence or pre sequence) is provided in the expression vector. The secretory signal sequence may be that of zvegf3, or may be derived from another secreted protein (e.g., t-PA; see, U.S. Pat. No. 5,641,655) or synthesized de novo. The secretory signal sequence is operably linked to the zvegf3 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of zvegf3 polypeptides via a host cell secretory pathway is expected to result in the production of multimeric proteins. As noted above, such multimers include both homomultimers and heteromultimers, the latter including proteins comprising only zvegf3 polypeptides and proteins including zvegf3 and heterologous polypeptides. For example, a heteromultimer comprising a zvegf3 polypeptide and a polypeptide from a related family member (e.g., VEGF, VEGF-B, VEGF-C, VEGF-D, zvegf4, PlGF, PDGF-A, or PDGF-B) can be produced by co-expression of the two polypeptides in a host cell. Sequences encoding these other family members are known. See, for example, Dvorak et al, ibid.; Olofsson et al, ibid.; Hayward et al., ibid.; Joukov et al., ibid.; Oliviero et al., ibid.; Achen et al., ibid.; Maglione et al., ibid.; Heldin et al., U.S. Pat. No. 5,219,759; and Johnsson et al., ibid. If a mixture of proteins results from expression, individual species are isolated by conventional methods. Monomers, dimers, and higher order multimers are separated by, for example, size exclusion chromatography. Heteromultimers can be separated from homomultimers by immunoaffinity chromatography using antibodies specific for individual dimers or by sequential immunoaffinity steps using antibodies specific for individual component polypeptides. See, in general, U.S. Pat. No. 5,094,941. Multimers may also be assembled in vitro upon incubation of component polypeptides under suitable conditions. In general, in vitro assembly will include incubating the protein mixture under denaturing and reducing conditions followed by refolding and reoxidation of the polypeptides to from homodimers and heterodimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Felgner et al., *Proc. Natl. Acad. Sci. USA* 84:7413-7, 1987; Mackey et al., *Proc. Natl. Acad. Sci. USA* 85:8027-31, 1988; Hawley-Nelson et al., Focus 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. Sstrong transcription promoters include promoters from SV-40 or cytomegalovirus. See, e.g., U.S. Pat. No. 4,956,288. Other suitable promoters include those from metallothionein genes (U.S. Pat. No. Nos. 4,579,821 and 4,601,978) and the adenovirus major late promoter. Expression vectors for use in mammalian cells include pZP-1 and pZP-9, which have been deposited with the American Type Culture Collection, Rockville, Md. USA under accession numbers 98669 and 98668, respectively.

Drug selection is generally used to select for cultured mammalian cells into which foreign DNA has been inserted. Such cells are commonly referred to as “transfectants”. Cells that have been cultured in the presence of the selective agent and are able to pass the gene of interest to their progeny are referred to as “stable transfectants.” An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as “amplification.” Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase can be used to sort transfected cells from untransfected cells by such means as FACS sorting or magnetic bead separation technology.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566-4579, 1993). This system, which utilizes transfer vectors, is commercially available in kit form (Bac-to-Bac™ kit; Life Technologies, Rockville, Md.). The transfer vector (e.g., pFastBac1 ™; Life Technologies) contains a Tn7 transposon to move the DNA encoding the protein of interest into a baculovirus genome maintained in *E. coli* as a large plasmid called a “bacmid.” See, Hill-Perkins and Possee, *J.Gen. Virol.* 71:971-976, 1990; Bonning et al., *J.Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a zvegf3-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zvegf3 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or Trichoplusia ni (e.g., High Five™ cells; Invitrogen, Carlsbad, Calif.). See, in general, Glick and Pastemak, *Molecular Biotechnology: Principles and Applications of Recombinant DNA*, ASM Press, Washington, D.C., 1994. See also, U.S. Pat. No. 5,300,435. Serum-free media are used to grow and maintain the cells. Suitable media formulations are known in the art and can be obtained from commercial suppliers. The cells are grown up from an inoculation density of approximately 2-5×$10^5$ cells to a density of 1-2×$10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii and Candida maltosa* are known in the art. See, for example, Gleeson et al., *J. Gen. Microbiol.* 132:3459-3465, 1986; Cregg, U.S. Pat. No. 4,882,279; and Raymond et al., *Yeast* 14, 11-23, 1998. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. No. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zvegf3 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Production of zvegf3 fusion proteins in prokaryotic host cells is of particular interest. An exemplary such fusion protein comprises a zvegf3 polypeptide fused to maltose binding protein. Such fusions may further comprise additional sequences, such as polyhistidine to provide for affinity purification of the polypeptide fusion. An enzymatic cleavage site (e.g., a thrombin cleavage site) may also be included to allow for separation of zvegf3 and non-zvegf3 components of the fusion.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells, for example, are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors.

Zvegf3 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* ($2^{nd}$ edition), Pierce Chemical Co., Rockford, Ill., 1984; Bayer and Rapp, Chem. Pept. Prot. 3:3, 1986; and Atherton et al., *Solid Phase Peptide Synthesis: A Practical Approach*, IRL Press, Oxford, 1989.

Non-covalent complexes comprising a zvegf3 polypeptide can be prepared by incubating a zvegf3 polypeptide and a second polypeptide (e.g., a zvegf3 polypeptide or another peptide of the PDGF/NVEGF family) at near-physiological pH. In a typical reaction, polypeptides at a concentration of about 0.1-0.5 μg/μl are incubated at pH≈z7.4 in a weak buffer (e.g., 0.01 M phosphate or acetate buffer); sodium chloride may be included at a concentration of about 0.1 M. At 37° C. the reaction is essentially complete with 4-24 hours. See, for example, Weintraub et al., *Endocrinology* 101:225-235, 1997.

Covalent complexes can also be made by isolating the desired component polypeptides and combining them in vitro. Covalent complexes that can be prepared in this manner include homodimers of zvegf3 polypeptides, heterodimers of two different zvegf3 polypeptides, and heterodimers of a zvegf3 polypeptide and a polypeptide from another family member of the VEGF/PDGF family of proteins. The two polypeptides are mixed together under denaturing and reducing conditions, followed by renaturation of the proteins by removal of the denaturants. Removal can be done by, for example, dialysis or size exclusion chromatography to provide for buffer exchange. When combining two different polypeptides, the resulting renaturated proteins may form homodimers of the individual components as well as heterodimers of the two polypeptide components. See, Cao et al., *J. Biol. Chem.* 271:3154-3162, 1996.

Depending upon the intended use, polypeptides and proteins of the present invention can be purified to >80% purity, to >90% purity, to >95% purity, or to a pharmaceutically pure state, that is greater than 99.9% pure with respect to contaminating macromolecules, particularly other proteins and nucleic acids, and free of infectious and pyrogenic agents.

Expressed recombinant zvegf3 proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Furthermore, the growth factor domain itself binds to nickel resin at pH 7.0-8.0 and 25 mM Na phosphate, 0.25 M NaCl. Bound protein can be eluted with a descending pH gradient down to pH 5.0 or an imidazole gradient. Proteins comprising a glu-glu tag can be purified by immunoaffinity chromatography according to conventional procedures. See, for example, Grussenmeyer et al., ibid. Maltose binding protein fusions are purified on an amylose column according to methods known in the art. As disclosed in more detail below, zvegf3 growth factor domain protein can be purified using a combination of chromatography on a strong cation exchanger followed by hydrophobic interaction chromatography. When the protein is produced in BHK cells, insulin-like growth factor binding protein 4 (IGFBP4) co-purifies with the zvegf3 under these conditions. Further purification can be obtained using reverse-phase HPLC, anion exchange on a quaternary amine strong cation exchanger at low ionic strength and pH from 7.0 to 9.0, or hydrophobic interaction chromatography on a phenyl ether resin. It has also been found that zvegf3 binds to various dye matrices (e.g., BLUE1, BLUE 2, ORANGE 1, ORANGE 3, and RED3 from Lexton Scientific, Signal Hill, Calif.) in PBS at pH 6-8, from which the bound protein can be eluted in 1-2M NaCl in 20 mM boric acid buffer at pH 8.8. Protein eluted from RED3 may be passed over RED2 (Lexton Scientific) to remove remaining contaminants.

Using methods known in the art, zvegf3 proteins can be prepared as monomers or multimers; glycosylated or non-glycosylated; pegylated or non-pegylated; and may or may not include an initial methionine amino acid residue.

The invention further provides polypeptides that comprise an epitope-bearing portion of a protein as shown in SEQ ID NO:2. An "epitope" is a region of a protein to which an antibody can bind. See, for example, Geysen et al., *Proc. Natl. Acad. Sci. USA* 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660-666, 1983. Antibodies that recognize short, linear epitopes are particularly useful in analytic and diagnostic applications that employ denatured protein, such as Western blotting (Tobin, *Proc. Natl. Acad. Sci. USA* 76:4350-4356, 1979). Antibodies to short peptides may also recognize proteins in native conformation and will thus be useful for monitoring protein expression and protein isolation, and in detecting zvegf3 proteins in solution, such as by ELISA or in immunoprecipitation studies.

Antigenic, epitope-bearing polypeptides of the present invention are useful for raising antibodies, including monoclonal antibodies, that specifically bind to a zvegf3 protein. Antigenic, epitope-bearing polypeptides contain a sequence of at least six, often at least nine, more often from 15 to about 30 contiguous amino acid residues of a zvegf3 protein (e.g., SEQ ID NO:2). Polypeptides comprising a larger portion of a zvegf3 protein, i.e. from 30 to 50 residues up to the entire sequence are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Such regions include residues 43-48, 96-101, 97-102, 260-265, and 330-335 of SEQ ID NO:2. As noted above, it is generally preferred to use somewhat longer peptides as immunogens, such as a peptide comprising residues 80-104, 299-314, and 299-326 of SEQ ID NO:2. The latter peptide can be prepared with an additional N-terminal cys residue to facilitate coupling.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

Methods for preparing and isolating polyclonal and monoclonal antibodies are well known in the art. See, for example, Cooligan, et al. (eds.), *Current Protocols in Immunology*, National Institutes of Health, John Wiley and Sons, Inc., 1995; Sambrook et al., *Molecular Cloning: A Laboratory Manual*, second edition, Cold Spring Harbor, N.Y., 1989; and Hurrell, J. G. R. (ed.), *Monoclonal Hybridoma Antibodies: Techniques and Applications*, CRC Press, Inc., Boca Raton, Fla., 1982. As would be evident to one of ordinary skill in the art, polyclonal antibodies can be generated from inoculating a variety of warm-blooded animals such as horses, cows, goats, sheep, dogs, chickens, rabbits, mice, and rats with a zvegf3 polypeptide or a fragment thereof. The immunogenicity of a zvegf3 polypeptide may be increased through the use of an adjuvant, such as alum (aluminum hydroxide) or Freund's complete or incomplete adjuvant. Polypeptides useful for immunization also include fusion polypeptides, such as fusions of zvegf3 or a portion thereof with an immunoglobulin polypeptide or with maltose binding protein. If the polypeptide portion is "hapten-like", such portion may be advantageously joined or linked to a macromolecular carrier (such as keyhole limpet hemocyanin (KLH), bovine serum albumin (BSA), or tetanus toxoid) for immunization.

Alternative techniques for generating or selecting antibodies include in vitro exposure of lymphocytes to zvegf3 protein or peptide, and selection of antibody display libraries in phage or similar vectors (for instance, through use of immobilized or labeled zvegf3 protein or peptide). Techniques for creating and screening such random peptide display libraries are known in the art (Ladner et al., US Pat. No. 5,223,409; Ladner et al., U.S. Pat. No. 4,946,778; Ladner et al., U.S. Pat. No. 5,403,484 and Ladner et al., U.S. Pat. No. 5,571,698), and random peptide display libraries and kits for screening such libraries are available commercially, for instance from Clontech Laboratories (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zvegf3 sequences disclosed herein to identify proteins which bind to zvegf3. These "binding proteins", which interact with zvegf3 polypeptides, can be used for tagging cells or for isolating homologous polypeptides by affinity purification, or they can be directly or indirectly conjugated to drugs, toxins, radionuclides, and the like. These binding proteins can also be used in analytical methods, such as for screening expression libraries and neutralizing activity; within diagnostic assays, such as for determining circulating levels of polypeptides; for detecting or quantitating soluble polypeptides as markers of underlying pathology or disease; and as zvegf3 antagonists to block zvegf3 binding and signal transduction in vitro and in vivo.

Antibodies are determined to be specifically binding if they bind to a zvegf3 polypeptide, peptide or epitope with an affinity at least 10-fold greater than the binding affinity to control (non-zvegf3) polypeptide or protein. In this regard, a "non-zvegf3 polypeptide" includes the related molecules VEGF, VEGF-B, VEGF-C, VEGF-D, PIGF, PDGF-A, and PDGF-B, but excludes zvegf3 polypeptides from non-human species. Due to the high level of amino acid sequence identity expected between zvegf3 orthologs, antibodies specific for human zvegf3 may also bind to zvegf3 from other species. The binding affinity of an antibody can be readily determined by one of ordinary skill in the art, for example, by Scatchard analysis (Scatchard, G., Ann. *NY Acad. Sci.* 51: 660-672, 1949). Methods for screening and isolating specific antibodies are well known in the art. See, for example, Paul (ed.), *Fundamental Immunology, Raven Press,* 1993; Getzoff et al., *Adv. in Immunol.* 43:1-98, 1988;Goding, J.W. (ed.), *Monoclonal Antibodies: Principles and Practice*, Academic Press Ltd., 1996;Benjamin et al., *Ann. Rev. Immunol.* 2:67-101, 1984.

A variety of assays known to those skilled in the art can be utilized to detect antibodies which specifically bind to zvegf3 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zvegf3 protein or polypeptide.

Antibodies to zvegf3 may be used for tagging cells that express zvegf3; for isolating zvegf3 by affinity purification; for diagnostic assays for determining circulating levels of zvegf3 polypeptides; for detecting or quantitating soluble zvegf3 as a marker of underlying pathology or disease; in analytical methods employing FACS; for screening expression libraries; for generating anti-idiotypic antibodies; and as neutralizing antibodies or as antagonists to block zvegf3 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies may also be directly or indirectly conjugated to drugs, toxins, radionuclides and the like, and these conjugates used for in vivo diagnostic or therapeutic applications. Moreover, antibodies to zvegf3 or fragments thereof may be used in vitro to detect denatured zvegf3 or fragments thereof in assays, for example, Western Blots or other assays known in the art. Antibodies can also be used to target an attached therapeutic or diagnostic moiety to cells expressing zvegf3 or receptors for zvegf3.

For some applications (e.g., certain therapeutic applications) it is preferred to use neutralizing antibodies. As used herein, the term "neutralizing antibody" denotes an antibody that inhibits at least 50% of the biological activity of the cognate antigen when the antibody is added at a 1000-fold molar access. Those of skill in the art will recognize that greater neutralizing activity is sometimes desirable, and antibodies that provide 50% inhibition at a 100-fold or 10-fold molar access may be advantageously employed.

Activity of zvegf3 proteins and antagonists thereof can be measured in vitro using cultured cells or in vivo by administering molecules of the claimed invention to an appropriate animal model. Target cells for use in zvegf3 activity assays include vascular cells (especially endothelial cells and smooth muscle cells), hematopoietic (myeloid and lymphoid) cells, liver cells (including hepatocytes, fenestrated endothelial cells, Kupffer cells, and Ito cells), fibroblasts (including human dermal fibroblasts and lung fibroblasts), neurite cells (including astrocytes, glial cells, dendritic cells, and PC-12 cells), Schwann cells, fetal lung cells, articular synoviocytes, pericytes, chondrocytes, oligodendrocytes, osteoblasts, and other cells expressing PDGF alpha receptors.

Zvegf3 proteins can be analyzed for receptor binding activity by a variety of methods well known in the art, including receptor competition assays (Bowen-Pope and Ross, *Methods Enzymol.* 109:69-100, 1985), use of soluble receptors, and use of receptors produced as IgG fusion proteins (U.S. Pat. No. 5,750,375). Receptor binding assays can be performed on cell lines that contain known cell-surface receptors for evaluation. The receptors can be naturally present in the cell, or can be recombinant receptors expressed by genetically engineered cells. Cell types that are able to bind zvegf3 can be identified through the use of zvegf3-toxin conjugates, such as conjugates of a zvegf3 protein and saporin. Binding of the zvegf3-toxin conjugate by cells, either in tissue culture, in organ cultures, or in vivo settings will allow for the incorporation of the conjugate into the cell. Once inside the cell saporin has a toxic effect on the cell, thereby killing it. This activity can be used to identify cell types that are able to bind and internalize zvegf3. In addition to allowing for the identification of responsive cell types, toxin conjugates can be used in in vivo studies to identify organs and tissues where zvegf3 has a biological activity by looking for pathology within the animal following injection of the conjugate.

Activity of zvegf3 proteins can be measured in vitro using cultured cells. Mitogenic activity can be measured using known assays, including $^3$H-thymidine incorporation assays (as disclosed by, e.g., Raines and Ross, *Methods Enzymol.* 109:749-773, 1985 and Wahl et al., *Mol. Cell Biol.* 8:5016-5025, 1988), dye incorporation assays (as disclosed by, for example, Mosman, *J. Immunol. Meth.* 65:55-63, 1983 and Raz et al., *Acta Trop.* 68:139-147, 1997) or cell counts. Suitable mitogenesis assays measure incorporation of $^3$H-thymidine into (1) 20% confluent cultures to look for the ability of zvegf3 proteins to further stimulate proliferating cells, and (2) quiescent cells held at confluence for 48 hours to look for the ability of zvegf3 proteins to overcome contact-induced growth inhibition. Suitable dye incorporation assays include measurement of the incorporation of the dye Alamar blue (Raz et al., ibid.) into target cells. See also, Gospodarowicz et al., *J. Cell. Biol.* 70:395-405, 1976; Ewton and Florini, *Endocrinol.* 106:577-583, 1980;and Gospodarowicz et al., *Proc. Natl. Acad. Sci. USA* 86:7311-7315, 1989. Cell differentiation can be assayed using suitable precursor cells that can be induced to differentiate into a more mature phenotype. For example, endothelial cells and hematopoietic cells are derived from a common ancestral cell, the hemangioblast (Choi et al., *Development* 125:725-732, 1998). Mesenchymal stem cells can also be used to measure the ability of zvegf3 protein to stimulate differentiation into osteoblasts. Differentiation is indicated by the expression of osteocalcin, the ability of the cells to mineralize, and the expression of alkaline phosphatase, all of which can be measured by routine methods known in the art. Effects of zvegf3 proteins on tumor cell growth and metastasis can be analyzed using the Lewis lung carcinoma model, for example as described by Cao et al., *J.Exp. Med.* 182:2069-2077, 1995. Activity of zvegf3 proteins on cells of neural origin can be analyzed using assays that measure effects on neurite growth.

Zvegf3 activity may also be detected using assays designed to measure zvegf3-induced induced production of one or more additional growth factors or other macromolecules. Such assays include those for determining the presence of hepatocyte growth factor (HGF), epidermal growth factor (EGF), transforming growth factor alpha (TGF$\alpha$), interleukin-6 (IL-6), VEGF, acidic fibroblast growth factor (aFGF), and angiogenin. Suitable assays include mitogenesis assays using target cells responsive to the macromolecule of interest, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a zvegf3 protein is measured using zymogram gels (Loita and Stetler-Stevenson, *Cancer Biology* 1:96-106, 1990). Procollagen/collagen synthesis by dermal fibroblasts and chondrocytes in response to a test protein is measured using $^3$H-proline incorporation into nascent secreted collagen. $^3$H-labeled collagen is visualized by SDS-PAGE followed by autoradiography (Unemori and Amento, *J. Biol. Chem.* 265: 10681-10685, 1990). Glycosaminoglycan (GAG) secretion from dermal fibroblasts and chondrocytes is measured using a 1,9-dimethylmethylene blue dye binding assay (Famdale et al., *Biochim. Biophys. Acta* 883:173-177, 1986). Collagen and GAG assays are also carried out in the presence of IL-1$\beta$ or TGF-$\beta$ to examine the ability of zvegf3 protein to modify the established responses to these cytokines.

Monocyte activation assays are carried out (1) to look for the ability of zvegf3 proteins to further stimulate monocyte activation, and (2) to examine the ability of zvegf3 proteins to modulate attachment-induced or endotoxin-induced monocyte activation (Fuhlbrigge et al., *J. Immunol.* 138: 3799-3802, 1987). IL-1$\beta$ and TNF$\alpha$ levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

Hematopoietic activity of zvegf3 proteins can be assayed on various hematopoietic cells in culture. Suitable assays include primary bone marrow or peripheral blood leukocyte colony assays, and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of zvegf3 polypeptides on hematopoietic cell lines can be measured using $^3$H-thymidine incorporation assays, dye incorporation assays, or cell counts (Raines and Ross, *Methods Enzymol.* 109:749-773, 1985 and Foster et al., U.S. Pat. No. 5,641,655). For example, cells are cultured in multi-well microtiter plates. Test samples and $^3$H-thymidine are added, and the cells are incubated overnight at 37° C. Contents of the wells are transferred to filters, dried, and counted to determine incorporation of label. Cell proliferation can also be measured using a colorimetric assay based on the metabolic breakdown of 3-(4,5-dimethylthiazol-2-yl)-2,5-diphenyl tetrazolium bromide (MTT) (Mosman, ibid.). Briefly, a solution of MTT is added to 100 μl of assay cells, and the cells are incubated at 37° C. After 4 hours, 200 μl of 0.04 N HCl in isopropanol is added, the solution is mixed, and the absorbance of the sample is measured at 570 nm.

Cell migration is assayed essentially as disclosed by Kahler et al. (*Arteriosclerosis, Thrombosis, and Vascular Biology* 17:932-939, 1997). A protein is considered to be chemotactic if it induces migration of cells from an area of low protein concentration to an area of high protein concentration. The assay is performed using modified Boyden chambers with a polystryrene membrane separating the two chambers (Transwell; Coming Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve.

Smooth muscle cell (SMC) migration can be measured in the aortic explant assay of Kenagy et al. (*Circulation* 96:3555-3560, 1997). In a typical protocol, explants are prepared from baboon thoracic aortas, and the inner media is isolated and chopped into 1-mm$^2$ pieces. The explants are placed in tissue culture flasks containing DMEM supplemented with 5 μg/ml transferrin, 6 μg/ml insulin, 1 mg/ml ovalbumin, and the test compound. The number of migrating cells is determined daily.

Cell adhesion activity is assayed essentially as disclosed by LaFleur et al. (*J. Biol. Chem.* 272:32798-32803, 1997). Briefly, microtiter plates are coated with the test protein, non-specific sites are blocked with BSA, and cells (such as smooth muscle cells, leukocytes, or endothelial cells) are plated at a density of approximately $10^4$-$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

Assays for angiogenic activity are also known in the art. For example, the effect of zvegf3 proteins on primordial endothelial cells in angiogenesis can be assayed in the chick chorioallantoic membrane angiogenesis assay (Leung, *Science* 246:1306-1309, 1989; Ferrara, *Ann. NY Acad. Sci.* 752: 246-256, 1995). Briefly, a small window is cut into the shell of an eight-day old fertilized egg, and a test substance is applied to the chorioallantoic membrane. After 72 hours, the membrane is examined for neovascularization. Other suitable assays include microinjection of early stage quail (Coturnix coturnix japonica) embryos as disclosed by Drake et al. (*Proc. Natl. Acad. Sci. USA* 92:7657-7661, 1995); the rodent model of corneal neovascularization disclosed by Muthukkaruppan and Auerbach (*Science* 205:1416-1418, 1979), wherein a test substance is inserted into a pocket in the cornea of an inbred mouse; and the hamster cheek pouch assay (Höckel et al., *Arch. Surg.* 128:423-429, 1993). Induction of vascular permeability, which is indicative of angiogenic activity, is measured in assays designed to detect leakage of protein from the vasculature of a test animal (e.g., mouse or guinea pig) after administration of a test compound (Miles and Miles, *J. Physiol.* 118:228-257, 1952;Feng et al., *J. Exp. Med.* 183:1981-1986, 1996). In vitro assays for angiogenic activity include the tridimensional collagen gel matrix model (Pepper et al. *Biochem. Biophys. Res. Comm.* 189:824-831, 1992 and Ferrara et al., *Ann. NY Acad. Sci.* 732:246-256, 1995), which measures the formation of tube-like structures by microvascular endothelial cells; and matrigel models (Grant et al., "Angiogenesis as a component of epithelial-mesenchymal interactions" in Goldberg and Rosen, *Epithelial-Mesenchymal Interaction in Cancer, Birkhäuser Verlag,* 1995, 235-248; Baatout, *Anticancer Research* 17:451-456, 1997), which are used to determine effects on cell migration and tube formation by endothelial cells seeded in matrigel, a basement membrane extract enriched in laminin. Angiogenesis assays can be carried out in the presence and absence of VEGF to assess possible combinatorial effects. VEGF can be used as a control within in vivo assays.

Zvegf3 activity can also be measured using assays that measure axon guidance and growth. Of particular interest are assays that indicate changes in neuron growth patterns, for example those disclosed in Hastings, WIPO Publication WO 97/29189 and Walter et al., *Development* 101:685-96, 1987. Assays to measure the effects on neuron growth are well known in the art. For example, the C assay (e.g., Raper and Kapfhammer, *Neuron* 4:21-9, 1990 and Luo et al., *Cell* 75:217-27, 1993) can be used to determine collapsing activity of zvegf3 on growing neurons. Other methods that can assess zvegf3-induced effects on neurite extension are also known. See, Goodman, *Annu. Rev. Neurosci.* 19:341-77, 1996. Conditioned media from cells expressing a zvegf3 protein, a zvegf3 agonist, or a zvegf3 antagonist, or aggregates of such cells, can by placed in a gel matrix near suitable neural cells, such as dorsal root ganglia (DRG) or sympathetic ganglia explants, which have been co-cultured with nerve growth factor. Compared to control cells, zvegf3-induced changes in neuron growth can be measured (as disclosed by, for example, Messersmith et al., *Neuron* 14:949-59, 1995 and Puschel et al., *Neuron* 14:941-8, 1995). Likewise neurite outgrowth can be measured using neuronal cell suspensions grown in the presence of molecules of the present invention. See, for example, O'Shea et al., *Neuron* 7:231-7, 1991 and DeFreitas et al., *Neuron* 15:333-43, 1995.

The biological activities of zvegf3 proteins can be studied in non-human animals by administration of exogenous protein, by expression of zvegf3-encoding polynucleotides, and by suppression of endogenous zvegf3 expression through antisense or knock-out techniques. Zvegf3 proteins can be administered or expressed individually, in combination with other zvegf3 proteins, or in combination with non-vegf3 proteins, including other growth factors (e.g., other VEGFs, PlGFs, or PDGFs). For example, a combination of zvegf3 polypeptides (e.g., a combination of $zvegf3_{15-163}$, $zvegf3_{15-230}$, and $zvegf3_{235-345}$) can be administered to a test animal or expressed in the animal. Test animals are monitored for changes in such parameters as clinical signs, body weight, blood cell counts, clinical chemistry, histopathology, and the like.

Effects of zvegf3 and zvegf3 antagonists on liver and kidney fibrosis can be tested in known animal models, such as the db/db mouse model disclosed by Cohen et al., *Diabetologia* 39:270-274, 1996 and Cohen et al., *J. Clin. Invest.* 95:2338-2345, 1995 or transgenic animal models (Imai et al., *Contrib. Nephrol.* 107:205-215, 1994).

Effects on fibrosis can also be assayed in a mouse model using bleomycin. The chemotherapy agent bleomycin is a known causative agent of pulmonary fibrosis in humans and can induce interstitial lung disease in mice, including an increase in the number of fibroblasts, enhanced collagen deposition, and dysregulated matrix remodeling. C57B1/6 mice are administered bleomycin by osmotic minipump for 1 week. There follows a period of inflammation, with cutaneous toxicity beginning approximately 4-7 days after bleomycin administration and continuing for about a week, after which the mice appear to regain health. About 3-4 weeks after the finish of bleomycin delivery, the mice are sacrificed, and the lungs are examined histologically for signs of fibrosis. Scoring is based on the extent of lung fibrotic lesions and their severity. Serum is assayed for lactic dehydrogenase, an intracellular enzyme that is released into the circulation upon general cell death or injury. Lung tissue is assayed for hydroxyproline as a measure of collagen deposition.

Stimulation of coronary collateral growth can be measured in known animal models, including a rabbit model of peripheral limb ischemia and hind limb ischemia and a pig model of chronic myocardial ischemia (Ferrara et al., *Endocrine Reviews* 18:4-25, 1997). Zvegf3 proteins are assayed in the presence and absence of VEGFs, angiopoietins, and basic FGF to test for combinatorial effects. These models can be modified by the use of adenovirus or naked DNA for gene delivery as disclosed in more detail below, resulting in local expression of the test protein(s).

Efficacy of zvegf3 polypeptides in promoting wound healing can be assayed in animal models. One such model is the linear skin incision model of Mustoe et al. (*Science* 237:1333, 1987). In a typical procedure, a 6-cm incision is made in the dorsal pelt of an adult rat, then closed with wound clips. Test substances and controls (in solution, gel, or powder form) are applied before primary closure. Administration will often be limited to a single application, although additional applications can be made on succeeding days by careful injection at several sites under the incision. Wound breaking strength is evaluated between 3 and 21 days post wounding. In a second model, multiple, small, full-thickness excisions are made on the ear of a rabbit. The cartilage in the ear splints the wound, removing the variable of wound contraction from the evaluation of closure. Experimental treatments and controls are applied. The geometry and anatomy of the wound site allow for reliable quantification of cell ingrowth and epithelial migration, as well as quantitative analysis of the biochemistry of the wounds (e.g., collagen content). See, Mustoe et al., *J. Clin. Invest.* 87:694, 1991. The rabbit ear model can be modified to create an ischemic wound environment, which more closely resembles the clinical situation (Ahn et al., *Ann. Plast. Surg.* 24:17, 1990). Within a third model, healing of partial-thickness skin wounds in pigs or guinea pigs is evaluated (LeGrand et al., *Growth Factors* 8:307, 1993). Experimental treatments are applied daily on or under dressings. Seven days after wounding, granulation tissue thickness is determined. This model is particularly useful for dose-response studies, as it is more quantitative than other in vivo models of wound healing. A full thickness excision model can also be employed. Within this model, the epidermis and dermis are removed down to the panniculus carnosum in rodents or the subcutaneous fat in pigs. Experimental treatments are applied topically on or under a dressing, and can be applied daily if desired. The wound closes by a combination of contraction and cell ingrowth and proliferation. Measurable endpoints include time to wound closure, histologic score, and biochemical parameters of wound tissue. Impaired wound healing models are also known in the art (e.g., Cromack et al., *Surgery* 113:36, 1993; Pierce et al., *Proc. Natl. Acad. Sci. USA* 86:2229, 1989; Greenhalgh et al., *Amer. J. Pathol.* 136:1235, 1990). Delay or prolongation of the wound healing process can be induced pharmacologically by treatment with steroids, irradiation of the wound site, or by concomitant disease states (e.g., diabetes). Linear incisions or full-thickness excisions are most commonly used as the experimental wound. Endpoints are as disclosed above for each type of wound. Subcutaneous implants can be used to assess compounds acting in the early stages of wound healing (Broadley et al., *Lab. Invest.* 61:571, 1985; Sprugel et al., *Amer. J. Pathol.* 129: 601, 1987). Implants are prepared in a porous, relatively non-inflammatory container (e.g., polyethylene sponges or expanded polytetrafluoroethylene implants filled with bovine collagen) and placed subcutaneously in mice or rats. The interior of the implant is empty of cells, producing a "wound space" that is well-defined and separable from the preexisting tissue. This arrangement allows the assessment of cell influx and cell type as well as the measurement of vasculogenesis/angiogenesis and extracellular matrix production.

Expression of zvegf3 proteins in animals provides models for study of the biological effects of overproduction or inhibition of protein activity in vivo. Zvegf3-encoding polynucleotides can be introduced into test animals, such as mice, using viral vectors or naked DNA, or transgenic animals can be produced. In general, a zvegf3 protein is expressed with a secretory peptide. Suitable secretory peptides include the zvegf3 secretory peptide (e.g., residues 1-14 of SEQ ID NO:2) and heterologous secretory peptides. An exemplary heterologous secretory peptide is that of human tissue plasminogen activator (t-PA). The t-PA secretory peptide may be modified to reduce undesired proteolytic cleavage as disclosed in U.S. Pat. No. 5,641,655.

Proteins of the present invention can be assayed in vivo using viral delivery systems. Exemplary viruses include adenovirus, herpesvirus, retroviruses, vaccinia virus, and adeno-associated virus (AAV). For review, see Becker et al., *Meth. Cell Biol.* 43:161-89, 1994; and Douglas and Curiel, *Science & Medicine* 4:44-53, 1997. Adenovirus (reviewed by Becker et al., *Meth. Cell Biol.* 43:161-89, 1994; and Douglas and Curiel, *Science & Medicine* 4:44-53, 1997) offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined. Adenoviral vectors containing various deletions of viral genes can be used in an attempt to reduce or eliminate immune responses to the vector. Such adenoviruses are E1 deleted, and in addition contain deletions of E2A or E4 (Lusky et al., *J. Virol.* 72:2022-2032, 1998; Raper et al., *Human Gene Therapy* 9:671-679, 1998). In addition, deletion of E2b is reported to reduce immune responses (Amalfitano, et al., *J. Virol.* 72:926-933, 1998). Generation of so-called "gutless" adenoviruses where all viral transcription units are deleted is particularly advantageous for insertion of large inserts of heterologous DNA. For review, see Yeh and Perricaudet, *FASEB J.* 11:615-623, 1997. Retroviral vectors are disclosed, for example, by Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO publication WO 95/07358; and Kuo et al., *Blood* 82:845, 1993.

In an alternative method, a vector can be introduced by liposome-mediated transfection, a technique that provides certain practical advantages, including the molecular targeting of liposomes to specific cells. Directing transfection to particular cell types is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Within another embodiment target cells are removed from the animal, and DNA is introduced as a naked DNA plasmid. The transformed cells are then re-implanted into the body of the animal. Naked DNA vectors can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Mice engineered to express the zvegf3 gene, referred to as "transgenic mice," and mice that exhibit a complete absence of zvegf3 gene function, referred to as "knockout mice," can also be generated (Snouwaert et al., *Science* 257:1083, 1992; Lowell et al., *Nature* 366:740-42, 1993; Capecchi, *Science* 244:1288-1292, 1989; Palmiter et al., *Ann. Rev. Genet.* 20:465-499, 1986). Transgenesis experiments can be performed using normal mice or mice with genetic disease or other altered phenotypes. Transgenic mice that over-express zvegf3, either ubiquitously or under a tissue-specific or tissue-restricted promoter, can be used to determine whether or not over-expression causes a phenotypic change. Suitable promoters include metallothionein, albumin (Pinkert et al., *Genes Dev.* 1(3):268-76, 1987), and K-14 keratinocyte (Vassar et al., *Proc. Natl. Acad. Sci. USA* 86(5): 1563-1567, 1989) gene promoters. The metallothionein-1 (MT-1) promoter provides expression in liver and other tissues, often leading to high levels of circulating protein. Over-expression of a wild-type zvegf3 polypeptide, polypeptide fragment or a mutant thereof may alter normal cellular processes, resulting in a phenotype that identifies a tissue in which zvegf3 expression is functionally relevant and may indicate a therapeutic target for the zvegf3, its agonists or antagonists. For example, a transgenic mouse can be engineered to over-express a full-length zvegf3 sequence, which may result in a phenotype that shows similarity with human diseases. Similarly, knockout zvegf3 mice can be used to determine where zvegf3 is absolutely required in vivo. The phenotype of knockout mice is predictive of the in vivo effects of zvegf3 antagonists. Knockout mice can also be used to study the effects of zvegf3 proteins in models of disease, including, for example, cancer, atherosclerosis, rheumatoid arthritis, ischemia, and cardiovascular disease. The human zvegf3 cDNA can be used to isolate murine zvegf3 mRNA, cDNA and genomic DNA as disclosed above, which are subsequently used to generate knockout mice. These mice may be employed to study the zvegf3 gene and the protein encoded thereby in an in vivo system, and can be used as in vivo models for corresponding human diseases. Moreover, transgenic mice expressing zvegf3 antisense polynucleotides or ribozymes directed against zvegf3, described herein, can be used analogously to knockout mice described above.

The functional relationship between zvegf3 and PDGF ligands can be investigated through knockin experiments. For example, the PDGF A or PDGF B gene in an animal can be replaced by knocking a zvegf3 gene or cDNA into the genomic locus of a PDGF ligand in embryonic stem (ES) cells, which are then used to generate the knockin mice, in which zvegf3 protein is expressed by the (replaced) PDGF genomic locus. Such knockin mice can be used to address a number of questions, such as whether zvegf3 can substitute PDGF function during development; whether zvegf3 has unique functions; and, using cell lines established from the mice, the mechanism of zvegf3 signal transduction. See, for example, Wang et al., *Development* 124:2507-2513, 1997; Zhuang et al., *Mol. Cell Biol.* 18:3340-3349. 1998; Geng et al., *Cell* 97:767-777, 1999. In a further application of this technology, individual domains of zvegf3 can be specifically deleted or modified by knocking in a modified zvegf3 sequence or a specific spliced version of zvegf3, thereby providing a transgenic model for the study of functional domains of the protein. See, for example, Zhuang et al. (ibid.) and Baudoin et al. (*Genes Dev.* 12:1202-1216, 1998). In another application, tissues and cell types that express the zvegf3 gene can be identified by knockin of a sensitive reporter gene (e.g., LacZ) into the zvegf3 locus. See, for example, Monroe et al., *Immunity* 11:201-212, 1999; Zhuang et al., ibid.; Geng et al., ibid.

Antisense methodology can be used to inhibit zvegf3 gene transcription to examine the effects of such inhibition in vivo. Polynucleotides that are complementary to a segment of a zvegf3 -encoding polynucleotide (e.g., a polynucleotide as set froth in SEQ ID NO:1) are designed to bind to zvegf3 -encoding mRNA and to inhibit translation of such mRNA. Such antisense oligonucleotides can also be used to inhibit expression of zvegf3 polypeptide-encoding genes in cell culture.

Those skilled in the art will recognize that the assays disclosed herein can be readily adapted to study the activity of zvegf3 proteins, anti-zvegf3 antibodies and other antagonists, and test substances derived from a variety of sources.

Zvegf3 proteins may be used therapeutically to stimulate tissue development or repair, or cellular differentiation or proliferation. Zvegf3 has been found to bind to PDGF alpha receptor and to stimulate alpha receptor-mediated cellular processes. Zvegf3 also binds to the PDGF beta receptor in the presence of the alpha receptor. Zvegf3 thus binds to the $\alpha\alpha$ and $\alpha\beta$ isoforms of PDGF receptor. The protein can therefore be used as a PDGF alpha receptor agonist. Specific applications include, without limitation: the treatment of full-thickness skin wounds, including venous stasis ulcers and other chronic, non-healing wounds, particularly in cases of compromised wound healing due to diabetes mellitus, connective tissue disease, smoking, bums, and other exacerbating conditions; fracture repair; skin grafting; within reconstructive surgery to promote neovascularization and increase skin flap survival; to establish vascular networks in transplanted cells and tissues, such as transplanted islets of Langerhans; to treat female reproductive tract disorders, including acute or chronic placental insufficiency (an important factor causing perinatal morbidity and mortality) and prolonged bleeding; to promote the growth of tissue damaged by periodontal disease; to promote the repair of damaged liver tissue; in the treatment of acute and chronic lesions of the gastrointestinal tract, including duodenal ulcers, which are characterized by a deficiency of microvessels; to promote angiogenesis and prevent neuronal degeneration due to chronic cerebral ischemia; to accelerate the formation of collateral blood vessels in ischemic limbs; to promote vessel repair and development of collateral circulation following myocardial infarction so as to limit ischemic injury; and to stimulate hematopoiesis. The polypeptides are also useful additives in tissue adhesives for promoting revascularization of the healing tissue.

Of particular interest is the use of zvegf3 or zvegf3 antagonists for the treatment or repair of liver damage, including damage due to chronic liver disease, including chronic active hepatitis (including hepatitis C) and many other types of cirrhosis. Widespread, massive necrosis, including destruction of virtually the entire liver, can be caused by, inter alia, fulminant viral hepatitis; overdoses of the analgesic acetaminophen; exposure to other drugs and chemicals such as halothane, monoamine oxidase inhibitors, agents employed in the treatment of tuberculosis, phosphorus, carbon tetrachloride, and other industrial chemicals. Conditions associated with ultrastructural lesions that do not necessarily produce obvious liver cell necrosis include Reye's syndrome in children, tetracycline toxicity, and acute fatty liver of pregnancy. Cirrhosis, a diffuse process characterized by fibrosis and a conversion of normal architecture into structurally abnormal nodules, can come about for a variety reasons including alcohol abuse, post necrotic cirrhosis (usually due to chronic active hepatitis), biliary cirrhosis, pigment cirrhosis, cryptogenic cirrhosis, Wilson's disease, and alpha-1-antitrypsin deficiency. Zvegf3 may also be useful for the treatment of hepatic chronic passive congestion (CPC) and central hemorrhagic necrosis (CHN), which are two circulatory changes representing a continuum encountered in right-sided heart failure. Other circulatory disorders that may be treated with zvegf3 include hepatic vein thrombosis, portal vein thrombosis, and cardiac sclerosis. In cases of liver fibrosis it may be beneficial to administer a zvegf3 antagonist to suppress the activation of stellate cells, which have been implicated in the production of extracellular matrix in fibrotic liver (Li and Friedman, *J. Gastroenterol. Hepatol.* 14:618-633, 1999).

Zvegf3 polypeptides can be administered alone or in combination with other vasculogenic or angiogenic agents, including VEGF. For example, basic and acidic FGFs and VEGF have been found to play a role in the development of collateral circulation, and the combined use of zvegf3 with one or more of these factors may be advantageous. VEGF has also been implicated in the survival of transplanted islet cells (Gorden et al. *Transplantation* 63:436-443, 1997; Pepper, *Arteriosclerosis, Throm. and Vascular Biol.* 17:605-619, 1997). Basic FGF has been shown to induce angiogenesis and accelerate healing of ulcers in experimental animals (reviewed by Folkman, *Nature Medicine* 1:27-31, 1995). VEGF has been shown to promote vessel re-endothelialization and to reduce intimal hyperplasia in animal models of restenosis (Asahara et al., *Circulation* 91:2802-2809, 1995; Callow et al., *Growth Factors* 10:223-228, 1994); efficacy of zvegf3 polypeptides can be tested in these and other known models. When using zvegf3 in combination with an additional agent, the two compounds can be administered simultaneously or sequentially as appropriate for the specific condition being treated.

Zvegf3 proteins may be used either alone or in combination with other hematopoietic factors such as IL-3, G-CSF, GM-CSF, or stem cell factor to enhance expansion and mobilization of endothelial precursor stem cells. Cells that can be expanded in this manner include cells isolated from bone marrow or cells isolated from blood. Zvegf3 proteins may also be given directly to an individual to enhance endothelial stem cell production and differentiation within the treated individual. The stem cells, either developed within the patient, or provided back to a patient, may then play a role in modulating areas of ischemia within the body, thereby providing a therapeutic effect. These cells may also be useful in enhancing re-endothelialization of areas devoid of endothelial coverage, such as vascular grafts, vascular stents, and areas where the endothelial coverage has been damaged or removed (e.g., areas of angioplasty). ZvegB proteins may also be used in combination with other growth and differentiation factors such as angiopoietin-1 (Davis et al., *Cell* 87:1161-1169, 1996) to help create and stabilize new vessel formation in areas requiring neovascularization, including areas of ischemia (cardiac or peripheral ischemia), organ transplants, wound healing, and tissue grafting.

Zvegf3 proteins, agonists and antagonists may be used to modulate neurite growth and development and demarcate nervous system structures. As such, Zvegf3 proteins, agonists, or antagonists may useful in the treatment of peripheral neuropathies by increasing spinal cord and sensory neurite outgrowth, and as part of a therapeutic treatment for the regeneration of neurite outgrowths following strokes, brain damage caused by head injuries, and paralysis caused by spinal injuries. Application may also be made in treating neurodegenerative diseases such as multiple sclerosis, Alzheimer's disease and Parkinson's disease. Application may also be made in mediating development and innervation pattern of stomach tissue.

For pharmaceutical use, zvegf3 proteins are formulated for topical or parenteral, particularly intravenous or subcutaneous, delivery according to conventional methods. In general, pharmaceutical formulations will include a zvegf3 polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy, Gennaro*, ed., Mack Publishing Co., Easton, Pa., $19_{th}$ ed., 1995. Zvegf3 will ordinarily be used in a concentration of about 10 to 100 μg/ml of total volume, although concentrations in the range of 1 ng/ml to 1000 μg/ml may be used. For topical application, such as for the promotion of wound healing, the protein will be applied in the range of 0.1-10 μg/$cm^2$ of wound area, with the exact dose determined by the clinician according to accepted standards, taking into account the nature and severity of the condition to be treated, patient traits, etc. Determination of dose is within the level of ordinary skill in the art. The therapeutic formulations will generally be administered over the period required for neovascularization, typically from one to several months and, in treatment of chronic conditions, for a year or more. Dosing is daily or intermittently over the period of treatment. Intravenous administration will be by bolus injection or infusion over a typical period of one to several hours. Sustained release formulations can also be employed. In general, a therapeutically effective amount of zvegf3 is an amount sufficient to produce a clinically significant change in the treated condition, such as a clinically significant reduction in time required by wound closure, a significant reduction in wound area, a significant improvement in vascularization, a significant reduction in morbidity, or a significantly increased histological score.

Proteins of the present invention are useful for modulating the proliferation, differentiation, migration, or metabolism of responsive cell types, which include both primary cells and cultured cell lines. Of particular interest in this regard are liver cells, hematopoietic cells (including stem cells and mature myeloid and lymphoid cells), endothelial cells, neuronal cells, and mesenchymal cells (including fibroblasts and smooth muscle cells). Zvegf3 polypeptides are added to tissue culture media for these cell types at a concentration of about 10 pg/ml to about 1000 ng/ml. Those skilled in the art will recognize that zvegf3 proteins can be advantageously combined with other growth factors in culture media.

Within the laboratory research field, zvegf3 proteins can also be used as molecular weight standards; as reagents in assays for determining circulating levels of the protein, such as in the diagnosis of disorders characterized by over- or under-production of zvegf3 protein; or as standards in the analysis of cell phenotype.

Zvegf3 proteins can also be used to identify inhibitors of their activity. Test compounds are added to the assays disclosed above to identify compounds that inhibit the activity of zvegf3 protein. In addition to those assays disclosed above, samples can be tested for inhibition of zvegf3 activity within a variety of assays designed to measure receptor binding or the stimulation/inhibition of zvegf3-dependent cellular responses. For example, zvegf3-responsive cell lines can be transfected with a reporter gene construct that is responsive to a zvegf3-stimulated cellular pathway. Reporter gene constructs of this type are known in the art, and will generally comprise a zvegf3-activated serum response element (SRE) operably linked to a gene encoding an assayable protein, such as luciferase. Candidate compounds, solutions, mixtures or extracts are tested for the ability to inhibit the activity of zvegf3 on the target cells as evidenced by a decrease in zvegf3 stimulation of reporter gene expression. Assays of this type will detect compounds that directly block zvegf3 binding to cell-surface receptors, as well as compounds that block processes in the cellular pathway subsequent to receptor-ligand binding. In the alternative, compounds or other samples can be tested for direct blocking of zvegf3 binding to receptor using zvegf3 tagged with a detectable label (e.g., $^{125}I$, biotin, horseradish peroxidase, FITC, and the like). Within assays of this type, the ability of a test sample to inhibit the binding of labeled zvegf3 to the receptor is indicative of inhibitory activity, which can be confirmed through secondary assays. Receptors used within binding assays may be cellular receptors or isolated, immobilized receptors.

The activity of zvegf3 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906-1912, 1992; Pitchford et al., *Meth. Enzymol.* 228:84-108, 1997; Arimilli et al., J. *Immunol. Meth.* 212:49-59, 1998; and Van Liefde et al., *Eur. J. Pharmacol.* 346:87-95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zvegf3 proteins, their agonists, and antagonists. The microphysiometer can be used to measure responses of a zvegf3-responsive eukaryotic cell, compared to a control eukaryotic cell that does not respond to zvegf3 polypeptide. Zvegf3-responsive eukaryotic cells comprise cells into which a receptor for zvegf3 has been transfected creating a cell that is responsive to zvegf3, as well as cells naturally responsive to zvegf3 such as cells derived from vascular or neural tissue. Differences, measured by a change, for example, an increase or diminution in extracellular acidification, in the response of cells exposed to zvegf3 polypeptide, relative to a control not exposed to zvegf3, are a direct measurement of zvegf3-modulated cellular responses. Moreover, such zvegf3-modulated responses can be assayed under a variety of stimuli. The present invention thus provides methods of identifying agonists and antagonists of zvegf3 proteins, comprising providing cells responsive to a zvegf3 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change in extracellular acidification rate. Culturing a third portion of the cells in the presence of a zvegf3 protein and the absence of a test compound provides a positive control for the zvegf3-responsive cells and a control to compare the agonist activity of a test compound with that of the zvegf3 polypeptide. Antagonists of zvegf3 can be identified by exposing the cells to zvegf3 protein in the presence and absence of the test compound, whereby a reduction in zvegf3-stimulated activity is indicative of antagonist activity in the test compound.

Zvegf3 proteins can also be used to identify cells, tissues, or cell lines that respond to a zvegf3-stimulated pathway. The microphysiometer, described above, can be used to rapidly identify ligand-responsive cells, such as cells responsive to zvegf3 proteins. Cells are cultured in the presence or absence of zvegf3 polypeptide. Those cells that elicit a measurable change in extracellular acidification in the presence of zvegf3 are responsive to zvegf3. Responsive cells can than be used to identify antagonists and agonists of zvegf3 polypeptide as described above.

Inhibitors of zvegf3 activity (zvegf3 antagonists) include anti-zvegf3 antibodies, soluble zvegf3 receptors (including soluble PDGF alpha receptor; see, e.g., Herren et al., *J. Biol. Chem.* 268:15088-15095, 1993), anti-receptor antibodies, and other peptidic and non-peptidic agents, including ribozymes, small molecule inhibitors, and angiogenically or mitogenically inactive receptor-binding fragments of zvegf3 polypeptides. Such antagonists can be use to block the mitogenic, chemotactic, or angiogenic effects of zvegf3. These antagonists may therefore be useful in reducing the growth of solid tumors by inhibiting neovascularization of the developing tumor, by directly blocking tumor cell growth, or by promoting apoptosis through the inhibition of PDGF alpha receptor-mediated processes. For example, experimental evidence indicates that zvegf3 is produced by glioblastoma cells, suggesting that inhibition of zvegf3 activity may be useful in the treatment of these tumors. Other uses of zvegf3 antagonists include treating diabetic retinopathy, psoriasis, arthritis, and scleroderma; and reducing fibrosis, including scar formation, keloids, liver fibrosis, lung fibrosis (e.g., silicosis, asbestosis), kidney fibrosis (including diabetic nephropathy), and glomerulosclerosis. Inhibitors of zvegf3 may also be useful in the treatment of proliferative vascular disorders wherein zvegf3 activity is pathogenic. Such disorders may include atherosclerosis and intimal hyperplastic restenosis following angioplasty, endarterectomy, vascular grafting, organ transplant, or vascular stent emplacement. These conditions involve complex growth factor-mediated responses wherein certain factors may be beneficial to the clinical outcome and others may be pathogenic.

Inhibitors of zvegf3 may also prove useful in the treatment of ocular neovascularization, including diabetic retinopathy and age-related macular degeneration. Experimental evidence suggests that these conditions result from the expression of angiogenic factors induced by hypoxia in the retina.

Zvegf3 antagonists are also of interest in the treatment of inflammatory disorders, such as rheumatoid arthritis and psoriasis. In rheumatoid arthritis, studies suggest that VEGF plays an important role in the formation of pannus, an extensively vascularized tissue that invades and destroys cartilage. Psoriatic lesions are hypervascular and overexpress the angiogenic polypeptide IL-8.

Zvegf3 antagonists may also prove useful in the treatment of infantile hemangiomas, which exhibit overexpression of VEGF and bFGF during the proliferative phase.

Inhibitors are formulated for pharmaceutical use as generally disclosed above, taking into account the precise chemical and physical nature of the inhibitor and the condition to be treated. The relevant determinations are within the level of ordinary skill in the formulation art. Other angiogenic and vasculogenic factors, including VEGF and bFGF, have been implicated in pathological neovascularization. In such instances it may be advantageous to combine a zvegf3 inhibitor with one or more inhibitors of these other factors.

The polypeptides, nucleic acids, and antibodies of the present invention may be used in diagnosis or treatment of disorders associated with cell loss or abnormal cell proliferation, including cancer, impaired or excessive vasculogenesis or angiogenesis, and diseases of the nervous system. Labeled zvegf3 polypeptides may be used for imaging tumors or other sites of abnormal cell proliferation. In view of the binding of zvegf3 to the PDGF alpha receptor, zvegf3 antagonists may be useful in the treatment of tumors that express this receptor (e.g., glioblastomas, malignant melanomas). Because angiogenesis in adult animals is generally limited to wound healing and the female reproductive cycle, it is a very specific indicator of pathological processes. Angiogenesis is indicative of, for example, developing solid tumors, retinopathies, and arthritis.

Zvegf3 polypeptides and anti-zvegf3 antibodies can be directly or indirectly conjugated to drugs, toxins, radionuclides and the like, and these conjugates used for in vivo diagnostic or therapeutic applications. For instance, polypeptides or antibodies of the present invention may used to identify or treat tissues or organs that express a corresponding anti-complementary molecule (receptor or antigen, respectively, for instance). More specifically, zvegf3 polypeptides or anti-zvegf3 antibodies, or bioactive fragments or portions thereof, can be coupled to detectable or cytotoxic molecules and delivered to a mammal having cells, tissues, or organs that express the anti-complementary molecule. For example, the CUB domain of zvegf3 can be used to target peptidic and non-peptidic moieties to semaphorins as disclosed above.

Suitable detectable molecules can be directly or indirectly attached to the polypeptide or antibody, and include radionuclides, enzymes, substrates, cofactors, inhibitors, fluorescent markers, chemiluminescent markers, magnetic particles, and the like. Suitable cytotoxic molecules can be directly or indirectly attached to the polypeptide or antibody, and include bacterial or plant toxins (for instance, diphtheria toxin, *Pseudomonas* exotoxin, ricin, abrin, saporin, and the like), as well as therapeutic radionuclides, such as iodine-131, rhenium-188 or yttrium-90. These can be either directly attached to the polypeptide or antibody, or indirectly attached according to known methods, such as through a chelating moiety. Polypeptides or antibodies can also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody/fragment-toxin fusion proteins may be used for targeted cell or tissue inhibition or ablation, such as in cancer therapy. Of particular interest in this regard are conjugates of a zvegf3 polypeptide and a cytotoxin, which can be used to target the cytotoxin to a tumor or other tissue that is undergoing undesired cell replication and modification.

In another embodiment, zvegf3-cytokine fusion proteins or antibody/fragment-cytokine fusion proteins may be used for enhancing in vitro cytotoxicity (for instance, that mediated by monoclonal antibodies against tumor targets) and for enhancing in vivo killing of target tissues (for example, blood and bone marrow cancers). See, generally, Homick et al., *Blood* 89:4437-4447, 1997). In general, cytokines are toxic if administered systemically. The described fusion proteins enable targeting of a cytokine to a desired site of action, such as a cell having binding sites for zvegf3, thereby providing an elevated local concentration of cytokine. Suitable cytokines for this purpose include, for example, interleukin-2 and granulocyte-macrophage colony-stimulating factor (GM-CSF). Such fusion proteins may be used to cause cytokine-induced killing of tumors and other tissues exhibiting undesired cell replication.

In yet another embodiment, a zvegf3 polypeptide or anti-zvegf3 antibody can be conjugated with a radionuclide, particularly with a beta-emitting or gamma-emitting radionuclide, and used to reduce restenosis. For instance, iridium-192 impregnated ribbons placed into stented vessels of patients until the required radiation dose was delivered resulted in decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intra-arterially or intraductally, or may be introduced locally at the intended site of action.

Polynucleotides encoding zvegf3 polypeptides are useful within gene therapy applications where it is desired to increase or inhibit zvegf3 activity. For example, Isner et al., *The Lancet* (ibid.) reported that VEGF gene therapy promoted blood vessel growth in an ischemic limb. Additional applications of zvegf3 gene therapy include stimulation of wound healing, repopulation of vascular grafts, stimulation of neurite growth, and inhibition of cancer growth and metastasis.

The present invention also provides polynucleotide reagents for diagnostic use. For example, a zvegf3 gene, a probe comprising zvegf3 DNA or RNA, or a subsequence thereof can be used to determine if the zvegf3 gene is present on chromosome 4 of a human patient or if a mutation has occurred. Detectable chromosomal aberrations at the zvegf3 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; A. J. Marian, *Chest* 108:255-265, 1995).

Radiation hybrid mapping is a somatic cell genetic technique developed for constructing high-resolution, contiguous maps of mammalian chromosomes (Cox et al., *Science* 250: 245-250, 1990). Partial or full knowledge of a gene's sequence allows one to design PCR primers suitable for use with chromosomal radiation hybrid mapping panels. Commercially available radiation hybrid mapping panels that cover the entire human genome, such as the Stanford G3 RH Panel and the GeneBridge 4 RH Panel (Research Genetics, Inc., Huntsville, Ala.), are available. These panels enable rapid, PCR-based chromosomal localizations and ordering of genes, sequence-tagged sites (STSs), and other nonpolymorphic and polymorphic markers within a region of interest. This technique allows one to establish directly proportional physical distances between newly discovered genes of interest and previously mapped markers. The precise knowledge of a gene's position can be useful for a number of purposes, including: 1) determining relationships between short sequences and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The invention is further illustrated by the following non-limiting examples.

EXAMPLES

Example 1

Clones comprising portions of the zvegf3 coding sequence were identified in public and proprietary databases of expressed sequence tags (ESTs). A first clone, corresponding to an EST in a proprietary database, was obtained and sequenced. It contained a 2350-bp insert with an open reading frame of about 800 bp. The 5' end of the ORF was missing. A second clone, corresponding to an EST in a public database, was then sequenced, but it didn't extend the sequence obtained from the first clone. A third clone, from a proprietary database, was then sequenced. This clone contained approximately 156 bp more than the first clone, but was also missing the 5' end.

Northerns were performed using a series of Northern blots (Multiple Tissue Northern Blots, Clontech Laboratories, Inc., Palo Alto, Calif.). An approximately 400-bp DNA probe, based directly on the identified EST, was generated by digestion of a clone corresponding to the first proprietary EST with EcoRI and BglII. The DNA probe was gel-purified using a spin column containing a silica gel membrane (QIAquick™ Gel Extraction Kit; Qiagen, Inc., Valencia, Calif.). The probe was radioactively labeled with $^{32}P$ using a commercially available random-prime labeling kit (Rediprime™ II, Amersham Corp., Arlington Heights, Ill.) according to the manufacturer's specifications. The probe was purified using a push column (NucTrap® column; Stratagene, La Jolla, Calif.; see U.S. Pat. No. 5,336,412). A commercially available hybridization solution (ExpressHyb™ Hybridization Solution; Clontech Laboratories, Inc., Palo Alto, Calif.) was used for prehybridization and as a hybridizing solution for the Northern blots. Hybridization took place overnight at 65° C., and the blots were then washed 4 times in 2×SSC and 0.1% SDS at room temperature, followed by two washes in 0.1×SSC and 0.1% SDS at 50° C. and one wash in 0.1×SSC and 0.1% SDS at 56° C. The Northern blots were then exposed to film overnight at −80° C. and for three days at −80° C. One transcript size was seen in all tissues at approximately 4.0 kb. Signal intensity was highest in thyroid, spinal cord and adrenal gland. Signal intensity was average in heart, kidney, pancreas, prostate, ovary, stomach, and trachea. Signal intensity was weak in all other tissues.

Northern blot analysis was performed using Mouse Multiple Tissue Blots obtained from Clontech Laboratories and Invitrogen (Carlsbad, Calif.). An approximately 400 bp DNA probe, based directly on the identified EST, was generated by digestion of a clone corresponding to the first proprietary EST with EcoRI and BglII. The DNA probe was gel purified using a spin column as disclosed above. The probe was radioactively labeled with $^{32}P$ by random priming as disclosed above. The probe was purified using a NucTrap® push column. Hybridization conditions were as disclosed above. The blots were washed four times in 2×SSC, 0.1% SDS, then twice in 1×SSC at 50° C., then exposed to film overnight at −80° C. and for three days at −80° C. One transcript size of approximately 3.0 kb was seen in 7-day embryo. Three-day exposure showed bands of less intensity in 11-, 15-, and 17-day embryo. The intensity decreased with the age of the embryo. Dot blots showed a spot in 17-day embryo, and with-three day exposure in submaxillary gland. A potential band of approximately 2.0 kb was seen in testis after three days.

Southern blot analysis was performed using a pre-made Southern blot containing EcoRI-digested genomic DNA from nine different eukaryotic species (ZOO-BLOT from Clontech Laboratories). An approximately 400 bp DNA probe, based directly on the first proprietary database EST, was generated by digestion of the corresponding clone with EcoRI and BglII. The DNA probe was gel purified using a spin column. The probe was radioactively labeled with $^{32}P$ by random priming and purified using a push column. Hybridization and wash conditions were as disclosed above for the Mouse Multiple Tissue Blots. The Northern blots were then exposed to film overnight at −80° C. and for three days at −80° C. Strong bands were seen in rabbit, mouse, rat, and monkey.

Example 2

A human salivary gland library was screened for a full-length clone of zvegf3 by PCR. This library was an arrayed library representing $9.6\times10^5$ clones made in the vector pZP5x. The vector pZP5x is the same as vector pZP-9 (deposited with American Type Culture Collection, 10801 University Blvd., Manassas, Va. under Accession Number 98668), but contains a cytomegalovirus promoter instead of a metallothionein promoter between the Asp718 and BamHI sites. The plasmid thus comprises a dihyrofolate reductase gene under control of the SV40 early promoter and SV40 polyadenylation site, and a cloning site to insert the gene of interest under control of the CMV promoter and the human growth hormone (hGH) gene polyadenylation site. The working plate containing 80 pools of 12,000 colonies each was screened by PCR using oligonucleotide primers ZC19,045 (SEQ ID NO:25) and ZC19,047 (SEQ ID NO:26) with an annealing temperature of 60° C. for 35 cycles. There were two strong positives, pools 58 (T-8 F1-F12) and 77 (T-7 H1-H12). The corresponding pools in the transfer plate were then screened by PCR using the same conditions. Two positives were obtained at the transfer level. The positives were T-7 H11 and T-8 F10. 5' RACE reactions were done on the transfer plate pools, and the fragments were sequenced to check zvegf3 sequence and determine if a full-length clone was present. For PCR, oligonucleotide primers ZC12,700 (SEQ ID NO:27) and ZC19,045 (SEQ ID NO:25) were used at an annealing temperature of 61° C. for 5 cycles, then 55° C. for 30 cycles. Sequencing showed that the pool T-7 H11 had a frameshift. Transfer plate 8 pool F10 sequence appeared to be correct, so this pool of DNA was used in filter lifts.

Pool F10 from transfer plate 8 was plated and filter lifted using nylon membranes (Hybond-N™; Amersham Corporation). Approximately 1200 colonies per plate on each of 5 filters were lifted for a total of approximately 6000 colonies. The filters were marked with a hot needle for orientation, then denatured for 6 minutes in 0.5 M NaOH and 1.5 M Tris-HCl, pH 7.2. The filters were then neutralized in 1.5 M NaCl and 0.5 M Tris-HCl, pH 7.2 for 6 minutes. The DNA was affixed to the filters using a UV crosslinker (Stratalinker®, Stratagene, La Jolla, Calif.) at 1200 joules. The filters were prewashed at 65° C. in prewash buffer consisting of 0.25×SSC, 0.25% SDS, and 1 mM EDTA. The solution was changed a total of three times over a 45-minute period to remove cell debris. Filters were prehybridized for approximately 3 hours at 65° C. in 25 ml of ExpressHyb™. The probe was generated using an approximately 400-bp fragment produced by digestion of the first proprietary database clone with EcoRI and BglII and gel-purified using a spin column as disclosed above. The probe was radioactively labeled with $^{32}P$ by random priming as disclosed above and purified using a push column. ExpressHyb™ solution was used for the hybridizing solution for the filters. Hybridization took place overnight at 65° C. Blots were rinsed 2× in 65° C. solution 1 (2×SSC, 0.1% SDS), then washed 4 times in solution 1 at 65° C. The filters were exposed to film overnight at −80° C. There were 14 positives on the filters. 85 clones were picked from the positive areas and screened by PCR using oligonucleotide primers ZC19,045 (SEQ ID NO:25) and ZC19,047 (SEQ ID NO:26) and an annealing temperature of 60° C. Thirteen positives were obtained and streaked out for individual clones. Twenty-four colonies were picked and checked by PCR as previously described. Six positives were obtained, two of which were sequenced. Both sequences were the same and full length. The sequence is shown in SEQ ID NO: 1.

Example 3

The human zvegf3 gene was mapped to chromosome 4 using the commercially available GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (www-genome.wi.mit.edu/cgi-bin/contig/rhmapper.p1) allows mapping relative to the Whitehead Institute/MIT Center for Genome Research's radiation hybrid map of the human genome (the "WICGR" radiation hybrid map), which was constructed with the GeneBridge 4 Radiation Hybrid Panel.

For the mapping of Zvegf3 with the GeneBridge 4 RH Panel, 20 μl reactions were set up in a PCRable 96-well microtiter plate (Stratagene, La Jolla, Calif.) and used in a thermal cycler (RoboCycler® Gradient 96; Stratagene). Each of the 95 PCR reactions contained 2 μl 10×PCR reaction buffer (Clontech Laboratories, Inc., Palo Alto, Calif.), 1.6 μl dNTPs mix (2.5 mM each, PERKIN-ELMER, Foster City, Calif.), 1 μl sense primer ZC 20,368 (SEQ ID NO:28), 1 μl antisense primer ZC 20,369 (SEQ ID NO:29), 2 μl of a density increasing agent and tracking dye (RediLoad, Research Genetics, Inc., Huntsville, Ala.), 0.4 μl of a commercially available DNA polymerase/antibody mix (50× Advantage™ KlenTaq Polymerase Mix, obtained from Clontech Laboratories, Inc.), 25 ng of DNA from an individual hybrid clone or control, and x μl $ddH_2O$ for a total volume of 20 μl. The reaction mixtures were overlaid with an equal amount of mineral oil and sealed. The PCR cycler conditions were as follows: an initial 4-minute denaturation at 94° C.; 35 cycles of 45 seconds denaturation at 94° C., 45 seconds annealing at 56° C., and 75 seconds extension at 72° C.; followed by a final extension of 7 minutes at 72° C. The reaction products were separated by electrophoresis on a 2% agarose gel (Life Technologies, Gaithersburg, Md.).

The results showed that zvegf3 maps 3.56 cR_3000 from the framework marker CHLC.GATA72A08 on the chromosome 4 WICGR radiation hybrid map. Proximal and distal framework markers were CHLC.GATA72A08 and WI-3936, respectively. The use of surrounding markers positions the zvegf3 gene in the 4q28.3 region on the integrated LDB chromosome 4 map (The Genetic Location Database, University of Southhampton, WWW server: cedar.genetics.soton.ac.uk/public_html/).

Using substantially the same methods, the mouse zvegf3 gene was mapped to chromosome 3, linked to the framework marker D3Mit212 located at 39.7 cM. This region is syntenic with the human zvegf3 locus.

Example 4

A PCR panel was screened for mouse zvegf3 DNA. The panel contained 8 cDNA samples from brain, bone marrow, 15-day embryo, testis, salivary gland, placenta, 15-day embryo (Clontech Laboratories), and 17-day embryo (Clontech Laboratories) libraries.

PCR mixtures contained oligonucleotide primers zc21,222 (SEQ ID NO:38) and zc21,224 (SEQ ID NO:39). The reaction was run at an annealing temperature of 66° C. with an extension time of 2 minutes for a total of 35 cycles using Ex Taq™ DNA polymerase (PanVera, Madison, Wis.) plus antibody. DNA samples found to be positive for zvegf3 by PCR and confirmed by sequencing included mouse 15-day embryo library total pool cDNA, mouse 15-day embryo (Clontech Laboratories) and 17-day embryo (both obtained from Clontech Laboratories), mouse salivary gland library total pool cDNA, and mouse testis library total pool cDNA. Fragments of about 600 bp from each of the mouse 15-day embryo library total pool cDNA, mouse 15-day embryo mcDNA, and mouse 17-day embryo mcDNA PCR products were sequenced. Sequence from the mouse 17-day embryo mcDNA and mouse 15-day embryo library total pool cDNA products confirmed the fragments to be mouse zvegf3 DNA.

The mouse 15-day embryo library was screened for full-length zvegf3 DNA. This library was an arrayed library representing $9.6\times10^5$ clones in the pCMV.SPORT 2 vector (Life Technologies, Gaithersburg, Md.). The working plate, containing 80 pools of 12,000 colonies each, was screened by PCR using oligonucleotide primers zc2,223 (SEQ ID NO:40) and zc2,224 (SEQ ID NO:39) with an annealing temperature of 66° C. for 35 cycles. Eighteen positives were obtained. Fragments from four pools (A2, A10, B2, and C4)were sequenced; all were confirmed to encode zvegf3. Additional rounds of screening using the same reaction conditions and pools from the working and source plates identified one positive pool (5D).

Positive colonies were screened by hybridization. Pool 5D from original source plate #5 was plated at about 250 colonies per plate and transferred to nylon membranes (Hybond-N™; Amersham Corporation, Arlington Heights, Ill.). Five filters were lifted for a total of ~1250 colonies. The filters were marked with a hot needle for orientation, then denatured for 6 minutes in 0.5 M NaOH and 1.5 M Tris-HCl, pH 7.2. The filters were then neutralized in 1.5 M NaCl and 0.5 M Tris-HCl, pH 7.2 for 6 minutes. The DNA was fixed to the filters using a a UV crosslinker (Stratalinker®, Stratagene, La Jolla, Calif.) at 1200 joules. A probe was generated by PCR using oligonucleotide primers zc21,223 (SEQ ID NO:40) and zc21,224 (SEQ ID NO:39), and a mouse 15-day embryo template at an annealing temperature of 66° C. for 35 cycles. The PCR fragment was gel purified using a spin column containing a silica gel membrane (QIAquick™ Gel Extraction Kit; Qiagen, Inc., Valencia, Calif.). The DNA was radioactively labeled with $^{32}P$ using a commercially available kit (Rediprime™ II random-prime labeling system; Amersham Corp., Arlington Heights, Ill.) according to the manufacturer's specifications. The probe was purified using a commercially available push column (NucTrap® column; Stratagene, La Jolla, Calif.; see U.S. Pat. No. 5,336,412). The filters were prewashed at 65° C. in prewash buffer consisting of 0.25× SSC, 0.25% SDS and 1 mM EDTA. The solution was changed a total of three times over a 45-minute period to remove cell debris. Filters were prehybridized overnight at 65° C. in 25 ml of a hybridization solution (ExpressHyb™ Hybridization Solution; Clontech Laboratories, Inc., Palo Alto, Calif.), then hybridized overnight at 65° C. in the same solution. Filters were rinsed twice at 65° C. in pre-wash buffer (0.25×SSC, 0.25% SDS, and 1 mM EDTA), then washed twice in pre-wash buffer at 65° C. Filters were exposed to film for 2 days at −80° C. There were 10 positives on the filters. 3 clones were picked from the positive areas, streaked out, and 15 individual colonies from these three positives were screened by PCR using primers zc21,223 (SEQ ID NO:40) and zc21,334 (SEQ ID NO:41) at an annealing temp of 66° C. Two positives were recovered and sequenced. Both sequences were found to be the same and encoded full-length mouse zvegf3 (SEQ ID NO:42).

The amino acid sequence is highly conserved between mouse and human zvegf3s, with an overall amino acid sequence identity of 87%. The secretory peptide, CUB domain, inter-domain, and growth factor domain have 82%, 92%, 79% and 94% amino acid identity, respectively.

Example 5

Northern blotting was performed using Mouse Multiple Tissue Blots from Origene, Rockville, Md. and Clontech, Palo Alto, Calif. An approximately 800-bp DNA probe was generated by PCR using primer zc21,223 (SEQ ID NO:40) for the 5' end and primer zc21,224 (SEQ ID NO:39) for the 3' end. The reaction was run for 35 cycles at an annealing temperature of 66° C. using Ex Taq™ DNA polymerase (PanVera). The reaction product was gel purified using a spin column containing a silica gel membrane and labeled with $^{32}P$ using a commercially available labeling kit (Multiprime™ DNA labeling system, Amersham Corp.) according to the manufacturer's specifications. The labeled probe was purified using a push column. A commercially available hybridization solution (ExpressHyb™ Hybridization Solution; Clontech Laboratories, Inc.) was used for prehybridization and as a hybridizing solution for the Northern blots. Hybridization took place overnight at 65° C., then the blots were washed 4 times in 2×SCC and 0.05% SDS at room temperature, followed by two washes in 0.1×SSC and 0.1% SDS at 50° C. The blots were then exposed to film two days and overnight at −80° C. Multiple transcript sizes were observed. Transcripts of 3.5 and 4.0 kb were seen in 7, 11, 15 and 17-day embryo, with the strongest at 7 days and tapering off at 17 days. A ~3.0 kb transcript was seen in kidney, liver, brain, and possibly testis. A ~1.0 kb transcript was seen in testis, muscle, and spleen. Dot blots corresponded to the northern blots.

Example 6

To make transgenic animals expressing zvegf3 genes requires adult, fertile males (studs) (B6C3fl, 2-8 months of age (Taconic Farms, Germantown, N.Y.)), vasectomized males (duds) (B6D2fl, 2-8 months, (Taconic Farms)), prepubescent fertile females (donors) (B6C3fl, 4-5 weeks (Taconic Farms)) and adult fertile females (recipients) (B6D2fl, 2-4 months, (Taconic Farms)).

The donors are acclimated for 1 week, then injected with approximately 8 IU/mouse of Pregnant Mare's Serum gonadotrophin (Sigma, St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope (Leica MZ12 Stereo Microscope, Leica, Wetzlar, Germany). The oviducts are collected and eggs are released into urinanalysis slides containing hyaluronidase (Sigma Chemical Co.). Eggs are washed once in hyaluronidase, and twice in Whitten's W640 medium (Table 7; all reagents available from Sigma Chemical Co.) that has been incubated with 5% $CO_2$, 5% $O_2$, and 90% $N_2$ at 37° C. The eggs are stored in a 37° C/5% $CO_2$ incubator until microinjection.

TABLE 7

| | mgs/200 ml | mgs/500 ml |
|---|---|---|
| NaCl | 1280 | 3200 |
| KCl | 72 | 180 |
| $KH_2PO_4$ | 32 | 80 |
| $MgSO_4.7H_2O$ | 60 | 150 |
| Glucose | 200 | 500 |
| $Ca^{2+}$ Lactate | 106 | 265 |
| Benzylpenicillin | 15 | 37.5 |
| Streptomycin $SO_4$ | 10 | 25 |
| $NaHCO_3$ | 380 | 950 |
| Na Pyruvate | 5 | 12.5 |
| $H_20$ | 200 ml | 500 ml |
| 500 mM EDTA | 100 μl | 250 μl |
| 5% Phenol Red | 200 μl | 500 μl |
| BSA | 600 | 1500 |

Figure 2:
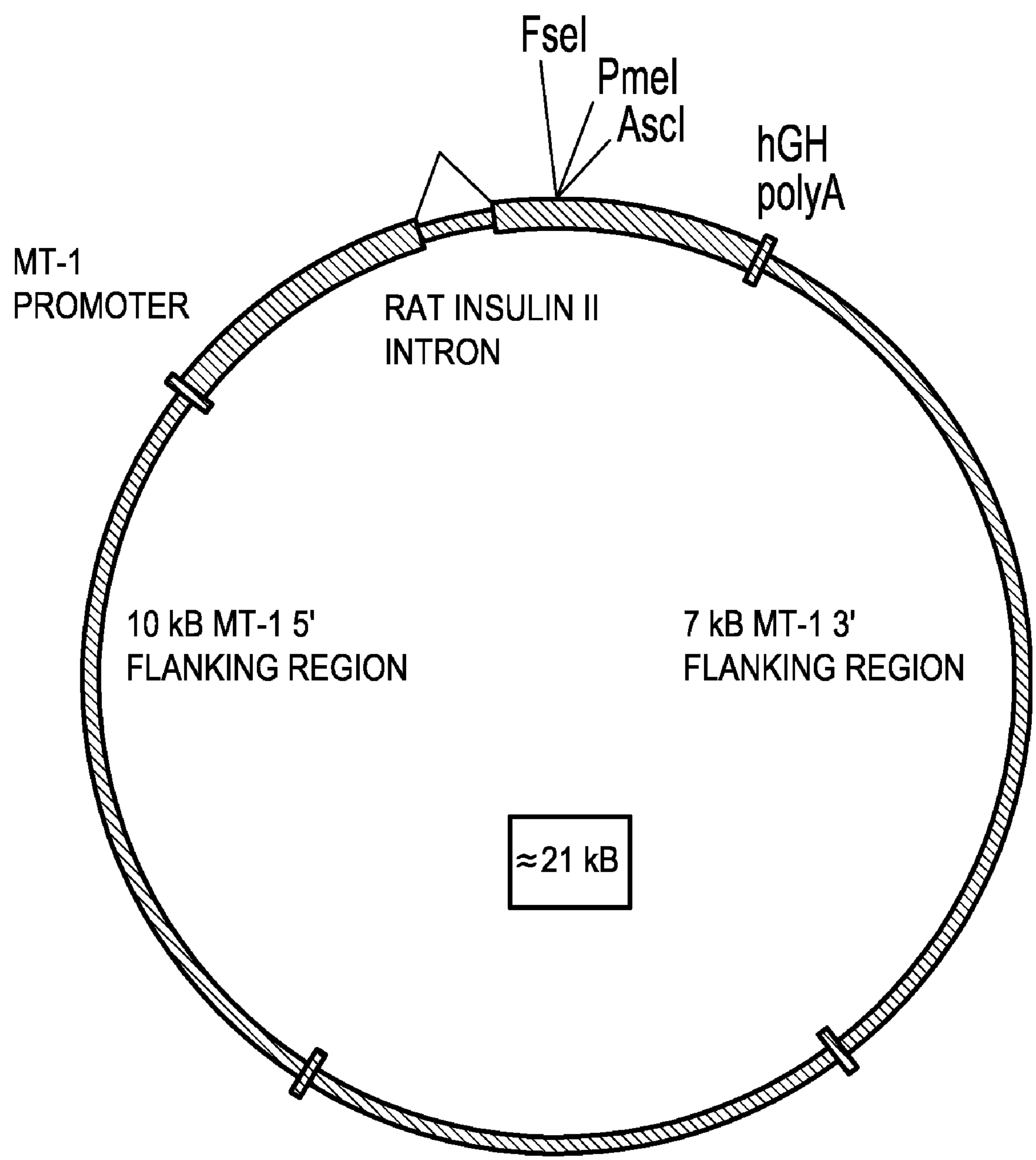
FIG. 2 is an illustration of the vector pHB12-8 for use in expressing cDNAs in transgenic animals.

Zvegf3 cDNA is inserted into the expression vector pHB12-8 (see FIG. 2). Vector pHB12-8 was derived from p2999B4 (Palmiter et al., *Mol. Cell Biol.* 13:5266-5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-1 5' flanking sequence and 7 kb of MT-1 3' flanking sequence. The cDNA is inserted between the insulin II and hGH sequences.

10-20 micrograms of plasmid DNA is linearized, gel-purified, and resuspended in 10 mM Tris pH 7.4, 0.25 mM EDTA pH 8.0, at a final concentration of 5-10 nanograms per microliter for microinjection.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary) and injected into individual eggs. Each egg is penetrated with the injection needle into one or both of the haploid pronuclei.

Picoliters of DNA are injected into the pronuclei, and the injection needle is withdrawn without coming into contact with the nucleoli. The procedure is repeated until all the eggs are injected. Successfully microinjected eggs are transferred into an organ tissue-culture dish with pregassed W640 medium for storage overnight in a 37° C./5% $CO_2$ incubator.

The following day, 2-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy 2-cell embryos from the previous day's injection are transferred into the recipient. The swollen ampulla is located and holding the oviduct between the ampulla and the bursa, and a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs are allowed to slide in. The peritoneal wall is closed with one suture, and the skin is closed with a wound clip. The mice recuperate on a 37° C. slide warmer for a minimum of 4 hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using a commercially available kit (DNeasy™ 96 Tissue Kit; Qiagen, Valencia, Calif.) following the manufacturer's instructions. Genomic DNA is analyzed by PCR using primers designed to the human growth hormone (hGH) 3' UTR portion of the transgenic vector. The use of a region unique to the human sequence (identified from an alignment of the human and mouse growth hormone 3' UTR DNA sequences) ensures that the PCR reaction does not amplify the mouse sequence. Primers zc17,251 (SEQ ID NO:30) and zc17,252 (SEQ ID NO:31) amplify a 368-base-pair fragment of hGH. In addition, primers zc17,156 (SEQ ID NO:32) and zc17,157 (SEQ ID NO:33), which hybridize to vector sequences and amplify the cDNA insert, may be used along with the hGH primers. In these experiments, DNA from animals positive for the transgene will generate two bands, a 368-base-pair band corresponding to the hGH 3' UTR fragment and a band of variable size corresponding to the cDNA insert.

Once animals are confirmed to be transgenic (TG), they are back-crossed into an inbred strain by placing a TG female with a wild-type male, or a TG male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the xiphoid process. Using sterile technique, a small 1.5-2 cm incision is made below the sternum, and the left lateral lobe of the liver is exteriorized. Using 4-0 silk, a tie is made around the lower lobe securing it outside the body cavity. An atraumatic clamp is used to hold the tie while a second loop of absorbable Dexon (American Cyanamid, Wayne, N.J.) is placed proximal to the first tie. A distal cut is made from the Dexon tie, and approximately 100 mg of the excised liver tissue is placed in a sterile petri dish. The excised liver section is transferred to a 14-ml polypropylene round bottom tube, snap frozen in liquid nitrogen, and stored on dry ice. The surgical site is closed with suture and wound clips, and the animal's cage is placed on a 37° C. heating pad for 24 hours post-operatively. The animal is checked daily post-operatively, and the wound clips are removed 7-10 days after surgery.

Analysis of the mRNA expression level of each transgene is done using an RNA solution hybridization assay or real-time PCR on an ABI Prism 7700 (PE Applied Biosystems, Inc., Foster City, Calif.) following the manufacturer's instructions.

An adenovirus vector was prepared using a liver-specific albumin gene enhancer and basal promoter (designated "AEO promoter"). The albumin promoter construct (designated pAEO) was constructed by inserting a 2.2 kb Not1/EcoRV fragment from pALBdelta2L (Pinkert et al., *Genes Dev.* 1:268-276, 1987) and an 850 bp NruI/Not1 DNA segment comprising the rat insulin II intron, an FseI/PmeI/AscI polylinker, and the human growth hormone poly A sequence into a commercially available phagemid vector (pBluescript® KS(+); Stratagene, La Jolla, Calif.). For microinjection, the plasmid is digested with Not to liberate the expression cassette.

An additional adenovirus vector was constructed using an epithelial cell-specific keratin gene (K14) promoter (Vassar et al., *Proc. Natl. Acad. Sci. USA* 86:1563-1567, 1989). The 1038-bp open reading frame encoding full-length human zvegf3 was amplified by PCR so as to introduce an optimized initiation codon and flanking 5' PmeI and 3' AscI sites using the primers ZC20,180 (SEQ ID NO:34) and ZC20,181 (SEQ ID NO:35). The resulting PmeI/AscI fragment was subcloned into the polylinker of pKFO114, a basal keratinocyte-restricted transgenic vector comprising the human keratin 14 (K14) promoter (an approximately 2.3 Kb fragment amplified from human genomic DNA [obtained from Clontech Laboratories, Inc.] based on the sequence of Staggers et al., "Sequence of the promoter for the epidermal keratin gene, K14", GenBank accession #U11076, 1994), followed by a heterologous intron (a 294-bp BstXI/PstI fragment from pIRES1hyg (Clontech Laboratories, Inc.; see, Huang and Gorman, *Nucleic Acids Res.* 18:937-947, 1990), a PmeI/AscI polylinker, and the human growth hormone gene polyadenylation signal (a 627 bp SmaI/EcoRI fragment; see, Seeburg, *DNA* 1:239-249, 1982). The transgene insert was separated from the plasmid backbone by NotI digestion and agarose gel purification, and fertilized ova from matings of B6C3F1Tac mice or inbred FVB/NTac mice were microinjected and implanted into pseudopregnant females essentially as described by Malik et al., *Molec. Cell. Biol.* 15:2349-2358, 1995. Transgenic founders were identified by PCR on genomic tail DNA using primers specific for the human growth hormone poly A signal (ZC17,252, SEQ ID NO:31; and ZC17,251, SEQ ID NO:30) to amplify a 368-bp diagnostic product. Transgenic lines were initiated by breeding founders with C57BL/6Tac or FVB/NTac mice.

Transgenic mice were generated essentially as disclosed above using MT-1, K14, and AEO promoters. Four MT-1/zvegf3 transgenic mice were generated. In one animal (female) approximately 800 molecules zvegf3 mRNA/cell were produced in the liver after zinc induction. This animal had enlargement of the liver and spleen. Also observed were proliferation of hepatic sinusoidal cells and extra-medullary hematopoiesis. One K14/zvegf3 transgenic mouse (female) showed a low level of expression with low body weight, low hematocrit, and low platelet count. One AEO/zvegf3 transgenic mouse (male) with a low level of expression exhibited liver sinusoidal cell proliferation.

Example 7

An expression plasmid containing all or part of a polynucleotide encoding zvegf3 is constructed via homologous recombination. A fragment of zvegf3 cDNA is isolated by PCR using the polynucleotide sequence of SEQ ID NO: 1 with flanking regions at the 5' and 3' ends corresponding to the vector sequences flanking the zvegf3 insertion point. The primers for PCR each include from 5' to 3' end: 40 bp of flanking sequence from the vector and 17 bp corresponding to the amino and carboxyl termini from the open reading frame of zvegf3.

Ten µl of the 100 µl PCR reaction is run on a 0.8% low-melting-temperature agarose (SeaPlaque GTG®; FMC Bio-Products, Rockland, Me.) gel with 1×TBE buffer for analysis. The remaining 90 µl of PCR reaction is precipitated with the addition of 5 µl 1 M NaCl and 250 µl of absolute ethanol. The plasmid pZMP6, which has been cut with SmaI, is used for recombination with the PCR fragment. Plasmid pZMP6 was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. pZMP6 is a mammalian expression vector containing an expression cassette having the cytomegalovirus immediate early promoter, multiple restriction sites for insertion of coding sequences, a stop codon, and a human growth hormone terminator. The plasmid also contains an *E. coli* origin of replication; a mammalian selectable marker expression unit comprising an SV40 promoter, enhancer and origin of replication, a DHFR gene, and the SV40 terminator; as well as the URA3 and CEN-ARS sequences required for selection and replication in *S. cerevisiae.*

One hundred microliters of competent yeast (*S. cerevisiae*) cells are independently combined with 10 µl of the various DNA mixtures from above and transferred to a 0.2-cm electroporation cuvette. The yeast/DNA mixtures are electropulsed using power supply settings of 0.75 kV (5 kV/cm), ∝ ohms, 25 µF. To each cuvette is added 600 µl of 1.2 M sorbitol, and the yeast is plated in two 300-µl aliquots onto two URA-D plates and incubated at 30° C. After about 48 hours, the $Ura^+$ yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid-washed glass beads and 200 µl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 µl ethanol (EtOH), followed by centrifugation for 10 minutes at 4° C. The DNA pellet is resuspended in 10 µl $H_2O$.

Transformation of electrocompetent *E. coli* host cells (Electromax DH10B™ cells; obtained from Life Technologies, Inc., Gaithersburg, Md.) is done with 0.5-2 ml yeast DNA prep and 40 ul of cells. The cells are electropulsed at 1.7 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is plated in 250-µl aliquots on four LB AMP plates (LB broth (Lennox), 1.8% Bacto™ Agar (Difco), 100 mg/L Ampicillin).

Figure 3:
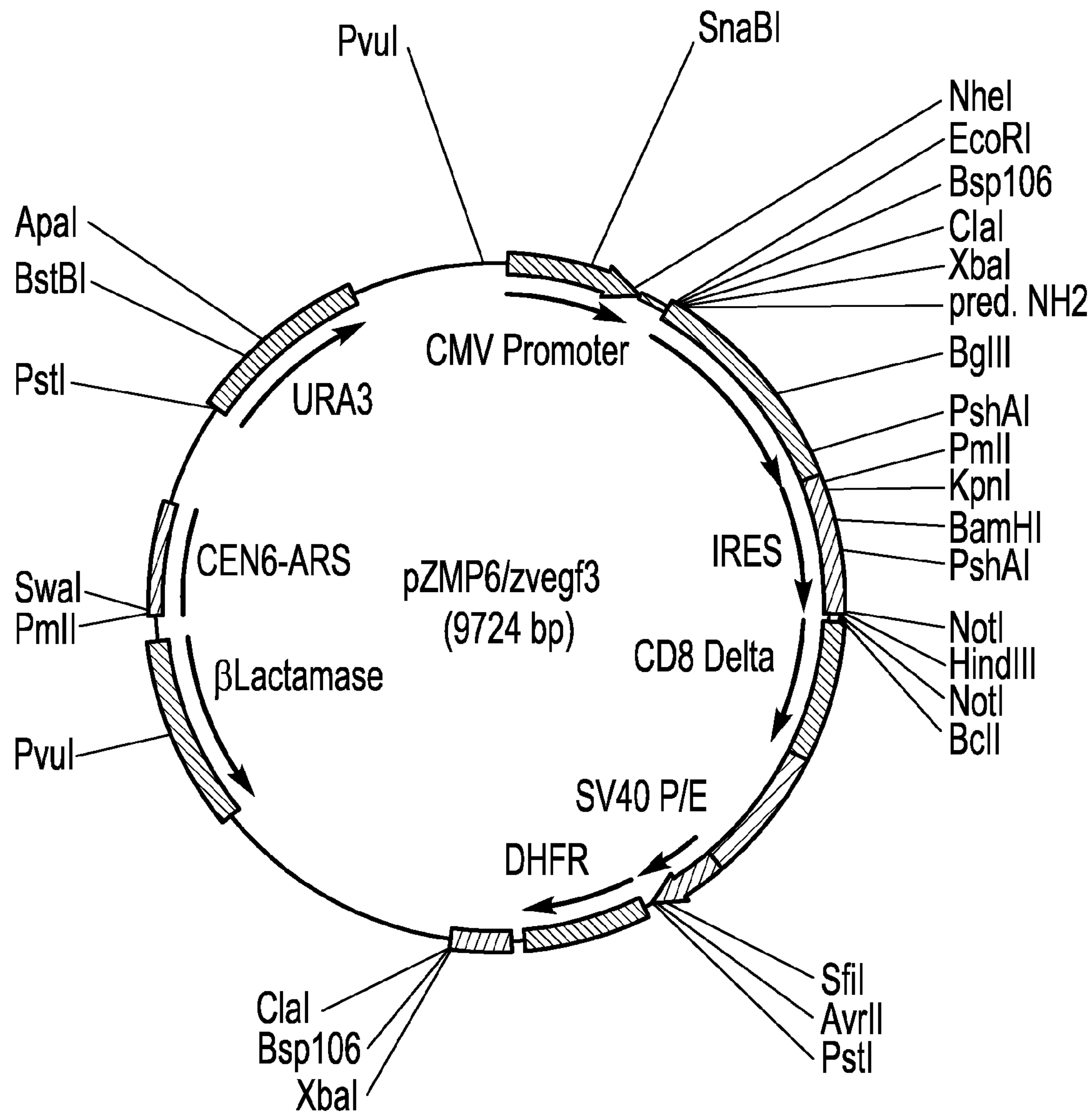
FIG. 3 is an illustration of the vector pZMP6/zvegf3.

Individual clones harboring the correct expression construct for zvegf3 are identified by restriction digest to verify the presence of the zvegf3 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated pZMP6/zvegf3 (FIG. 3).

Example 8

CHO DG44 cells (Chasin et al., *Som. Cell. Molec. Genet.* 12:555-666, 1986) are plated in 10-cm tissue culture dishes and allowed to grow to approximately 50% to 70% confluency overnight at 37° C., 5% $CO_2$, in Ham's F12/FBS media (Ham's F12 medium, Life Technologies), 5% fetal bovine serum (Hyclone, Logan, Utah.), 1% L-glutamine (JRH Biosciences, Lenexa, Kans.), 1% sodium pyruvate (Life Technologies). The cells are then transfected with the plasmid pZMP6/zvegf3 by liposome-mediated transfection using a 3:1 (w/w) liposome formulation of the polycationic lipid 2,3-dioleyloxy-N-[2(sperminecarboxamido)ethyl]-N,N-dimethyl-1-propaniminium-trifluoroacetate and the neutral lipid dioleoyl phosphatidylethanolamine in membrane-filetered water (Lipofectamine™ Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). Plasmid pZMP6/Zvegf3 is diluted into 15-ml tubes to a total final volume of 640 µl with SF media. 35 µl of Lipofectamine™ is mixed with 605 µl of SF medium. The Lipofectamine™ mixture is added to the DNA mixture and allowed to incubate approximately 30 minutes at room temperature. Five ml of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 1% PSN media is added to each plate. The plates are incubated at 37° C. overnight, and the DNA:Lipofectamine™ mixture is replaced with fresh 5% FBS/Ham's media the next day. On day 3 post-transfection, the cells are split into T-175 flasks in growth medium. On day 7 postransfection, the cells are stained with FITC-anti-CD8 monoclonal antibody (Pharmingen, San Diego, Calif.) followed by anti-FITC-conjugated magnetic beads (Miltenyi Biotec). The CD8-positive cells are separated using commercially available columns (mini-MACS columns; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 µl per well as necessary during this process. When a large percentage of the colonies in the plate are near confluency, 100 µl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5mM β-mercaptoethanol, at 65° C., 10 minutes, then in 2.5% non-fat dry milk Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the antibody-HRP conjugate in 2.5% non-fat dry milk Western A buffer for 1 hour at room temperature on a rotating shaker. The filter is then washed three times at room temperature in PBS plus 0.01% Tween 20, 15 minutes per wash. The filter is developed with chemiluminescence reagents (ECL™ direct labelling kit; Amersham Corp., Arlington Heights, Ill.) according to the manufacturer's directions and exposed to film (Hyperfilm ECL, Amersham) for approximately 5 minutes. Positive clones are trypsinized from the 96-well dish and transferred to 6-well dishes in selection medium for scaleup and analysis by Western blot.

Example 9

Full-length zvegf3 protein was produced in BHK cells transfected with pZMP6/zvegf3 (Example 7). BHK 570 cells (ATCC CRL-10314) were plated in 10-cm tissue culture dishes and allowed to grow to approximately 50 to 70% confluence overnight at 37° C., 5% $CO_2$, in DMEM/FBS media (DMEM, Gibco/BRL High Glucose; Life Technologies), 5% fetal bovine serum (Hyclone, Logan, Utah.), 1 mM L-glutamine (JRH Biosciences, Lenexa, Kans.), 1 mM sodium pyruvate (Life Technologies). The cells were then transfected with pZMP6/zvegf3 by liposome-mediated transfection (using (Lipofectamine™; Life Technologies), in serum free (SF) media (DMEM supplemented with 10 mg/ml transferrin, 5 mg/ml insulin, 2 mg/ml fetuin, 1% L-glutamine and 1% sodium pyruvate). The plasmid was diluted into 15-ml tubes to a total final volume of 640 μl with SF media. 35 μl of the lipid mixture was mixed with 605 μl of SF medium, and the mixture was allowed to incubate approximately 30 minutes at room temperature. Five milliliters of SF media was added to the DNA:lipid mixture. The cells were rinsed once with 5 ml of SF media, aspirated, and the DNA:lipid mixture was added. The cells were incubated at 37° C. for five hours, then 6.4 ml of DMEM/10% FBS, 1% PSN media was added to each plate. The plates were incubated at 37° C. overnight, and the DNA:lipid mixture was replaced with fresh 5% FBS/DMEM media the next day. On day 5 post-transfection, the cells were split into T-162 flasks in selection medium (DMEM+5% FBS, 1% L-Gln, 1% NaPyr, 1 μM methotrexate). Approximately 10 days post-transfection, two 150-mm culture dishes of methotrexate-resistant colonies from each transfection were trypsinized, and the cells are pooled and plated into a T-162 flask and transferred to large-scale culture.

Example 10

Figure 4:
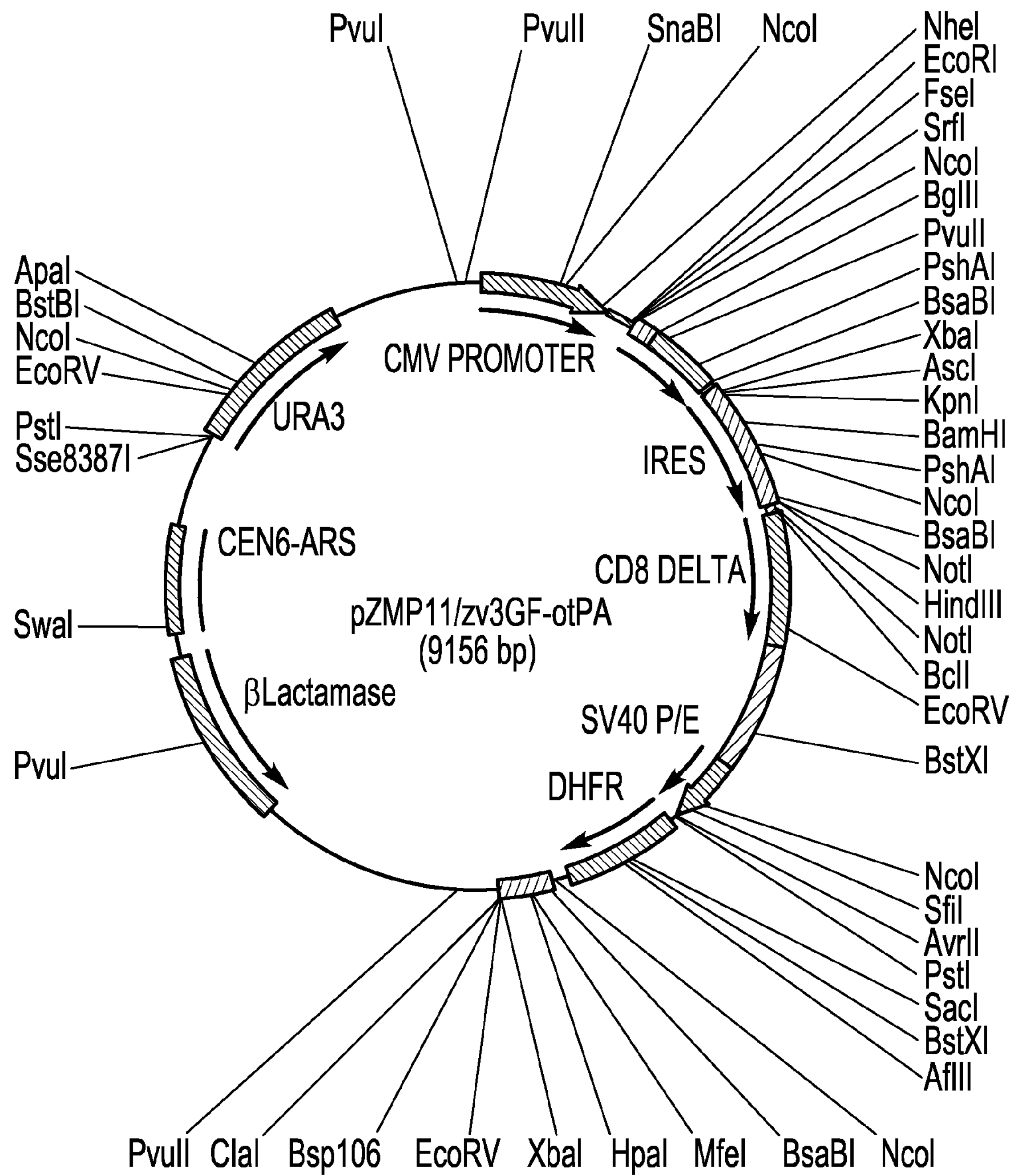
FIG. 4 is an illustration of the vector pZMP11/zv3GF-otPA.

A mammalian cell expression vector for the growth factor domain of zvegf3 was constructed essentially as disclosed in Example 7. The coding sequence for the growth factor domain (residues 235-345 of SEQ ID NO:2), joined to a sequence encoding an optimized t-PA secretory signal sequence (U.S. Pat. No. 5,641,655) was joined to the linearized pZMP11 vector downstream of the CMV promoter. The plasmid pZMP11 is a mammalian expression vector containing an expression cassette having the CMV immediate early promoter, a consensus intron from the variable region of mouse immunoglobulin heavy chain locus, Kozak sequences, multiple restriction sites for insertion of coding sequences, a stop codon, and a human growth hormone terminator. The plasmid also contains an IRES element from poliovirus, the extracellular domain of CD8 truncated at the C-terminal end of the transmembrane domain, an *E. coli* origin of replication, a mammalian selectable marker expression unit having an SV40 promoter, enhancer and origin of replication, a DHFR gene, the SV40 terminator, and the URA3 and CEN-ARS sequences required for selection and replication in *S. cerevisiae*. The resulting vector, designated pZMP11/zv3GF-otPA, is shown in FIG. 4.

BHK 570 cells were transfected with pZMP11/zv3GF-otPA and cultured essentially as disclosed in Example 9.

Example 11

For construction of adenovirus vectors, the protein coding region of human zvegf3 was amplified by PCR using primers that added PmeI and AscI restriction sties at the 5' and 3' termini respectively. PCR primers ZC20,180 (SEQ ID NO:34) and ZC20,181 (SEQ ID NO:35) were used with a full-length zvegf3 cDNA template in a PCR reaction as follows: one cycle at 95° C. for 5 minutes; followed by 15 cycles at 95° C. for 1 min., 61° C. for 1 min., and 72° C. for 1.5 min.; followed by 72° C. for 7 min.; followed by a 4° C. soak. The PCR reaction product was loaded onto a 1.2% low-melting -temperature agarose gel in TAE buffer (0.04 M Tris-acetate, 0.001 M EDTA). The zvegf3 PCR product was excised from the gel and purified using a commercially available kit comprising a silica gel mambrane spin column (QIAquick™ PCR Purification Kit and gel cleanup kit; Qiagen, Inc.) as per kit instructions. The PCR product was then digested with PmeI and AscI, phenol/chloroform extracted, EtOH precipitated, and rehydrated in 20 ml TE (Tris/EDTA pH 8). The 1038 bp zvegf3 fragment was then ligated into the PmeI-AscI sites of the transgenic vector pTG12-8 (also known as pHB12-8; see Example 6) and transformed into *E. coli* DH10B™ competent cells by electroporation. Clones containing zvegf3 were identified by plasmid DNA miniprep followed by digestion with PmeI and AscI. A positive clone was sequenced to insure that there were no deletions or other anomalies in the construct. The sequence of zvegf3 cDNA was confirmed.

DNA was prepared using a commercially available kit (Maxi Kit, Qiagen, Inc.), and the 1038b p zvegf3 cDNA was released from the pTG12-8 vector using PmeI and AscI enzymes. The cDNA was isolated on a 1% low melting temperature agarose gel and was excised from the gel. The gel slice was melted at 70° C., and the DNA was extracted twice with an equal volume of Tris-buffered phenol and precipitated with EtOH. The DNA was resuspended in 10 μl $H_2O$.

The zvegf3 cDNA was cloned into the EcoRV-AscI sites of a modified pAdTrack-CMV (He, T-C. et al., *Proc. Natl. Acad. Sci. USA* 95:2509-2514, 1998). This construct contains the green fluorescent protein (GFP) marker gene. The CMV promoter driving GFP expression was replaced with the SV40 promoter, and the SV40 polyadenylation signal was replaced with the human growth hormone polyadenylation signal. In addition, the native polylinker was replaced with FseI, EcoRV, and AscI sites. This modified form of pAdTrack-CMV was named pZyTrack. Ligation was performed using a commercially available DNA ligation and screening kit (Fast-Link™ kit; Epicentre Technologies, Madison, Wis.). Clones containing zvegf3 were identified by digestion of mini prep DNA with FseI and AscI. In order to linearize the plasmid, approximately 5 μg of the resulting pZyTrack zvegf3 plasmid was digested with PmeI. Approximately 1 μg of the linearized plasmid was cotransformed with 200 ng of supercoiled pAdEasy (He et al., ibid.) into *E. coli* BJ5183 cells (He et al., ibid.). The co-transformation was done using a Bio-Rad Gene Pulser at 2.5 kV, 200 ohms and 25 μFa. The entire co-transformation mixture was plated on 4 LB plates containing 25 μg/ml kanamycin. The smallest colonies were picked and expanded in LB/kanamycin, and recombinant adenovirus DNA was identified by standard DNA miniprep procedures. Digestion of the recombinant adenovirus DNA with FseI and AscI confirmed the presence of the zvegf3 insert. The recombinant adenovirus miniprep DNA was transformed into *E. coli* DH10B™ competent cells, and DNA was prepared using a Maxi Kit (Qiagen, Inc.) aaccording to kit instructions.

Approximately 5 μg of recombinant adenoviral DNA was digested with PacI enzyme (New England Biolabs) for 3 hours at 37° C. in a reaction volume of 100 μl containing 20-30U of PacI. The digested DNA was extracted twice with an equal volume of phenol/chloroform and precipitated with ethanol. The DNA pellet was resuspended in 10 μl distilled water. A T25 flask of QBI-293A cells (Quantum Biotechnologies, Inc. Montreal, Qc. Canada), inoculated the day before and grown to 60-70% confluence, were transfected with the Pacd digested DNA. The PacI-digested DNA was diluted up to a total volume of 50 μl with sterile HBS (150 mM NaCl, 20 mM HEPES). In a separate tube, 20 μl of 1 mg/ml N-[1-(2,3-Dioleoyloxy)propyl]-N,N,N-trimethyl-ammonium salts (DOTAP) (Boehringer Mannheim, Indianapolis, Ind.) was diluted to a total volume of 100 μl with HBS. The DNA was added to the DOTAP, mixed gently by pipeting up and down, and left at room temperature for 15 minutes. The media was removed from the 293A cells and washed with 5 ml serum-free minimum essential medium (MEM) alpha containing lmM sodium pyruvate, 0.1 mM MEM non-essential amino acids, and 25 mM HEPES buffer (reagents obtained from Life Technologies, Gaithersburg, Md.). 5 ml of serum-free MEM was added to the 293A cells and held at 37° C. The DNA/lipid mixture was added drop-wise to the T25 flask of 293A cells, mixed gently, and incubated at 37° C. for 4 hours. After 4 h the media containing the DNA/lipid mixture was aspirated off and replaced with 5 ml complete MEM containing 5% fetal bovine serum. The transfected cells were monitored for GFP expression and formation of foci (viral plaques).

Seven days after transfection of 293A cells with the recombinant adenoviral DNA, the cells expressed the GFP protein and started to form foci (viral "plaques"). The crude viral lysate was collected using a cell scraper to collect all of the 293A cells. The lysate was transferred to a 50-ml conical tube. To release most of the virus particles from the cells, three freeze/thaw cycles were done in a dry ice/ethanol bath and a 37° waterbath.

The crude lysate was amplified (Primary (1°) amplification) to obtain a working "stock" of zvegf3 rAdV lysate. Ten 10-cm plates of nearly confluent (80-90%) 293A cells were set up 20 hours previously, 200 μl of crude rAdV lysate added to each 10-cm plate and monitored for 48 to 72 hours looking for CPE under the white light microscope and expression of GFP under the fluorescent microscope. When all of the 293A cells showed CPE (Cytopathic Effect) this 1° stock lysate was collected and freeze/thaw cycles performed as described under Crude rAdV Lysate.

Secondary (2°) amplification of zvegf3 rAdV was obtained as follows: Twenty 15-cm tissue culture dishes of 293A cells were prepared so that the cells were 80-90% confluent. All but 20 ml of 5% MEM media was removed, and each dish was inoculated with 300-500 μl of the 1° amplified rAdv lysate. After 48 hours the 293A cells were lysed from virus production, the lysate was collected into 250-ml polypropylene centrifuge bottles, and the rAdV was purified.

NP-40 detergent was added to a final concentration of 0.5% to the bottles of crude lysate in order to lyse all cells. Bottles were placed on a rotating platform for 10 minutes agitating as fast as possible without the bottles falling over. The debris was pelleted by centrifugation at 20,000×G for 15 minutes. The supernatant was transferred to 250-ml polycarbonate centrifuge bottles, and 0.5 volume of 20% PEG8000/2.5 M NaCl solution was added. The bottles were shaken overnight on ice. The bottles were centrifuged at 20,000×G for 15 minutes and, the supernatant was discarded into a bleach solution. Using a sterile cell scraper, the white, virus/PEG precipitate from 2 bottles was resuspended in 2.5 ml PBS. The resulting virus solution was placed in 2-ml microcentrifuge tubes and centrifuged at 14,000×G in the microcentrifuge for 10 minutes to remove any additional cell debris. The supernatant from the 2-ml microcentrifuge tubes was transferred into a 15-ml polypropylene snapcap tube and adjusted to a density of 1.34 g/ml with CsCl. The volume of the virus solution was estimated, and 0.55 g/ml of CsCl was added. The CsCl was dissolved, and 1 ml of this solution weighed 1.34 g. The solution was transferred to 3.2-ml, polycarbonate, thick-walled centrifuge tubes and spun at 348,000×G for 3-4 hours at 25° C. The virus formed a white band. Using wide-bore pipette tips, the virus band was collected.

The virus from the gradient had a large amount of CsCl which had to be removed before it was used on cells. Commercially available ion-exchange columns (PD-10 columns prepacked with Sephadex® G-25M; Pharmacia Biotech, Piscataway, N.J.) were used to desalt the virus preparation. The column was equilibrated with 20 ml of PBS. The virus was loaded and allowed to run into the column. 5 ml of PBS was added to the column, and fractions of 8-10 drops were collected. The optical densities of 1:50 dilutions of each fraction were determined at 260 nm on a spectrophotometer. A clear absorbance peak was present between fractions 7-12. These fractions were pooled, and the optical density (OD) of a 1:25 dilution was determined. OD was converted to virus concentration using the formula: (OD at 260 nm)(25)($1.1=10^{12}$)=virions/ml. The OD of a 1:25 dilution of the zvegf3 rAdV was 0.145, giving a virus concentration of $4\times10^{12}$ virions/ml.

To store the virus, glycerol was added to the purified virus to a final concentration of 15%, mixed gently but effectively, and stored in aliquots at −80° C.

A protocol developed by Quantum Biotechnologies, Inc. (Montreal, Canada) was followed to measure recombinant virus infectivity. Briefly, two 96-well tissue culture plates were seeded with $1\times10^4$ 293A cells per well in MEM containing 2% fetal bovine serum for each recombinant virus to be assayed. After 24 hours 10-fold dilutions of each virus from $1\times10^{-2}$ to $1\times10^{-14}$ were made in MEM containing 2% fetal bovine serum. 100 μl of each dilution was placed in each of 20 wells. After 5 days at 37° C., wells were read either positive or negative for Cytopathic Effect (CPE) and a value for "Plaque Forming Units/ml" (PFU) was calculated.

$TCID_{50}$ formulation used was as per Quantum Biotechnologies, Inc., above. The titer (T) was determined from a plate where virus was diluted from $10^{-2}$ to $10^{-14}$, and read 5 days after the infection. At each dilution a ratio ® of positive wells for CPE per the total number of wells was determined.

To calculate titer of the undiluted virus sample: the factor, "F"=1+d(S-0.5); where "S" is the sum of the ratios ®; and "d" is Log10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T).

The zvegf3 adenovirus had a titer of $1.8=10^{10}$ pfu/ml.

Example 12

Treatment of mice with zvegf3-adenovirus led to changes in liver and spleen. The livers were pale and very enlarged, with enlarged vessels at the tips of the lobes. The livers also showed sinusoidal cell proliferation. Changes were also seen in hepatocytes (hypertrophy, degeneration, and necrosis) and were most likely non-specific effects of adenovirus infection. Splenic change consisted of increased extramedulary hematopoiesis, which was correlated with enlarged splenic size.

Example 13

Data from adenovirus-treated and transgenic mice were consistent with increased hematopoiesis and/or angiogenesis in the test animals. A study was therefore undertaken to test whether adenovirally delivered zvegf3 stimulated cells in the hematopoietic or lymphoid compartments to proliferate, as determined by examination of peripheral blood, histological examination, and incorporation of bromodeoxy uridine (BrdU) into tissues.

Mice (male, C57B1, 7 weeks old) were divided into three groups. On day 0, parental or zvegf3 adenovirus was administered to the first (n=11) and second (n=12) groups, respectively, via the tail vein, with each mouse receiving a dose of ~$1\times10^{11}$ particles in ~0.1 ml volume. The third group (n=8) received no treatment. Each mouse was given two intraperitoneal doses of 3 mg of freshly made BrdU solution at approximately 24 and 12 hours prior to sacrifice. On days 2, 4, 6, 8, and 10, two mice from each treatment group and one or two untreated mice were sacrificed, and tissues and blood were harvested. Samples were analyzed for complete blood count (CBC) and serum chemistry, and slides were prepared for manual differential blood and marrow progenitor cell analysis. One femur, lung, heart, thymus, liver, kidney, spleen, pancreas, duodenum, and mesenteric lymph nodes were submitted for standard histology and assessment of BrdU incorporation. The lining of the duodenum served as the control tissue for BrdU incorporation.

In addition, two mice that received approximately half the dose of zvegf3 adenovirus particles and one mouse that received the full dose of parental adenovirus were sacrificed and analyzed as described above on day 16.

A piece of liver from each mouse was saved for mRNA assay of adenovirus protein to examine the time course of expression of the adenovirus preparations.

Beginning on day 6, most of the animals treated with either adenovirus had visibly enlarged livers and spleens compared to the untreated mice. The livers of the zvegf3 adenovirus-treated mice tended to look more pale than animals treated with the parental virus. Proliferation of sinusoidal cells was observed in liver. Visual inspection suggested that these cells were stellate cells and/or fibroblasts. Spleen color was the same in both groups. Most of the animals that received the zvegf3 adenovirus had paler femur shafts, with the marrow lighter in color.

Peripheral blood CBCs showed a possible difference in platelet counts, but not in RBC or WBC counts between zvegf3 and parental virus-treated animals. In comparison to the untreated and partental virus-treated groups, the zvegf3 group had lower platelet counts on days 2, 4, 6, and 8, but not on day 10. The mean platelet volume (average size of individual platelets) in the zvegf3 group also tended to be greater, consistent with a relative increase in the larger, immature platelet population.

BrdU labeling showed increased cell proliferation in kidney, mainly in the medulla and to a lesser extent in the cortex. Proliferating cells appeared to be interstitial cells, which may have included fibroblasts and/or mesangial cells.

Example 14

Zvegf3 was assayed in an aortic ring outgrowth assay (Nicosia and Ottinetti, *Laboratory Investigation* 63(1):115, 1990; Villaschi and Nicosia, *Am. J. Pathology* 143(1):181-190, 1993). Thoracic aortas were isolated from 1-2 month old SD male rats and transferred to petri dishes containing HANK's buffered salt solution. The aortas were flushed with additional HANK's buffered salt solution to remove blood, and adventitial tissue surrounding the aorta was carefully removed. Cleaned aortas were transferred to petri dishes containing EBM basal media, serum free (Clonetics, San Diego, Calif.). Aortic rings were obtained by slicing approximately 1-mm sections using a scalpel blade. The ends of the aortas used to hold the aorta in place were not used. The rings were rinsed in fresh EBM basal media and placed individually in a wells of a 24-well plate coated with Matrigel (Becton Dickinson, Bedford, Mass.). The rings were overlayed with an additional 50 µl Matrigel and placed at 37° C. for 30 minutes to allow the matrix to gel. Test samples were diluted in EBM basal serum-free media supplemented with 100 units/ml penicillin, 100 µg/ml streptomycin and HEPES buffer and added at 1 ml/well. Background control was EBM basal serum-free media alone. Basic FGF (R&D Systems, Minneapolis, Minn.) at 20 ng/ml was used as a positive control. Zvegf33 pZyTrack andenovirus (Example 11) was added to wells, assuming a cell count of 500,000 cells and a multiplicity of infection of 5000 particles/cell. A null ZyTrack adenovirus (zPar) was used as a control. Samples were added in a minimum of quadruplets. Rings were incubated for 5-7 days at 37° C. and analyzed for growth. Aortic outgrowth was scored by multiple, blinded observers using 0 as no growth and 4 as maximum growth. Zvegf3 adenovirus produced a significant increase in outgrowth as compared to controls, and was comparable to other potent growth factors (e.g., bFGF).

In additional experiments, purified zvegf3 growth factor domain also caused a signicant increase in outgrowth at concentrations down to approximately 50 ng/ml.

Zvegf3-responsive cells were stained for alpha smooth muscle actin (characteristic of SMCs), von Willebrand factor (characteristic of endothelial cells), type I collagen (characteristic of fibroblasts), and vimentin (stains all three cell types). The observed staining patterns indicated that the cells were fibroblasts and smooth muscle cells, with the possible inclusion of pericytes.

Example 15

Thirty mice (male, c57BL6) were each injected subcutaneously with $2.5\times10^5$ Lewis lung carcinoma cells (obtained from American Type Culture Collection, Mannassas, Va.). Three days after implantation of cells, the mice were split into three groups of ten and were injected with either saline, zvegf3 adenovirus ($1\times10^{11}$ particles), or control adenovirus ($1\times10^{11}$ particles). Growth of tumors was monitored by dimensional measurement on day 14 and by gross tumor weight at the time of sacrifice (day 21). Lungs, liver and tumor were examined by histological methods. Tumor size was significantly lower in the zvegf3-treated group compared to the control adenovirus group ($p<0.007$), but not significantly different from the saline-treated group ($p=0.6$). The incidence of metastasis was low and did not differ among the groups.

Example 16

Myeloproliferative activity of zvegf3 is tested in a mouse model of myelosuppression. On day 0, mice (male C57B1) in the myelosuppressed groups are administered 450cGy of radiation and 1.2 mg of Carboplatin. A second set of mice remain untreated. Between days 0 and 7, purified zvegf3, thrombopoietin, or vehicle control are administered subcutaneously. On days −7, 6, 10, 15, and 20 the mice are bled under anasthetic by retro-orbital puncture. Blood samples are analyzed for CBCs, and slides are made for manual differential and immature cell analysis.

When recovery of blood cell lineages is observed, the animals are sacrificed. Bone marrow is harvested for microscopic analysis and bone marrow progenitor assays. Spleen and liver are harvested for histological examination to determine extramedullary hematopoiesis. Lung, thymus, heart, testis, and kidney are analyzed for histology.

Example 17

Polyclonal anti-peptide antibodies were prepared by immunizing two female New Zealand white rabbits with the peptides huzvegf3-1 (residues 80-104 of SEQ ID NO:2), huzvegf3-2 (residues 299-314 of SEQ ID NO:2), huzvegf3-3 (residues 299-326 of SEQ ID NO:2 with an N -terminal cys residue), or huzvegf3-4 (residues 195-225 of SEQ ID NO:2 with a C-terminal cys residue). The peptides were synthesized using an Applied Biosystems Model 431A peptide synthesizer (Applied Biosystems, Inc., Foster City, Calif.) according to the manufacturer's instructions. The peptides huzvegf3-1, huzvegf3-3, and huzvegf3-4 were then conjugated to the carrier protein maleimide-activated keyhole limpet hemocyanin (KLH) through cysteine residues (Pierce Chemical Co., Rockford, Ill.). The peptide huzvefg3-2 was conjugated to the carrier protein KLH using gluteraldehyde. The rabbits were each given an initial intraperitoneal (IP) injection of 200 μg of conjugated peptide in Complete Freund's Adjuvant (Pierce Chemical Co.) followed by booster IP injections of 100 μg conjugated peptide in Incomplete Freund's Adjuvant every three weeks. Seven to ten days after the administration of the third booster injection, the animals were bled and the serum was collected. The rabbits were then boosted and bled every three weeks.

The huzvegf3 peptide-specific antibodies were affinity purified from the rabbit serum using an CNBr-Sepharose® 4B peptide column (Pharmacia Biotech) that was prepared using 10 mg of the respective peptides per gram CNBr-Sepharose®, followed by dialysis in PBS overnight. Peptide specific-huzvegf3 antibodies were characterized by an ELISA titer check using 1 μg/ml of the appropriate peptide as an antibody target. The huzvegf3-1 peptide-specific antibodies have a lower limit of detection (LLD) of 500 μg/ml by ELISA on its appropriate antibody target and recognize full-length recombinant protein (MBP-fusion; see Example 28) by ELISA. The huzvegf3-2 peptide-specific antibodies had an LLD of 1 ng/ml by ELISA. The huzvegf3-3 peptide-specific antibodies had an LLD of 50 pg/ml by ELISA and recognized recombinant protein by Western Blot analysis. The huzvegf3-4 peptide-specific antibodies had an LLD of 50 pg/ml by ELISA and recognized recombinant protein by Western Blot analysis.

Example 18

Recombinant zvegf3 was analyzed by Western blotting using antibodies to the huzvegf3-1 and huzvegf3-3 peptides. Protein was produced in BHK cells as disclosed above, and in 293 and MVEC (microvascular endothelial) cells transfected with adenovirus vectors according to conventional methods. Samples were electrophoresed and transferred to nitrocellulose (0.2 μm; Bio-Rad Laboratories, Hercules, Calif.) at room temperature using a Hoeffer Scientific Instruments (San Francisco, Calif.) model TE22 blotter with stirring according to directions provided in the instrument manual. The transfer was run at 500 mA for one hour or 50 mA for 12 hours in a buffer containing 25 mM Tris base, 200 mM glycine, and 20% methanol. The filters were then blocked with 10% non-fat dry milk in buffer A (50 mM Tris (pH 7.4), 5 mM EDTA (pH 8.0), 0.05% Igepal CA-630, 150 mM NaCl, 0.25% gelatin) for 10 minutes at room temperature. The nitrocellulose was quickly rinsed, then primary antibody was added in buffer A containing 2.5% non-fat dry milk. The blots were incubated for 1 hour at room temperature or overnight at 4° C. with gentle shaking or rocking. Following the incubation, blots were washed three times for 10 minutes each in buffer A. Secondary antibody (goat anti-rabbit IgG conjugated to horseradish peroxidase; obtained from Rockland Inc., Gilbertsville, Pa.) diluted 1:4000 in buffer A containing 2.5% non-fat dry milk was added, and the blots were incubated for one hour at room temperature with gentle shaking or rocking. The blots were then washed three times, 10 minutes each, in buffer A, then quickly rinsed in $H_2O$. The blots were developed using commercially available chemiluminescent substrate reagents (SuperSignal® ULTRA reagents 1 and 2 mixed 1:1; reagents obtained from Pierce Chemical Co.), and exposed to film (Hyperfilm ECL™; Amersham Pharmacia Biotech, Piscataway, N.J.) for times ranging from 1 second to 5 minutes or as necessary.

Using the 3-1 antibody, full-length zvegf3 produced in BHK cells showed two bands ($M_r$≈46 kDa and 30 kDa) under reducing conditions. The larger band was consistent with the size of the full-length zvegf3 monomer, and the smaller band with the CUB domain+interdomain region. Under non-reducing conditions, there was a major band at $M_r$≈78 kDa, which appeared to be the dimerized, full-length molecule. Two smaller, minor bands were also observed. Similar results were obtained with the 3-3 antibody, but under reducing conditions the smaller band ran at $M_r$≈22 kDa. Sequence analysis of the smaller band showed it to be the isolated growth factor domain.

The recombinant growth factor domain (produced in BHK cells), analyzed using the 3-3 antibody, ran as a broad band of $M_r$≈18 kDa under reducing conditions. Under non-reducing conditions, the protein ran as two bands of $M_r$≈16 and 28 kDa, indicating the presence of both dimeric and monomeric forms of the growth factor domain.

Zvegf3 protein produced in 293 cells grown in serum-free media showed sizes consistent with the predicted full-length protein. Under reducing conditions, the protein ran at $M_r$≈47 kDa, and under non-reducing conditions at $M_r$≈78 kDa when blots were probed with either antibody 3-1 or 3-3. Addition of serum to the media resulted in cleavage of the protein, as seen in the BHK-produced material.

MVEC cells grown in the presence of 1% serum produced zvegf3 protein that ran at $M_r$≈23 kDa under reducing conditions, and $M_r$≈28 kDa under non-reducing conditions using the 3-3 antibody. These results indicate cleavage of the protein, with the antibody recognizing the monomeric and dimeric forms of the growth factor domain. When the MVEC cells were adapted to serum-free media, full-length protein was observed.

Example 19

Recombinant zvegf3 growth factor domain was produced in BHK 570 cells grown in cell factories. Three 15-liter cultures were harvested, and the media were sterile filtered using a 0.2 μfilter. Expression levels were estimated by western blot analysis of media samples concentrated to 20× vs. 5K cut-off and serially diluted by two-fold to 1.25×. Signal intensity was compared to a signal on the same blot from an MBP-zvegf3 fusion protein standard (see Example 28) for which the protein concentration had been determined by amino acid analysis. Expression levels were consistently between 0.25 and 0.35 mg/L of media.

Protein was purified from conditioned media by a combination of cation exchange chromatography and hydrophobic interaction chromatography. Culture medium was diluted with 0.1 M acetic acid, pH 3.0, containing 0.3 M NaCl at a ratio of 60%:40%, (medium:acetic acid) to deliver a process stream at 14 mS conductivity and pH 4.0. This stream was delivered to a strong cation exchange resin (Poros® HS; PerSeptive Biosystems, Framingham, Mass.) with a bed volume of 50 ml in a 2-cm diameter column at a flow rate of 20 ml/minute. A 50-ml bed was sufficient to process 45 L of media and capture all of the target protein. Bound protein was eluted, following column washing for 10 column volumes in 10 mM acetic acid with 0.15 M NaCl at pH=4.0, by forming a linear gradient to 2M NaCl in 10 mM acetic acid, pH 4.0. Ten-ml fractions were captured into tubes containing 2 ml 2.0 M Tris, pH 8.0 to neutralize the acidity. Samples from the cation exchange column were analyzed by SDS PAGE with silver staining and western blotting for the presense of zvegf3. The vegf3 growth domain eluted at 0.2-0.5 M NaCl. Protein-containing fractions were pooled. A 25-ml bed of chromatography medium (Toso Haas Ether chromatography medium) in a 2 cm diameter column was equilibrated in 1.8 M $(NH_4)_2S0_4$ in 25 mM Na phosphate buffer at pH 7.4.

The pooled protein from the cation exchange step was adjusted to 1.8 M $(NH_4)_2SO_4$ in 25 mM Na phosphate, pH 7.0. This stream was flowed over the column at 10 ml/minute. Once the loading was completed the column was washed for 10 column volumes with the equilibration buffer prior to eluting with a 10 column volume gradient formed between the equilibration buffer and 40 mM boric acid at pH 8.8. The zvegf3 growth factor domain protein eluted fairly early in the gradient between 1.5 and 1.0 M $(NH_4)_2S0_4$. At this point the protein was 40-60% pure with a major contaminent being insulin-like growth factor binding protein 4 (IGFBP4).

Protein from the HIC (Ether) chromatography step was applied to a C4 reverse-phase HPLC column. The zvegf3 growth factor domain protein eluted at 36% acetonitrile. This material still contained approximately 20% (mole/mole) IGFB4.

Example 20

Recombinant zvegf3 growth factor domain is purified from cell-conditioned media by a combination of cation exchange chromatography, hydrophobic interaction chromatography, and nickel affinity chromatography. Protein is captured on a strong cation exchange medium and eluted essentially as disclosed in Example 19. The eluted protein is fuirther purified by hydrophobic interaction chromatography on an ether resin (Poros® ET; PerSeptive Biosystems). The partially purified zvegf3 protein is then bound to a nickel chelate resin at pH 7.0-8.0 in 25 mM Na phosphate buffer containing 0.25 M NaCl. The bound protein is eluted with a descending pH gradient down to pH 5.0 or an imidazole gradient. The eluate from the nickel column is adjusted to 1 M $(NH_4)_2SO_4$, 20 mM MES (morphilino ethanesulfonic acid) at pH 6.0 and passed through a phenyl ether hydrophobic interaction chromatography column (Poros® PE, PerSeptive Biosystems) that has been equilibrated in 1 M $(NH_4)_2SO_4$, 20 mM MES, pH 6.0. IGFBP4 and minor contaminants are retained on the column. The pass-through fraction, which contains highly purified zvegf3, is collected. The collected protein is desalted according to conventional methods (e.g., dialysis, ion-exchange chromatography).

Example 21

Recombinant zvegf3 was analyzed for mitogenic activity on human aortic smooth muscle cells (HAoSMC; Clonetics Corp., Walkersville, Md.) and human umbilical vein endothelial cells (HUVEC; Clonetics Corp.). HAoSMC and HUVEC were plated at a density of 5,000 cells/well in 96-well culture plates and grown for approximately 24 hours in DMEM containing 10% fetal calf serum at 37° C. Cells were quiesced by incubating them for 24 hours in serum-free DMEM/Ham's F-12 medium containing insulin (5 μg/ml), transferrin (20 μg/ml), and selenium (16 pg/ml) (ITS). At the time of the assay, the medium was removed, and test samples were added to the wells in triplicate. Test samples consisted of either conditioned media (CM) from adenovirally-infected HaCaT human keratinocyte cells (Boukamp et al., *J. Cell. Biol.* 106:761-771, 1988) expressing full-length zvegf3, purified growth factor domain expressed in BHK cells, or control media from cells infected with parental adenovirus (Zpar). The CM was concentrated 10-fold using a 15 ml centrifugal filter device with a 10K membrane filter (Ultrafree®; Millipore Corp., Bedford, Mass.), then diluted back to 3× with ITS medium and added to the cells. The control CM was generated from HaCaT cells infected with a parental green fluorescent protein-expressing adenovirus and treated identically to the zvegf3 CM. Purified protein in a buffer containing 0.1% BSA was serially diluted into ITS medium at concentrations of 1 μg/ml to 1 ng/ml and added to the test plate. A control buffer of 0.1% BSA was diluted identically to the highest concentration of zvegf3 protein and added to the plate. For measurement of [$^3$H]thymidine incorporation, 20 μl of a 50 μCi/ml stock in DMEM was added directly to the cells, for a final activity of 1 μCi/well. After another 24 hour incubation, mitogenic activity was assessed by measuring the uptake of [$^3$H]thymidine. Media were removed and cells were incubated with 0.1 ml of trypsin until cells detached. Cells were harvested onto 96-well filter plates using a sample harvester (FilterMate™ harvester; Packard Instrument Co., Meriden, Conn.). The plates were then dried at 65° C. for 15 minutes, sealed after adding 40 μl/well scintillation cocktail (Microscint®; Packard Instrument Co.) and counted on a microplate scintillation counter (Topcount®; Packard Instrument Co.).

Results presented in Table 8 demonstrate that zvegf3 CM had approximately 1.5-fold higher mitogenic activity on HAoSM cells over control CM, and purified protein caused a maximal 1.8-fold increase in [$^3$H]thymidine incorporation over the buffer control.

TABLE 8

| Sample | CPM Incorporated | |
|---|---|---|
| | Mean | St. dev. |
| zvegf3 (3x CM) | 81089 | 8866 |
| Zpar (3x CM) | 58760 | 2558 |
| zvegf3 GF domain, 1 μg/ml | 63884 | 3281 |
| zvegf3 GF domain, 500 ng/ml | 57484 | 9744 |
| zvegf3 GF domain, 100 ng/ml | 70844 | 10844 |
| zvegf3 GF domain, 50 ng/ml | 61164 | 2813 |
| zvegf3 GF domain, 10 ng/ml | 60676 | 1514 |
| zvegf3 GF domain, 5 ng/ml | 60197 | 2481 |
| zvegf3 GF domain, 1 ng/ml | 49205 | 5208 |

TABLE 8-continued

| Sample | CPM Incorporated Mean | St. dev. |
|---|---|---|
| Buffer control | 39645 | 9793 |
| PDGF 10 ng/ml (maximal response) | 50634 | 4238 |
| Media alone (basal response) | 24220 | 2463 |

Results presented in Table 9 demonstrate that zvegf3 CM had no mitogenic activity on HUVEC compared to the control CM, and purified protein caused a maximal 1.3-fold increase in [$^3$H]thymidine incorporation over the buffer control.

TABLE 9

| Sample | CPM Incorporated Mean | St. dev. |
|---|---|---|
| zvegf3 (3x CM) | 62723 | 10716 |
| Zpar (3x CM) | 61378 | 1553 |
| zvegf3 VEGF domain, 1 μg/ml | 44901 | 6592 |
| zvegf3 VEGF domain, 500 ng/ml | 41921 | 5330 |
| zvegf3 VEGF domain, 100 ng/ml | 35613 | 5187 |
| zvegf3 VEGF domain, 50 ng/ml | 31107 | 525 |
| zvegf3 VEGF domain, 10 ng/ml | 28505 | 2950 |
| zvegf3 VEGF domain, 5 ng/ml | 29290 | 988 |
| zvegf3 VEGF domain, 1 ng/ml | 28586 | 2718 |
| Buffer control | 33461 | 404 |
| VEGF 50 ng/ml (maximal response) | 53225 | 5229 |
| Media alone (basal response) | 22264 | 2814 |

Example 22

Recombinant zvegf3 protein was assayed for stimulation of intracellular calcium release as an indicator of receptor binding and activation. Cells were cultured in chambered borosilicate coverglass slides. On the day of assay, cells were incubated for 30 minutes at room temperature in KRW buffer (KrebsRingerWollheim; 140 mM NaCl, 3.6 mM KCl, 0.5 mM $NaH_2PO_4$, 0.5 mM $MgSO_4$ 2 mM $NaHCO_3$, 3 mM glucose, 1.5 mM $CaCl_2$, 10 mM HEPES pH 7.4) containing 2 μM fura-2 AM (obtained from Molecular Probes Inc., Eugene, Oreg.), washed twice with KRW buffer, and allowed to sit at room temperature for at least 15 minutes before addition of growth factor or cell-conditioned culture medium (CM) to be tested. Changes in cytosolic calcium were measured by fluorescence ratio imaging (excitation at 340 nm divided by excitation at 380 nm). Digital imaging was carried out using an inverted fluorescent microscope (Nikon TE300) equipped with an oil objective (Nikon 40× Plan Fluor). Images were acquired using a Princeton CCD digital camera and analyzed with Universal Imaging Metafluor software. Data are presented in Table 10.

TABLE 10

| Cell Line | Zvegf3 CM | Control CM | VEGF | PDGF BB |
|---|---|---|---|---|
| aortic ring cells | + | − | − | + |
| pericytes | + | − | − | + |
| aortic smooth muscle cells | + | − | − | + |
| aortic adventitial fibroblasts | + | − | − | + |

Example 23

Northern blot analysis was performed using total RNA from the human neuronal and glial cell lines A172 (glioblastoma), NTera 2 (teratocarcinoma neuronal precursor; obtained from Strategene Cloning Systems, La Jolla, Calif.), U-87 MG (glioblastoma/astrocytoma), U-118 MG (glioblastoma), U138 MG (glioblastoma), U373 MG (glioblastoma). Except as noted, cell lines were obtained from American Type Culture Collection, Manassas, Va. Blots were prepared using 10 μg of RNA per lane. An approximately 400 bp DNA probe was generated by digestion of human zvegf3 cDNA with EcoRI and BglII. The DNA probe was gel electrophoresis followed by extraction using a spin column containing a silica gel membrane (QIAquick™ Gel Extraction Kit; Qiagen, Inc., Valencia, Calif.). The probe was radioactively labeled with $^{32}$P using a commercially available kit (Rediprime™ II random-prime labeling system; Amersham Corp., Arlington Heights, Ill.) according to the manufacturer's specifications. The probe was purified using a push column. Hybridization took place overnight at 65° C. in a commercially available solution (ExpressHyb™ Hybridization Solution; Clontech Laboratories, Inc.).

The blots were then washed 4× in 2×SCC and 0.05% SDS at room temperature, followed by two washes in 0.1×SSC and 0.1% SDS at 50° C. One transcript size was detected at approximately 4 kb in A172, U-87 MG, U-118 MG, U138 MG, and U373 MG samples. Signal intensity was highest for U373 MG, U-118 MG, and U-87 MG.

Example 24

10 μg of recombinant zvegf3 growth factor domain protein was combined with 438 μl PBS containing 1 mCi Na-$^{125}$I (Amersham Corp.). One derivatized, nonporous polystyrene bead (IODO-Beads®; Pierce Chemical Co., Rockford, Ill.) was added, and the reaction mixture was incubated one minute on ice. The iodinated protein was separated from unicorporated $^{125}$I by gel filtration, elution buffer PBS, 0.25% gelatin. The active fraction contained 4.9 μg/mL $^{125}$I-zvegf3 with a specific activity of $4.3\times10^4$ cpm/ng.

The following cell lines were plated into the wells of a 24-well tissue culture dish and cultured in growth medium for three days:

1. Rat aortic ring pool (ARC)
2. Rat aortic ring clone 14B (ARC#14B)
3. Human umbilical vien endothelial cells, passage 5 (HUVEC)
4. Human aortic adventicial fibroblasts, passage 4 (AOAF)
5. Human aortic smooth muscle cells, passage 9 (AOSMC)
6. Human retinal pericytes, passage 4 (pericytes)

Cells were washed once with ice cold binding buffer (RPMI containing 0.1% BSA, 20 mM Tris:HCl, pH 7.2) and then 250 μl of the following solutions were added to each of three wells of the culture dishes containing the test cells.

Binding solutions were prepared in 5 mL of binding buffer with 10 ng/mL $^{125}$I-zvegf3 and:

1. No addition.
2. One μg/mL zvegf3.
3. One μg/mL VEGF (R&D Systems, Minneapolis, Minn.).
4. One μg/mL PDGF-BB.
5. Five μg/mL PDGF receptor α (R&D Systems).
6. Five μg/mL PDGF receptor β (as IgG Fc-receptor extracellular domain fusion).

The reaction mixtures were incubated on ice for 2 hours, then washed three times with one mL of ice-cold binding buffer. The bound $^{125}$I-zvegf3 was quantitated by gamma counting a NaOH extract of the cells.

Figure 5:
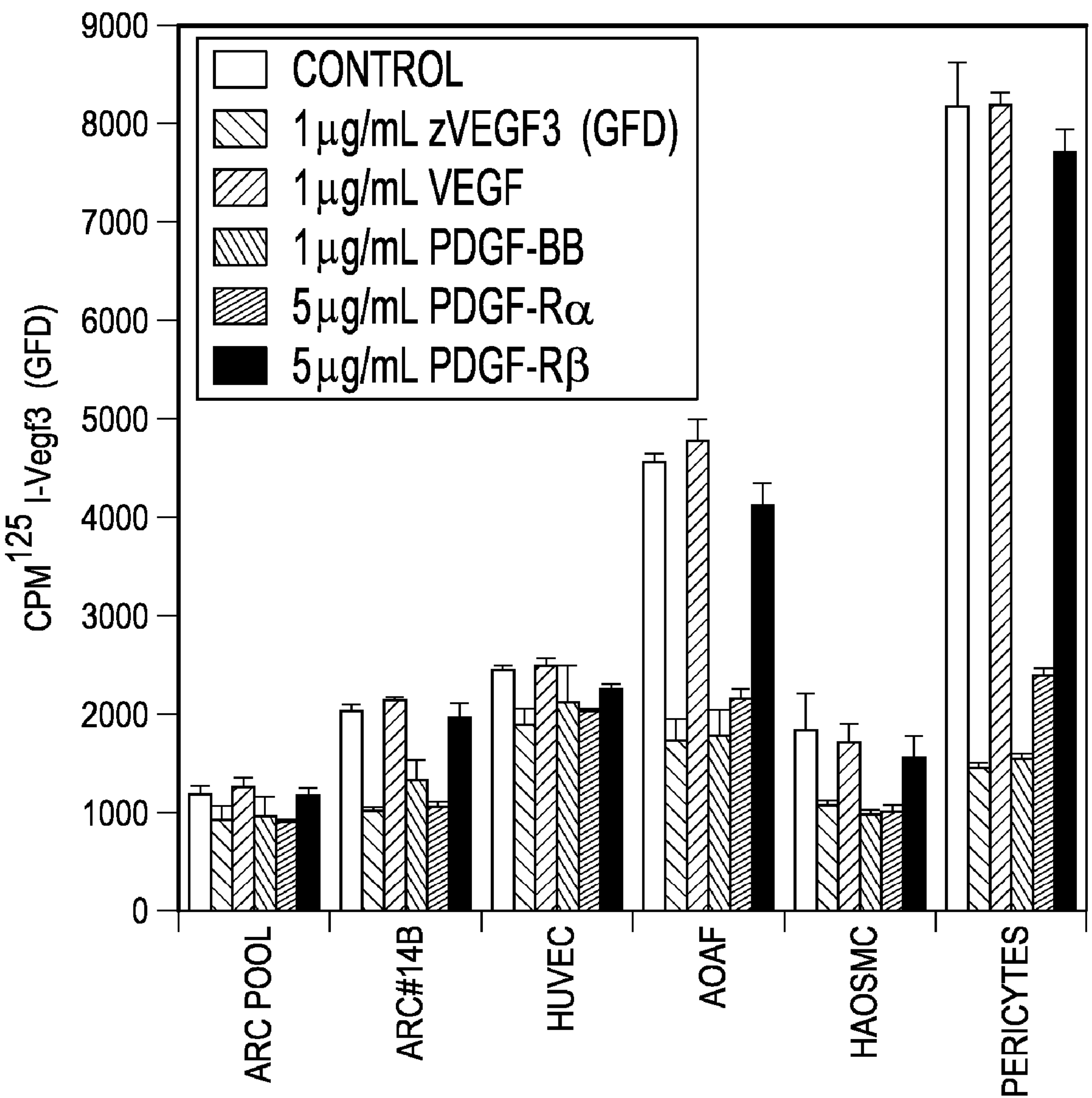
FIG. 5 shows the results of a receptor binding assay for zvegf3.

Results, shown in FIG. 5, indicate binding of zvegf3 to the PDGF receptor α. The data are graphed as $^{125}$I-zvegf3 bound/well. The error bars represent standard deviations.

The experiment was repeated with the addition of rat liver stellate cells, passage 6 (Greenwel et al., *Laboratory Investigation* 69:210-216, 1993). Stellate cells bound zvegf3 at a level comparable to pericytes.

Example 25

Binding of recombinant zvegf3 to PDGF alpha and beta receptors was measured by mass spectrometry using a surface-enhanced laser desorption and ionization (SELDI) instrument (ProteinChip™, Ciphergen Biosystems, Palo Alto, Calif.). For this experiment an 8-spot, preactivated surface array was used. To this amine-activated chip, protein-A (Zymed Laboratories, Inc., San Francisco, Calif.) was added at a concentration of 1 mg/ml, and the chip was incubated at 4° C. for four hours. After blocking with 1M ethanolamine pH 8.0 and subsequent washes (once in 0.1% Triton X-100 in PBS; once in 100 mM Na Acetate, pH4.5, 0.5 M NaCl; once in 100 mM Tris-HCl, pH8.5, 0.5 M NaCl; once in PBS), IgG Fc-receptor extracellular domain fusion proteins (PDGF alpha receptor, PDGF beta receptor, or unrelated control receptor) were added, and the chip was incubated at 4° C. overnight. After three washes in PBS, 250 μl of zvegf3 (300 ng/ml), PDGF-AA, or PDGF-BB was added, and the chip was incubated overnight at 4° C. The chip was washed twice with 0.05% Triton X100, 100 mM HEPES pH 7.2, then twice with deionized water. The chip was allowed to dry at room temperature before two additions of 0.3 microliters of sinapinic acid (Ciphergen Biosystems) in a 50:50 mixture of acetonitrile and 1% trifluroacetic acid. Ligands that bound receptor were retained on the chip after washing and subsequently detected by mass spectrometry. Assignment of a+or − for binding was made by comparing the PDGF receptor mass spectrometry profile to that of an Fc only control for each ligand. Data are shown in Table 11.

TABLE 11

| | PDGF AA | PDGF AB | PDGF BB | ZVEGF3 |
|---|---|---|---|---|
| PDGFR-alpha/Fc | + | + | + | + |
| PDGFR-beta/Fc | +/− | +/− | + | − |

Example 26

Northern blot analysis was performed with poly(A) RNA from human vascular cell lines HUVEC (human umbilical vein endothelial cells; Cascade Biologics, Inc., Portland, Oreg.), HPAEC (human pulmonary artery endothelial cells; Cascade Biologics), HAEC (human aortic endothelial cells; Cascade Biologics), AoSMC (aortic smooth muscle cells; Clonetics Corporation, Walkersville, Md.), UASMC (umbilical artery smooth muscle cells; Clonetics Corp.), HISM (human intestinal smooth muscle; American Type Culture Collection, CRL 7130), SK5 (human dermal fibroblast cells; obtained from Dr. Russel Ross, University of Washington), NHLF (normal human lung fibroblasts; Clonetics Corp.), NHDF-neo (normal human dermal fibroblast-neonatal; Clonetics Corp.); and from leukemia cell lines Daudi, Raji, Molt-4, K562 (all obtained from Clontech Laboratories, Inc.), HL60, Jurkat, and Hut 78. RNA was loaded at 2 μg per lane. An approximately 490b p DNA probe was generated by digestion of a full-length zVEGF3 clone with PvuI and StuI. The DNA probe was electrophoresed and purified using a spin column containing a silica gel membrane (QIAquick™ Gel Extraction Kit; Qiagen, Inc., Valencia, Calif. ). The probe was radioactively labeled with $^{32}$P using a commercially available kit (Rediprime™ II random-prime labeling system; Amersham Corp., Arlington Heights, Ill.) according to the manufacturer's specifications. The probe was purified using a push column. Expresshyb (Clontech, Palo Alto, Calif.) solution was used for the hybridizing solution for the blots. Hybridization took place overnight at 65° C. in a commercially available hybridization solution (ExpressHyb™ Hybridization Solution; Clontech Laboratories, Inc., Palo Alto, Calif.). The blots were then washed four times in 2×SCC and 0.1% SDS at room temperature, followed by two washes in 0.1×SSC and 0.1% SDS at 50° C. One transcript size was detected at approximately 4 kb in NHLF, NHDF-neo, SK5, UASMC, HAEC, AoSMC, Jurkat, Hut78. Signal intensity was highest for UASMC, SK5, NHLF, and NHDF-neo.

Example 27

The effects of zvegf3 on vascular endothelial regeneration and intimal hyperplasia are tested in a balloon injured rat carotid artery model. Adenovirus is used as a delivery vector.

To determine the infectivity of adenovirus and the level of gene expression obtained in the vascular wall, rats are balloon injured as disclosed below and infused with an adenovirus vector comprising an expression unit for green fluourescent protein (GFP). Three groups of three rats each are infused with doses of $1.5\times10^{10}$ pfu/ml, $3\times10^{10}$ pfu/ml, and $6\times10^{10}$ pfu/ml. Injured and uninjured carotids are harvested 48 hours after infection and fixed in 10% buffered formalin for 24 hrs. The tissue is processed and analyzed using an anti-GFP antibody to determine % infectivity.

The effects of zvegf3 are determined in a 14-day study using the optimal dose determined from the GFP study. Two groups of 14 animals each are balloon-injured and infected with either zvegf3 adenovirus or control adenovirus. The left common carotid is isolated, and the flow of blood through the vessel is stopped by tying off the internal carotid, the external carotid, and proximally, the common carotid. An arteriotomy is made between the tie on the external carotid and the bifurcation, and the vessel is rinsed out with lactated Ringer's. A 2F-embolectomy catheter is inserted, inflated, and removed, while twisting, to remove endothelial cells; this procedure is done three times. The vessel is then rinsed again, and approximately 50 μl of adenovirus solution is injected into it using a catheter of silastic tubing. The catheter is tied into the vessel just distal to the bifurcation and left in place for approximately 20 minutes. The catheter is then removed, and the vessel is flushed briefly with blood by loosening the proximal tie. A tie is made just distal to the bifurcation. Blood flow is restored by removing the tie on the internal carotid and the proximal tie on the common carotid. The ties on the external carotid remain. To determine zvegf3 protein production in the vessel wall, two animals from each group are sacrificed on days one and seven. Tissues are processed for immunohistochemical analysis and Western blotting analysis. For immunohistochemical analysis, tissues are kept in formalin for 24 hours, then transferred to 70% ethyl alcohol. For Western blotting analysis, tissues are flash frozen and stored at −80° C. At thirteen days animals are given BrdU tablets subcutaneously. At fourteen days (24 hours after BrdU insertion) Evan's Blue dye is given intravenously to stain for non-endothelialized segments, and the animals are bled and sacrificed. Animals are then exsanguinated and perfusion-fixed with 10% buffered formalin. Both carotids, liver, kidney and spleen are harvested. The carotids are visually inspected, and re-endothelialization is quantitated by measuring the distance from the bifurcation to the distal dye (white/blue) boundary. All tissue are kept in formalin for 24 hours then transferred to 70% ethyl alcohol. The carotids are sectioned into three pieces each and embedded in paraffin blocks. The liver, kidney, and spleen are visually inspected and processed. Slides are made of cross-sections of the carotids and stained with Hematoxylin and Eosin, then measured using the SPOT® diagnostic program (Diagnostic Instruments, Inc., Sterling Heights, Mich.). Measurements include the length of the internal elastic lamina and the areas of the media, intima, and lumen. ICC analysis includes the number of infected cells (using anti-gfp antibodies), cell proliferation (BrdU labeling), and % cell death.

A third study is conducted to determine the time course of zvegf3 gene expression 10 following balloon injury. Carotids are harvested from balloon-injured animals (5 animals/time point) at T=0 (non-injured), T=6 hrs, 1, 4, 7, and 14 days. The carotids are flash-frozen and stored at −80° C. for Northern blot analysis.

Example 28

An expression plasmid containing a polynucleotide encoding human zvegf3 fused N-terminally to maltose binding protein (MBP) was constructed via homologous recombination.

A fragment of human zvegf3 cDNA was isolated using PCR. Two primers were used in the production of the human zvegf3 fragment in a PCR reaction. Primer ZC20,572 (SEQ ID NO:44), contained 40 bp of vector flanking sequence and 25 bp corresponding to the amino terminus of human zvegf3, and primer ZC20,573 (SEQ ID NO:45) contained 40 bp of the 3' end corresponding to flanking vector sequence and 25 bp corresponding to the carboxyl terminus of human zvegf3. The PCR reaction conditions were 25 cycles of 94° C. for 30 seconds, 50° C. for 30 seconds, and 72° C. for 1.5 minutes; followed by 4° C. soak, run in duplicate. A 2-μl aliquot of the 100-μl reaction mixture was run on a 1.0% agarose gel with Tris/borate/EDTA buffer for analysis, and the expected band of approximately 1000 bp was seen. The remaining 90 μl of the reaction mixture was combined with the second PCR tube precipitated with 400 μl of absolute ethanol to be used for recombining into the Smal-cut recipient vector pTAP98 to produce the construct encoding the MBP-zvegf3 fusion.

Plasmid pTAP98 was derived from the plasmids pRS316 (a *Saccharomyces cerevisiae* shuttle vector; see, Hieter and Sikorski, *Genetics* 122:19-27, 1989) and pMAL™-c2X (New England Biolabs; Beverly, Mass.). The latter vector carries the tac promoter driving MalE (gene encoding MBP) followed by a His tag, a thrombin cleavage site, a cloning site, and the rrnB terminator. The vector pTAP98 was constructed using yeast homologous recombination. 100 ng of EcoRI-cut pMAL™-c2X was recombined with 1 μg PvuI-cut pRS316, 1 μg linker, and 1 μg ScaI/EcoRI-cut pRS316. The linker was constructued by combining oligonucleotides ZC19,372 (SEQ ID NO:46) (100 pmole), ZC19,351 (SEQ ID NO:47) (1 pmole), ZC19,352 (SEQ ID NO:48) (1 pmole), and ZC19, 371 (SEQ ID NO:49) (100 pmole) in a PCR reaction for 10 cycles of 94° C. for 30 seconds, 50° C. for 30 seconds, and 72° C. for 30 seconds; followed by 4° C. soak. PCR products were concentrated via 100% ethanol precipitation.

A vector containing the MBP-zvegf3 fusion sequence was constructed by homologous recombination. One hundred microliters of competent yeast cells (*S. cerevisiae*) were combined with 10 μl of a mixture containing approximately 1 μg of the human zvegf3 insert and 100 ng of SmaI digested pTAP98 vector, and transferred to a 0.2-cm electroporation cuvette. The yeast/DNA mixture was electropulsed at 0.75 kV (5 kV/cm), infinite ohms, 25 μF. To each cuvette was added 600 μl of 1.2 M sorbitol. The yeast was then plated in two 300-μl aliquots onto two -URA D plates and incubated at 30° C. After about 48 hours, the $Ura^+$ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid-washed glass beads and 200 μl phenol-chloroform, vortexed for 1 minute intervals two or three times, followed by a 5 minute spin in a microcentrifuge at maximum speed. Three hundred microliters of the aqueous phase was transferred to a fresh tube, and the DNA was precipitated with 600 μl ethanol (EtOH), then centrifuged for 10 minutes at 4° C. The DNA pellet was resuspended in 100 μl $H_2O$. Electrocompetent *E. coli* cells (MC1061; Casadaban et. al., *J. Mol. Biol.* 138: 179-207) were transformed with 1 μl of the yeast DNA prep in a volume of 40 μl. The cells were electropulsed at 2.0 kV, 25 μF, 400 ohms. Following electroporation, 0.6 ml SOC (2% Bacto™ Tryptone (Difco Laboratories, Detroit, Mich.), 0.5% yeast extract (Difco Laboratories), 10 mM NaCl, 2.5 mM KCl, 10 mM $MgCl_2$, 10 mM $MgSO_4$, 20 mM glucose) was plated in one aliquot on LB AMP plates (LB broth (Lennox), 1.8% agar (Bacto™; Difco Laboratories), 100 mg/L ampicillin). Individual clones harboring the correct expression construct for zvegf3 were identified by expression. Cells were grown in minimal medium supplemented with casamino acids and 100 μg/ml of ampicillin overnight. 50 μl of the overnight culture was used to inoculate 2 ml of fresh medium. Cultures were grown at 37° C., shaking for 2 hours. One ml of the culture was induced with 1 mM IPTG. 2-4 hours later 250 μl of each culture was mixed with 250 μl acid-washed glass beads and 250 μl Thorner buffer (8 M urea, 100 mM Tris pH 7.0, 10% glycerol, 2 mM EDTA, 5% SDS) supplemented with 5% β-ME and dye. Samples were vortexed for one minute and heated to 65° C. for 5-10 minutes. 20 μl was loaded per lane on a 4%-12% PAGE gel (NOVEX, San Diego, Calif.). Gels were run in 1× MES buffer. The positive clones were designated pCZR236 and subjected to sequence analysis. The polynucleotide sequence of the MBP-zvegf3 fusion in pCZR236 is shown in SEQ ID NO:50.

To express the fusion protein, 1 μl of sequencing DNA was used to transform *E. coli* strain W3110 (obtained from American Type Culture Collection, Manassas, Va.). The cells were electropulsed at 2.0 kV, 25 μF and 400 ohms. Following electroporation, 0.6 ml SOC (2% Bacto™ Tryptone (Difco Laboratories), 0.5% yeast extract (Difco Laboratories), 10 mM NaCl, 2.5 mM KCl, 10 mM MgCl2, 10 mM MgSO4, 20 mM glucose) was plated in one aliquot on LB AMP plates (LB broth (Lennox), 1.8% Bacto™ Agar (Difco Laboratories), 100 mg/L ampicillin). Cells were picked from the plate and grown in minimal medium containing casamino acids overnight. A 50-μl aliquot of the overnight culture was used to inoculate 2 ml of fresh medium. Cultures were grown at 37° C. with shaking for 2 hours. One ml of the culture was induced with 1 mM IPTG, and the cells were lysed essentially as described above. Twenty-μl aliquots of the lysate were analyzed by gel electrophoresis as described above.

Example 29

Recombinant zvegf3 was analyzed for mitogenic activity on rat stellate cells (obtained from N. Fausto, University Of Washington). Stellate cells were plated at a density of 2,000 cells/well in 96-well culture plates and grown for approximately 72 hours in DMEM containing 10% fetal calf serum at 37° C. Cells were quiesced by incubating them for 20 hours in serum-free DMEM/Ham's F-12 medium containing insulin (5 μg/ml), transferrin (20 μg/ml), and selenium (16 pg/ml) (ITS). At the time of the assay, the medium was removed, and test samples were added to the wells in triplicate. Test samples consisted of either conditioned media (CM) from adenovirally-infected HaCaT human keratinocyte cells (Boukamp et al., *J. Cell. Biol.* 106:761-771, 1988) expressing full-length zvegf3, purified growth factor domain expressed in BHK cells, or control media from cells infected with parental adenovirus (Zpar) containing an expression unit for green fluorescent protein. The CM was concentrated 10-fold using a 15-ml centrifugal filter device with a 10K membrane filter (Ultrafree®; Millipore Corp., Bedford, Mass.), then diluted back to 3× with ITS medium and added to the cells. Purified protein in a buffer containing 0.1% BSA was serially diluted into ITS medium at concentrations of 1 μg/ml to 1 ng/ml and added to the test plate. A control buffer of 0.1% BSA was diluted identically to the highest concentration of zvegf3 protein and added to the plate. For measurement of [$^3$H]thymidine incorporation, 20 μl of a 50 μCi/ml stock in DMEM was added directly to the cells, for a final activity of 1 μCi/well. After another 24-hour incubation, mitogenic activity was assessed by measuring the uptake of [$^3$H]thymidine. Media were removed, and cells were incubated with 0.1 ml of trypsin until cells detached. Cells were harvested onto 96-well filter plates using a sample harvester (FilterMate™ harvester; Packard Instrument Co., Meriden, CT). The plates were then dried at 65° C. for 15 minutes, sealed after adding 40 μl/well scintillation cocktail (Microscint™ O; Packard Instrument Co.) and counted on a microplate scintillation counter (Topcount®; Packard Instrument Co.).

Results, presented in Table 12, demonstrated that zvegf3 CM had approximately 4.4-fold higher mitogenic activity on stellate cells over control CM, and purified protein at 100 ng/ml caused a maximal 14-fold increase in [$^3$H]thymidine incorporation over the buffer control.

TABLE 12

| Sample | CPM Incorporated Mean | St. dev. |
|---|---|---|
| zvegf3 (2x CM) | 42489 | 1306 |
| Zpar (2x CM) | 9629 | 540 |
| zvegf3 GF domain, 100 ng/ml | 77540 | 4142 |
| zvegf3 GF domain, 33.3 ng/ml | 74466 | 18142 |
| zvegf3 GF domain, 11.1 ng/ml | 52462 | 6239 |
| zvegf3 GF domain, 3.7 ng/ml | 15128 | 4989 |
| Buffer control | 5618 | 573 |
| PDGF-BB 20 ng/ml | 19741 | 2075 |
| PDGF-AA 20 ng/ml | 33133 | 3325 |
| Media alone (basal response) | 6765 | 226 |

Example 30

Binding of recombinant zvegf3 growth factor domain (produced in BHK cells) to PDGF receptors was assessed in a radioimmune precipitation assay. Proteins were iodinated using a solution of PBS containing Na-$^{125}$I (Amersham Corp.). One derivatized, nonporous polystyrene bead (IODO-Beads®; Pierce Chemical Co., Rockford, Ill.) was added, and the reaction mixture was incubated one minute on ice. The iodinated protein was separated from unicorporated $^{125}$I by gel filtration using PBS containing 0.25% gelatin as the elution buffer.

Baby hamster kidney (BHK) cells transfected to express both the PDGF α and β receptor subunits were cultured until confluency in 6-well dishes (Costar®; Corning, Corning, N.Y.). Growth medium was removed, and the cells were washed once with ice-cold binding buffer consisting of HAM'S F-12 media (Life Technologies, Gaithersburg, Md.) containing 2.5 mg/ml BSA (Sigma, St. Louis, Mo.) and 20 mM HEPES, pH 7.2 (Life Technologies). Binding solutions were prepared in room temperature binding buffer with 40 ng/ml of either $^{125}$I-zvegf3, $^{125}$I-PDGF AA, or $^{125}$I-PDGF BB. One ml of binding solution was added to each of three wells of culture dishes containing the test cells. Reaction mixtures were incubated at room temperature for 10 minutes, then washed four times with 1 ml of ice-cold PBS (Life Technologies).

Receptor-ligand complexes were crosslinked by the addition of 1 ml of 3 mM momobifunctional crosslinker (BS$^3$; Pierce, Rockford, Ill.) crosslinking solution. Reaction mixtures were incubated on ice for 30 minutes before quenching the reaction by rinsing cells three times in ice-cold Tris-buffered saline.

Cells were extracted in 1 ml/well of TNEN buffer (20 mM Tris base, 100 mM NaCl, 1 mM EDTA, 0.5% Igepal®-CA630), and cellular extracts were pre-cleared with 40 μl/ml Protein G Plus/Protein A-Agarose (Calbiochem, San Diego, Calif.). To each of the three 1 ml cell extracts containing $^{125}$I-zvegf, -PDGF AA, or -PDGF BB, one of the following antibodies was added at 4 μg/ml:

1. Mouse anti-PDGF α Receptor, clone 169.5.2.2.1 (Tiesman and Hart, *J. Biol. Chem.* 268:9621-9628, 1993)
2. Mouse anti-PDGF α Receptor, clone 7212 (Hart et al., *J. Biol. Chem.* 262:10780-10785, 1987)
3. Normal Mouse IgG The solutions were rocked at room temperature for 1 hour. An additional 40 μl of Protein G Plus/Protein A Agarose was added to each solution, and the solutions were rocked at room temperature for 1.5 hours.

The agarose was pelleted by centrifugation, and the pellets were rinsed 3 times in PBS+1% BSA. After the final rinse, supernatants were removed, and 50 μl of reducing sample buffer was added to each pellet. The solutions were boiled for 5 minutes and pelleted again. The sample buffer was removed, 5-μl aliquots were gamma counted, and 25-μl aliquots were electrophoresed on a 4-12% BisTris 12-lane SDS gel (NuPage™ pre-cast gel; Invitrogen, Carlsbad, Calif.). Gels were dried and exposed to film for 1 week.

Results (Table 13) indicated that zvegf3 bound the PDGF αβ receptor dimer as well as the αα dimer. Counts were above background when $^{125}$I-zvegf3 was bound and immunoprecipitated with the anti-PDGF β receptor antibody, and there was a clear band around 180 kD when this sample was run on a gel and exposed to film.

TABLE 13

| $^{125}$I-Ligand | Antibody | CPM/5-μl sample |
|---|---|---|
| Zvegf3 | Anti-α Receptor | 1271 |
| Zvegf3 | Anti-β Receptor | 134 |
| Zvegf3 | Normal Mouse IgG | 12 |
| PDGF AA | Anti-α Receptor | 1374 |
| PDGF AA | Anti-β Receptor | 29 |
| PDGF AA | Normal Mouse IgG | 0 |

TABLE 13-continued

| $^{125}$I-Ligand | Antibody | CPM/5-μl sample |
|---|---|---|
| PDGF BB | Anti-α Receptor | 15 |
| PDGF BB | Anti-β Receptor | 58 |

Example 31

Recombinant zvegf3 growth factor domain (GFD) from BHK cells was tested for the ability to induce phosphorylation of PDGF receptors expressed in baby hamster kidney cells. BHK cells expressing α receptor, β receptor, or both α and β receptor were grown to ~75% confluency in 6-well plates, and quiesced overnight in DMEM/F-12 containing 5 μg/ml insulin, 20 μg/ml transferrin, 16 pg/ml selenium, and 20 mM HEPES. The plates were equilibrated to ambient temperature for 20 minutes, then the cells were treated in quadruplicate with 50 ng/ml of PDGF-AA, PDGF-BB, zvegf3 GFD or control (conditioned medium from cells transfected with a zveg4 expression vector or a control vector) for 10 minutes at ambient temperature on a rotary shaker (1 Hz). After treatment, plates were immediately placed on ice, rinsed once with ice-cold PBS/1mM $Na_3VO_4$, and the cells were lysed by incubation on ice for 15 minutes in 1 ml TNE (20 mM Tris pH 7.7, 100 mM NaCl, 5 mM EDTA, 0.1% t-Octylphenoxypolyethoxyethanol (Triton X-100), 0.05% octylphenylpolyethylene glycol (Igepal®-CA630), 1 mM $Na_3VO_4$). The lysates were cleared of cellular debris through plastic centrifuge tube filters (Costar® Spin-X® tube filters; Corning). After preclearing lysates with Protein G Plus/Protein A-Agarose beads (Calbiochem), ~2 ml of lysate (400 μg total protein) from each treatment was incubated with 5 μg of either anti-PDGF-Rα, anti-PDGF -Rβ, or normal mouse IgG for 3 hours at 4° C., followed by an overnight 4° C. incubation with Protein G Plus/Protein A-Agarose beads. The beads were collected, rinsed three times in TNEN and once in PBS, and resuspended in ~100 μl of reducing sample buffer (NuPAGE® buffer; Invitrogen). Samples were boiled for 10 minutes, electrophoresed on a 4-12% Bis-Tris gel (NuPAGE® pre-cast gel; Invitrogen) in pre-mixed buffer (NuPAGE® MOPS SDS Running Buffer; Invitrogen), and transferred to a 0.45μnitrocellulose membrane. The membrane was subsequently blocked and probed with HRP-conjugated anti-phosphotyrosine antibody (PY-Plus™; Zymed Laboratories Inc., South San Francisco, CA), and tyrosine phosphorylated proteins were detected using a commercially available chemiluminscent substrate (Lumi-Light; Roche Molecular Biochemicals, Indianapolis, Ind.).

As shown in Table 14, zvegf3 GFD appeared to phosphorylate tyrosine residues of both the alpha and beta PDGF receptors in the BHK/αβ19 cell line.

TABLE 14

| | BHK/αβ19 | BHK/α1-10 | BHK/β Clone 5 |
|---|---|---|---|
| PDGF-AA | + | + | N/D |
| PDGF-BB | ++ | N/D | + |
| zvegf3gf | ++ | ++ | − |
| HaCaT/zvegf4 CM | N/D | + | − |
| HaCaT/zpar CM | N/D | + | − |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A dimeric protein having two polypeptide chains, wherein each of the polypeptide chains is from 111 to 136 amino acid residues in length and comprises a sequence of amino acid residues having at least 95% sequence identity with residues 235-345 of SEQ ID NO:2, wherein the protein is optionally glycosylated, and wherein the protein has mitogenic activity on human aortic smooth muscle cells.

2. The protein of claim 1 which is glycosylated.

3. The protein of claim 1 wherein each of the polypeptide chains consists of a sequence of amino acid residues selected from the group consisting of:

residues 230-345 of SEQ ID NO:2;
residues 231-345 of SEQ ID NO:2;
residues 232-345 of SEQ ID NO:2;
residues 233-345 of SEQ ID NO:2;
residues 234-345 of SEQ ID NO:2;
residues 235-345 of SEQ ID NO:2;
residues 236-345 of SEQ ID NO:2;
residues 237-345 of SEQ ID NO:2;
residues 238-345 of SEQ ID NO:2;
residues 239-345 of SEQ ID NO:2; and
residues 240-345 of SEQ ID NO:2.

4. The protein of claim 3 which is glycosylated.

5. A composition comprising the protein of claim 1 in combination with a pharmaceutically acceptable vehicle.

6. The composition of claim 5 wherein the protein is glycosylated.

7. The composition of claim 5 wherein each of the polypeptide chains consists of a sequence of amino acid residues selected from the group consisting of:

residues 230-345 of SEQ ID NO:2;
residues 231-345 of SEQ ID NO:2;
residues 232-345 of SEQ ID NO:2;

residues 233-345 of SEQ ID NO:2;
residues 234-345 of SEQ ID NO:2;
residues 235-345 of SEQ ID NO:2;
residues 236-345 of SEQ ID NO:2;
residues 237-345 of SEQ ID NO:2;
residues 238-345 of SEQ ID NO:2;
residues 239-345 of SEQ ID NO:2; and
residues 240-345 of SEQ TD NO:2.

8. The composition of claim 7 wherein the protein is glycosylated.

* * * * *

SEQUENCE LISTING

```
<160> NUMBER OF SEQ ID NOS: 50

<210> SEQ ID NO 1
<211> LENGTH: 1760
<212> TYPE: DNA
<213> ORGANISM: Homo sapiens
<220> FEATURE:
<221> NAME/KEY: CDS
<222> LOCATION: (154)...(1191)

<400> SEQUENCE: 1

attatgtgga aactaccctg cgattctctg ctgccagagc aggctcggcg cttccacccc     60

agtgcagcct tcccctggcg gtggtgaaag agactcggga gtcgctgctt ccaaagtgcc    120

cgccgtgagt gagctctcac cccagtcagc caa atg agc ctc ttc ggg ctt ctc     174
                                     Met Ser Leu Phe Gly Leu Leu
                                      1               5

ctg ctg aca tct gcc ctg gcc ggc cag aga cag ggg act cag gcg gaa      222
Leu Leu Thr Ser Ala Leu Ala Gly Gln Arg Gln Gly Thr Gln Ala Glu
        10                  15                  20

tcc aac ctg agt agt aaa ttc cag ttt tcc agc aac aag gaa cag aac      270
Ser Asn Leu Ser Ser Lys Phe Gln Phe Ser Ser Asn Lys Glu Gln Asn
    25                  30                  35

gga gta caa gat cct cag cat gag aga att att act gtg tct act aat      318
Gly Val Gln Asp Pro Gln His Glu Arg Ile Ile Thr Val Ser Thr Asn
 40                  45                  50                  55
```

-continued

```
gga agt att cac agc cca agg ttt cct cat act tat cca aga aat acg      366
Gly Ser Ile His Ser Pro Arg Phe Pro His Thr Tyr Pro Arg Asn Thr
                 60                  65                  70

gtc ttg gta tgg aga tta gta gca gta gag gaa aat gta tgg ata caa      414
Val Leu Val Trp Arg Leu Val Ala Val Glu Glu Asn Val Trp Ile Gln
             75                  80                  85

ctt acg ttt gat gaa aga ttt ggg ctt gaa gac cca gaa gat gac ata      462
Leu Thr Phe Asp Glu Arg Phe Gly Leu Glu Asp Pro Glu Asp Asp Ile
         90                  95                 100

tgc aag tat gat ttt gta gaa gtt gag gaa ccc agt gat gga act ata      510
Cys Lys Tyr Asp Phe Val Glu Val Glu Glu Pro Ser Asp Gly Thr Ile
    105                 110                 115

tta ggg cgc tgg tgt ggt tct ggt act gta cca gga aaa cag att tct      558
Leu Gly Arg Trp Cys Gly Ser Gly Thr Val Pro Gly Lys Gln Ile Ser
120                 125                 130                 135

aaa gga aat caa att agg ata aga ttt gta tct gat gaa tat ttt cct      606
Lys Gly Asn Gln Ile Arg Ile Arg Phe Val Ser Asp Glu Tyr Phe Pro
                140                 145                 150

tct gaa cca ggg ttc tgc atc cac tac aac att gtc atg cca caa ttc      654
Ser Glu Pro Gly Phe Cys Ile His Tyr Asn Ile Val Met Pro Gln Phe
            155                 160                 165

aca gaa gct gtg agt cct tca gtg cta ccc cct tca gct ttg cca ctg      702
Thr Glu Ala Val Ser Pro Ser Val Leu Pro Pro Ser Ala Leu Pro Leu
        170                 175                 180

gac ctg ctt aat aat gct ata act gcc ttt agt acc ttg gaa gac ctt      750
Asp Leu Leu Asn Asn Ala Ile Thr Ala Phe Ser Thr Leu Glu Asp Leu
    185                 190                 195

att cga tat ctt gaa cca gag aga tgg cag ttg gac tta gaa gat cta      798
Ile Arg Tyr Leu Glu Pro Glu Arg Trp Gln Leu Asp Leu Glu Asp Leu
200                 205                 210                 215

tat agg cca act tgg caa ctt ctt ggc aag gct ttt gtt ttt gga aga      846
Tyr Arg Pro Thr Trp Gln Leu Leu Gly Lys Ala Phe Val Phe Gly Arg
                220                 225                 230

aaa tcc aga gtg gtg gat ctg aac ctt cta aca gag gag gta aga tta      894
Lys Ser Arg Val Val Asp Leu Asn Leu Leu Thr Glu Glu Val Arg Leu
            235                 240                 245

tac agc tgc aca cct cgt aac ttc tca gtg tcc ata agg gaa gaa cta      942
Tyr Ser Cys Thr Pro Arg Asn Phe Ser Val Ser Ile Arg Glu Glu Leu
        250                 255                 260

aag aga acc gat acc att ttc tgg cca ggt tgt ctc ctg gtt aaa cgc      990
Lys Arg Thr Asp Thr Ile Phe Trp Pro Gly Cys Leu Leu Val Lys Arg
    265                 270                 275

tgt ggt ggg aac tgt gcc tgt tgt ctc cac aat tgc aat gaa tgt caa     1038
Cys Gly Gly Asn Cys Ala Cys Cys Leu His Asn Cys Asn Glu Cys Gln
280                 285                 290                 295

tgt gtc cca agc aaa gtt act aaa aaa tac cac gag gtc ctt cag ttg     1086
Cys Val Pro Ser Lys Val Thr Lys Lys Tyr His Glu Val Leu Gln Leu
                300                 305                 310

aga cca aag acc ggt gtc agg gga ttg cac aaa tca ctc acc gac gtg     1134
Arg Pro Lys Thr Gly Val Arg Gly Leu His Lys Ser Leu Thr Asp Val
            315                 320                 325

gcc ctg gag cac cat gag gag tgt gac tgt gtg tgc aga ggg agc aca     1182
Ala Leu Glu His His Glu Glu Cys Asp Cys Val Cys Arg Gly Ser Thr
        330                 335                 340

gga gga tag ccgcatcacc accagcagct cttgcccaga gctgtgcagt             1231
Gly Gly
    345

gcagtggctg attctattag agaacgtatg cgttatctcc atccttaatc tcagttgttt   1291
```

-continued

```
gcttcaagga cctttcatct tcaggattta cagtgcattc tgaaagagga gacatcaaac   1351

agaattagga gttgtgcaac agctcttttg agaggaggcc taaaggacag gagaaaaggt   1411

cttcaatcgt ggaaagaaaa ttaaatgttg tattaaatag atcaccagct agtttcagag   1471

ttaccatgta cgtattccac tagctgggtt ctgtatttca gttctttcga tacggcttag   1531

ggtaatgtca gtacaggaaa aaaactgtgc aagtgagcac ctgattccgt tgccttgctt   1591

aactctaaag ctccatgtcc tgggcctaaa atcgtataaa atctggattt ttttttttt    1651

tttttgctca tattcacata tgtaaaccag aacattctat gtactacaaa cctggttttt   1711

aaaaaggaac tatgttgcta tgaattaaac ttgtgtcgtg ctgatagga               1760


<210> SEQ ID NO 2
<211> LENGTH: 345
<212> TYPE: PRT
<213> ORGANISM: Homo sapiens

<400> SEQUENCE: 2

Met Ser Leu Phe Gly Leu Leu Leu Leu Thr Ser Ala Leu Ala Gly Gln
 1               5                  10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
```

```
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345


<210> SEQ ID NO 3
<211> LENGTH: 116
<212> TYPE: PRT
<213> ORGANISM: Artificial Sequence
<220> FEATURE:
<223> OTHER INFORMATION: peptide motif
<220> FEATURE:
<221> NAME/KEY: VARIANT
<222> LOCATION: (2)...(19)
<223> OTHER INFORMATION: Xaa is any amino acid
<220> FEATURE:
<221> NAME/KEY: VARIANT
<222> LOCATION: (20)...(34)
<223> OTHER INFORMATION: Xaa is any amino acid or not present
<220> FEATURE:
<221> NAME/KEY: VARIANT
<222> LOCATION: (36)...(36)
<223> OTHER INFORMATION: Xaa is any amino acid
<220> FEATURE:
<221> NAME/KEY: VARIANT
<222> LOCATION: (38)...(38)
<223> OTHER INFORMATION: Xaa is any amino acid
<220> FEATURE:
<221> NAME/KEY: VARIANT
<222> LOCATION: (40)...(45)
<223> OTHER INFORMATION: Xaa is any amino acid
<220> FEATURE:
<221> NAME/KEY: VARIANT
<222> LOCATION: (46)...(72)
<223> OTHER INFORMATION: Xaa is any amino acid or not present
<220> FEATURE:
<221> NAME/KEY: VARIANT
<222> LOCATION: (74)...(93)
<223> OTHER INFORMATION: Xaa is any amino acid
<220> FEATURE:
<221> NAME/KEY: VARIANT
<222> LOCATION: (94)...(113)
<223> OTHER INFORMATION: Xaa is any amino acid not present
<220> FEATURE:
<221> NAME/KEY: VARIANT
<222> LOCATION: (115)...(115)
<223> OTHER INFORMATION: Xaa is any amino acid

<400> SEQUENCE: 3

Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Cys Xaa Gly Xaa Cys Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Cys Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Cys Xaa Cys
```

115

<210> SEQ ID NO 4
<211> LENGTH: 24
<212> TYPE: PRT
<213> ORGANISM: Artificial Sequence
<220> FEATURE:
<223> OTHER INFORMATION: peptide motif
<220> FEATURE:
<221> NAME/KEY: VARIANT
<222> LOCATION: (2)...(2)
<223> OTHER INFORMATION: Xaa is Lys or Arg
<220> FEATURE:
<221> NAME/KEY: VARIANT
<222> LOCATION: (4)...(4)
<223> OTHER INFORMATION: Xaa is Asp, Asn or Glu
<220> FEATURE:
<221> NAME/KEY: VARIANT
<222> LOCATION: (5)...(5)
<223> OTHER INFORMATION: Xaa is Trp, Tyr or Phe
<220> FEATURE:
<221> NAME/KEY: VARIANT
<222> LOCATION: (6)...(16)
<223> OTHER INFORMATION: Xaa is any amino acid
<220> FEATURE:
<221> NAME/KEY: VARIANT
<222> LOCATION: (17)...(20)
<223> OTHER INFORMATION: Xaa is any amino acid or not present
<220> FEATURE:
<221> NAME/KEY: VARIANT
<222> LOCATION: (22)...(22)
<223> OTHER INFORMATION: Xaa is Lys or Arg
<220> FEATURE:
<221> NAME/KEY: VARIANT
<222> LOCATION: (23)...(23)
<223> OTHER INFORMATION: Xaa is Trp, Tyr or Phe

<400> SEQUENCE: 4

```
Cys Xaa Tyr Xaa Xaa Xaa Xaa Xaa Xaa Xaa Xaa Xaa Xaa Xaa Xaa Xaa
 1               5                   10                  15

Xaa Xaa Xaa Xaa Gly Xaa Xaa Cys
            20
```

<210> SEQ ID NO 5
<211> LENGTH: 6
<212> TYPE: PRT
<213> ORGANISM: Artificial Sequence
<220> FEATURE:
<223> OTHER INFORMATION: peptide tag

<400> SEQUENCE: 5

```
Glu Tyr Met Pro Met Glu
 1               5
```

<210> SEQ ID NO 6
<211> LENGTH: 1035
<212> TYPE: DNA
<213> ORGANISM: Artificial Sequence
<220> FEATURE:
<223> OTHER INFORMATION: degenerate sequence derived from SEQ ID NOS: 1
      and 2
<220> FEATURE:
<221> NAME/KEY: misc_feature
<222> LOCATION: (1)...(1035)
<223> OTHER INFORMATION: n = A,T,C or G

<400> SEQUENCE: 6

```
atgwsnytnt tyggnytnyt nytnytnacn wsngcnytng cnggncarmg ncarggnacn     60

cargcngarw snaayytnws nwsnaartty carttywsnw snaayaarga rcaraayggn    120

gtncargayc cncarcayga rmgnathath acngtnwsna cnaayggnws nathcaywsn    180
```

ccnmgnttyc cncayacnta yccnmgnaay acngtnytng tntggmgnyt ngtngcngtn 240
gargaraayg tntggathca rytnacntty gaygarmgnt tyggnytnga rgayccngar 300
gaygayatht gyaartayga yttygtngar gtngargarc cnwsngaygg nacnathytn 360
ggnmgntggt gyggnwsngg nacngtnccn ggnaarcara thwsnaargg naaycarath 420
mgnathmgnt tygtnwsnga ygartaytty ccnwsngarc cnggnttytg yathcaytay 480
aayathgtna tgccncartt yacngargcn gtnwsnccnw sngtnytncc nccnwsngcn 540
ytnccnytng ayytnytnaa yaaygcnath acngcnttyw snacnytnga rgayytnath 600
mgntayytng arccngarmg ntggcarytn gayytngarg ayytntaymg nccnacntgg 660
carytnytng gnaargcntt ygtnttyggn mgnaarwsnm gngtngtnga yytnaayytn 720
ytnacngarg argtnmgnyt ntaywsntgy acnccnmgna ayttywsngt nwsnathmgn 780
gargarytna armgnacnga yacnathtty tggccnggnt gyytnytngt naarmgntgy 840
ggnggnaayt gygcntgytg yytncayaay tgyaaygart gycartgygt nccnwsnaar 900
gtnacnaara artaycayga rgtnytncar ytnmgnccna aracnggngt nmgnggnytn 960
cayaarwsny tnacngaygt ngcnytngar caycaygarg artgygaytg ygtntgymgn 1020
ggnwsnacng gnggn 1035

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 7
mgntgyggng gnaaytg 17

<210> SEQ ID NO 8
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 8
mgntgydsng gnwrytg 17

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 9
carywnccns hrcanck 17

<210> SEQ ID NO 10
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 10
ttytggccng gntgyyt 17

<210> SEQ ID NO 11
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 11
ntnddnccnn sntgybt 17

<210> SEQ ID NO 12
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 12
avrcansnng gnhhnan 17

<210> SEQ ID NO 13
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 13
caygargart gygaytg 17

<210> SEQ ID NO 14
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 14
caynnnnvnt gyvvntg 17

<210> SEQ ID NO 15
<211> LENGTH: 17

<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 15
canbbrcanb nnnnrtg 17

<210> SEQ ID NO 16
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 16
tgyacnccnm gnaaytt 17

<210> SEQ ID NO 17
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 17
tgyhnnmcnm knrmndh 17

<210> SEQ ID NO 18
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 18
dhnkynmkng knndrca 17

<210> SEQ ID NO 19
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 19
tgyaartayg aytwygt 17

<210> SEQ ID NO 20
<211> LENGTH: 17
<212> TYPE: DNA
<213> ORGANISM: Artificial Sequence
<220> FEATURE:

-continued

<223> OTHER INFORMATION: Oligonucleotide primer

<400> SEQUENCE: 20
acrwartcrt ayttrca 17

<210> SEQ ID NO 21
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 21
ywnggnmrnt dbtgygg 17

<210> SEQ ID NO 22
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 22
ccrcavhany knccnwr 17

<210> SEQ ID NO 23
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 23
tdbccnmand vntaycc 17

<210> SEQ ID NO 24
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 24
ggrtanbhnt knggvha 17

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
agcaggtcca gtggcaaagc 20

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 26
cgtttgatga aagatttggg c 21

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 27
ggaggtctat ataagcagag c 21

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 28
taacagagga ggtaagat 18

<210> SEQ ID NO 29
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 29
tcggttctct ttagttct 18

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 30
tctggacgtc ctcctgctgg tatag 25

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 31
ggtatggagc caggggcaag ttggg 25

<210> SEQ ID NO 32
<211> LENGTH: 27
<212> TYPE: DNA

-continued

```
<213> ORGANISM: Artificial Sequence
<220> FEATURE:
<223> OTHER INFORMATION: Oligonucleotide primer

<400> SEQUENCE: 32

gagtggcaac ttccagggcc aggagag                                    27


<210> SEQ ID NO 33
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 33

cttttgctag cctcaaccct gactatc                                    27


<210> SEQ ID NO 34
<211> LENGTH: 35
<212> TYPE: DNA
<213> ORGANISM: Artificial Sequence
<220> FEATURE:
<223> OTHER INFORMATION: Oligonucleotide primer ZC20,180

<400> SEQUENCE: 34

cgcgcggttt aaacgccacc atgagcctct tcggg                           35


<210> SEQ ID NO 35
<211> LENGTH: 32
<212> TYPE: DNA
<213> ORGANISM: Artificial Sequence
<220> FEATURE:
<223> OTHER INFORMATION: Oligonucleotide primer ZC20,181

<400> SEQUENCE: 35

cgtatcggcg cgccctatcc tcctgtgctc cc                              32


<210> SEQ ID NO 36
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 36

ccgtcaccat ttatcagctc agcaccacaa ggaagtgcgg cacccacacg cgctcggaaa    60

gttcagcatg caggaagttt ggggagagct cggcgattag cacagcgacc cgggccagcg   120

cagggcgagc gcaggcggcg agagcgcagg gcggcgcggc gtcggtcccg ggagcagaac   180

ccggcttttt cttggagcga cgctgtctct agtcgctgat cccaa atg cac cgg ctc   237
                                                  Met His Arg Leu
                                                   1

atc ttt gtc tac act cta atc tgc gca aac ttt tgc agc tgt cgg gac     285
Ile Phe Val Tyr Thr Leu Ile Cys Ala Asn Phe Cys Ser Cys Arg Asp
 5                  10                  15                  20

act tct gca acc ccg cag agc gca tcc atc aaa gct ttg cgc aac gcc     333
Thr Ser Ala Thr Pro Gln Ser Ala Ser Ile Lys Ala Leu Arg Asn Ala
                25                  30                  35

aac ctc agg cga gat gag agc aat cac ctc aca gac ttg tac cga aga     381
Asn Leu Arg Arg Asp Glu Ser Asn His Leu Thr Asp Leu Tyr Arg Arg
            40                  45                  50

gat gag acc atc cag gtg aaa gga aac ggc tac gtg cag agt cct aga     429
Asp Glu Thr Ile Gln Val Lys Gly Asn Gly Tyr Val Gln Ser Pro Arg
```

-continued

```
        55                  60                  65

ttc ccg aac agc tac ccc agg aac ctg ctc ctg aca tgg cgg ctt cac      477
Phe Pro Asn Ser Tyr Pro Arg Asn Leu Leu Leu Thr Trp Arg Leu His
     70                  75                  80

tct cag gag aat aca cgg ata cag cta gtg ttt gac aat cag ttt gga      525
Ser Gln Glu Asn Thr Arg Ile Gln Leu Val Phe Asp Asn Gln Phe Gly
 85                  90                  95                 100

tta gag gaa gca gaa aat gat atc tgt agg tat gat ttt gtg gaa gtt      573
Leu Glu Glu Ala Glu Asn Asp Ile Cys Arg Tyr Asp Phe Val Glu Val
                105                 110                 115

gaa gat ata tcc gaa acc agt acc att att aga gga cga tgg tgt gga      621
Glu Asp Ile Ser Glu Thr Ser Thr Ile Ile Arg Gly Arg Trp Cys Gly
            120                 125                 130

cac aag gaa gtt cct cca agg ata aaa tca aga acg aac caa att aaa      669
His Lys Glu Val Pro Pro Arg Ile Lys Ser Arg Thr Asn Gln Ile Lys
        135                 140                 145

atc aca ttc aag tcc gat gac tac ttt gtg gct aaa cct gga ttc aag      717
Ile Thr Phe Lys Ser Asp Asp Tyr Phe Val Ala Lys Pro Gly Phe Lys
    150                 155                 160

att tat tat tct ttg ctg gaa gat ttc caa ccc gca gca gct tca gag      765
Ile Tyr Tyr Ser Leu Leu Glu Asp Phe Gln Pro Ala Ala Ala Ser Glu
165                 170                 175                 180

acc aac tgg gaa tct gtc aca agc tct att tca ggg gta tcc tat aac      813
Thr Asn Trp Glu Ser Val Thr Ser Ser Ile Ser Gly Val Ser Tyr Asn
                185                 190                 195

tct cca tca gta acg gat ccc act ctg att gcg gat gct ctg gac aaa      861
Ser Pro Ser Val Thr Asp Pro Thr Leu Ile Ala Asp Ala Leu Asp Lys
            200                 205                 210

aaa att gca gaa ttt gat aca gtg gaa gat ctg ctc aag tac ttc aat      909
Lys Ile Ala Glu Phe Asp Thr Val Glu Asp Leu Leu Lys Tyr Phe Asn
        215                 220                 225

cca gag tca tgg caa gaa gat ctt gag aat atg tat ctg gac acc cct      957
Pro Glu Ser Trp Gln Glu Asp Leu Glu Asn Met Tyr Leu Asp Thr Pro
    230                 235                 240

cgg tat cga ggc agg tca tac cat gac cgg aag tca aaa gtt gac ctg     1005
Arg Tyr Arg Gly Arg Ser Tyr His Asp Arg Lys Ser Lys Val Asp Leu
245                 250                 255                 260

gat agg ctc aat gat gat gcc aag cgt tac agt tgc act ccc agg aat     1053
Asp Arg Leu Asn Asp Asp Ala Lys Arg Tyr Ser Cys Thr Pro Arg Asn
                265                 270                 275

tac tcg gtc aat ata aga gaa gag ctg aag ttg gcc aat gtg gtc ttc     1101
Tyr Ser Val Asn Ile Arg Glu Glu Leu Lys Leu Ala Asn Val Val Phe
            280                 285                 290

ttt cca cgt tgc ctc ctc gtg cag cgc tgt gga gga aat tgt ggc tgt     1149
Phe Pro Arg Cys Leu Leu Val Gln Arg Cys Gly Gly Asn Cys Gly Cys
        295                 300                 305

gga act gtc aac tgg agg tcc tgc aca tgc aat tca ggg aaa acc gtg     1197
Gly Thr Val Asn Trp Arg Ser Cys Thr Cys Asn Ser Gly Lys Thr Val
    310                 315                 320

aaa aag tat cat gag gta tta cag ttt gag cct ggc cac atc aag agg     1245
Lys Lys Tyr His Glu Val Leu Gln Phe Glu Pro Gly His Ile Lys Arg
325                 330                 335                 340

agg ggt aga gct aag acc atg gct cta gtt gac atc cag ttg gat cac     1293
Arg Gly Arg Ala Lys Thr Met Ala Leu Val Asp Ile Gln Leu Asp His
                345                 350                 355

cat gaa cga tgc gat tgt atc tgc agc tca aga cca cct cga taa         1338
His Glu Arg Cys Asp Cys Ile Cys Ser Ser Arg Pro Pro Arg
            360                 365                 370

gagaatgtgc acatccttac attaagcctg aaagaacctt tagtttaagg agggtgagat   1398
```

```
aagagaccct tttcctacca gcaaccaaac ttactactag cctgcaatgc aatgaacaca   1458

agtggttgct gagtctcagc cttgctttgt taatgccatg gcaagtagaa aggtatatca   1518

tcaacttcta tacctaagaa tataggattg catttaataa tagtgtttga ggttatatat   1578

gcacaaacac acacagaaat atattcatgt ctatgtgtat atagatcaaa tgttttttttt   1638

ttttggtata tataaccagg tacaccagag gttacatatg tttgagttag actcttaaaa   1698

tcctttgcca aaataaggga tggtcaaata tatgaaacat gtctttagaa aatttaggag   1758

ataaatttat ttttaaattt tgaaacacga aacaattttg aatcttgctc tcttaaagaa   1818

agcatcttgt atattaaaaa tcaaaagatg aggctttctt acatatacat cttagttgat   1878

tatt                                                                1882


<210> SEQ ID NO 37
<211> LENGTH: 370
<212> TYPE: PRT
<213> ORGANISM: Homo sapiens

<400> SEQUENCE: 37

Met His Arg Leu Ile Phe Val Tyr Thr Leu Ile Cys Ala Asn Phe Cys
 1               5                  10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
```

```
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370
```

<210> SEQ ID NO 38
<211> LENGTH: 20
<212> TYPE: DNA
<213> ORGANISM: Artificial Sequence
<220> FEATURE:
<223> OTHER INFORMATION: oligonucleotide primer ZC21,222

<400> SEQUENCE: 38
tgagccctcg ccccagtcag 20

<210> SEQ ID NO 39
<211> LENGTH: 25
<212> TYPE: DNA
<213> ORGANISM: Artificial Sequence
<220> FEATURE:
<223> OTHER INFORMATION: oligonucleotide primer ZC21,224

<400> SEQUENCE: 39
acatacagga aagccttgcc caaaa 25

<210> SEQ ID NO 40
<211> LENGTH: 25
<212> TYPE: DNA
<213> ORGANISM: Artificial Sequence
<220> FEATURE:
<223> OTHER INFORMATION: oligonucleotide primer ZC21,223

<400> SEQUENCE: 40
aaactaccct gcgattctct gctgc 25

<210> SEQ ID NO 41
<211> LENGTH: 21
<212> TYPE: DNA
<213> ORGANISM: Artificial Sequence
<220> FEATURE:
<223> OTHER INFORMATION: oligonucleotide primer ZC21,334

<400> SEQUENCE: 41
ggtaaatgga gcttggctga g 21

<210> SEQ ID NO 42
<211> LENGTH: 3571
<212> TYPE: DNA
<213> ORGANISM: Mus musculus
<220> FEATURE:
<221> NAME/KEY: CDS
<222> LOCATION: (1049)...(2086)

<400> SEQUENCE: 42

-continued

```
gaattcccgg gtcgacccac gcgtccgggc gcccagggga aaggaagctg ggggccgcct      60

ggcggcattc ctcgccgcag tgtgggctcc gtctgccgcg gggcccgcag tgccccctgt     120

ctgcgccagc acctgttggc ccgccagctg gccgcccgcg ccccccgcgc cccccgcgcc     180

cgcccggccg ccagccccgc gccccgcgcg ccgcccgctg gggaaagtg gagacgggga      240

ggggacaaga gcgatcctcc aggccagcca ggccttccct tagccgcccg tgcttagccg     300

ccacctctcc tcagccctgc gtcctgccct gccttagggc aggcatccga gcgctcgcga     360

ctccgagccg cccaagctct cccggcttcc cgcagcactt cgccggtacc cgagggaact     420

tcggtggcca ccgactgcag caaggaggag gctccgcggt ggatccgggc cagtcccgag     480

tcgtccccgc ggcctctctg cccgcccggg acccgcgcgg cactcgcagg gcacggtccc     540

ctccccccag gtgggggtgg ggcgccgcct gccgccccga tcagcagctt tgtcattgat     600

cccaaggtgc tcgcctcgct gccgacctgg cttccagtct ggcttggcgg gaccccgagt     660

cctcgcctgt gtcctgtccc ccaaactgac aggtgctccc tgcgagtcgc cacgactcat     720

cgccgctccc ccgcgtcccc acccccttctt tcctccctcg cctaccccca cccccgcac     780

ttcggcacag ctcaggattt gtttaaacct tgggaaactg gttcaggtcc aggttttgct     840

ttgatccttt tcaaaaactg gagacacaga agagggctct aggaaaaact tttggatggg     900

attatgtgga aactaccctg cgattctctg ctgccagagc cggccaggcg cttccaccgc     960

agcgcagcct ttccccggct gggctgagcc ttggagtcgt cgcttcccca gtgcccgccg    1020

cgagtgagcc ctcgccccag tcagccaa atg ctc ctc ctc ggc ctc ctc ctg      1072
                               Met Leu Leu Leu Gly Leu Leu Leu
                                 1               5

ctg aca tct gcc ctg gcc ggc caa aga acg ggg act cgg gct gag tcc     1120
Leu Thr Ser Ala Leu Ala Gly Gln Arg Thr Gly Thr Arg Ala Glu Ser
     10                  15                  20

aac ctg agc agc aag ttg cag ctc tcc agc gac aag gaa cag aac gga     1168
Asn Leu Ser Ser Lys Leu Gln Leu Ser Ser Asp Lys Glu Gln Asn Gly
 25                  30                  35                  40

gtg caa gat ccc cgg cat gag aga gtt gtc act ata tct ggt aat ggg     1216
Val Gln Asp Pro Arg His Glu Arg Val Val Thr Ile Ser Gly Asn Gly
                 45                  50                  55

agc atc cac agc ccg aag ttt cct cat aca tac cca aga aat atg gtg     1264
Ser Ile His Ser Pro Lys Phe Pro His Thr Tyr Pro Arg Asn Met Val
             60                  65                  70

ctg gtg tgg aga tta gtt gca gta gat gaa aat gtg cgg atc cag ctg     1312
Leu Val Trp Arg Leu Val Ala Val Asp Glu Asn Val Arg Ile Gln Leu
         75                  80                  85

aca ttt gat gag aga ttt ggg ctg gaa gat cca gaa gac gat ata tgc     1360
Thr Phe Asp Glu Arg Phe Gly Leu Glu Asp Pro Glu Asp Asp Ile Cys
     90                  95                 100

aag tat gat ttt gta gaa gtt gag gag ccc agt gat gga agt gtt tta     1408
Lys Tyr Asp Phe Val Glu Val Glu Glu Pro Ser Asp Gly Ser Val Leu
105                 110                 115                 120

gga cgc tgg tgt ggt tct ggg act gtg cca gga aag cag act tct aaa     1456
Gly Arg Trp Cys Gly Ser Gly Thr Val Pro Gly Lys Gln Thr Ser Lys
                125                 130                 135

gga aat cat atc agg ata aga ttt gta tct gat gag tat ttt cca tct     1504
Gly Asn His Ile Arg Ile Arg Phe Val Ser Asp Glu Tyr Phe Pro Ser
            140                 145                 150

gaa ccc gga ttc tgc atc cac tac agt att atc atg cca caa gtc aca     1552
Glu Pro Gly Phe Cys Ile His Tyr Ser Ile Ile Met Pro Gln Val Thr
        155                 160                 165

gaa acc acg agt cct tcg gtg ttg ccc cct tca tct ttg tca ttg gac     1600
```

-continued

```
Glu Thr Thr Ser Pro Ser Val Leu Pro Pro Ser Ser Leu Ser Leu Asp
    170                 175                 180

ctg ctc aac aat gct gtg act gcc ttc agt acc ttg gaa gag ctg att     1648
Leu Leu Asn Asn Ala Val Thr Ala Phe Ser Thr Leu Glu Glu Leu Ile
185                 190                 195                 200

cgg tac cta gag cca gat cga tgg cag gtg gac ttg gac agc ctc tac     1696
Arg Tyr Leu Glu Pro Asp Arg Trp Gln Val Asp Leu Asp Ser Leu Tyr
                205                 210                 215

aag cca aca tgg cag ctt ttg ggc aag gct ttc ctg tat ggg aaa aaa     1744
Lys Pro Thr Trp Gln Leu Leu Gly Lys Ala Phe Leu Tyr Gly Lys Lys
            220                 225                 230

agc aaa gtg gtg aat ctg aat ctc ctc aag gaa gag gta aaa ctc tac     1792
Ser Lys Val Val Asn Leu Asn Leu Leu Lys Glu Glu Val Lys Leu Tyr
        235                 240                 245

agc tgc aca ccc cgg aac ttc tca gtg tcc ata cgg gaa gag cta aag     1840
Ser Cys Thr Pro Arg Asn Phe Ser Val Ser Ile Arg Glu Glu Leu Lys
    250                 255                 260

agg aca gat acc ata ttc tgg cca ggt tgt ctc ctg gtc aag cgc tgt     1888
Arg Thr Asp Thr Ile Phe Trp Pro Gly Cys Leu Leu Val Lys Arg Cys
265                 270                 275                 280

gga gga aat tgt gcc tgt tgt ctc cat aat tgc aat gaa tgt cag tgt     1936
Gly Gly Asn Cys Ala Cys Cys Leu His Asn Cys Asn Glu Cys Gln Cys
                285                 290                 295

gtc cca cgt aaa gtt aca aaa aag tac cat gag gtc ctt cag ttg aga     1984
Val Pro Arg Lys Val Thr Lys Lys Tyr His Glu Val Leu Gln Leu Arg
            300                 305                 310

cca aaa act gga gtc aag gga ttg cat aag tca ctc act gat gtg gct     2032
Pro Lys Thr Gly Val Lys Gly Leu His Lys Ser Leu Thr Asp Val Ala
        315                 320                 325

ctg gaa cac cac gag gaa tgt gac tgt gtg tgt aga gga aac gca gga     2080
Leu Glu His His Glu Glu Cys Asp Cys Val Cys Arg Gly Asn Ala Gly
    330                 335                 340

ggg taa ctgcagcctt cgtagcagca cacgtgagca ctggcattct gtgtaccccc      2136
Gly
345

acaagcaacc ttcatcccca ccagcgttgg ccgcagggct ctcagctgct gatgctggct   2196

atggtaaaga tcttactcgt ctccaaccaa attctcagtt gtttgcttca atagccttcc   2256

cctgcaggac ttcaagtgtc ttctaaaaga ccagaggcac caagaggagt caatcacaaa   2316

gcactgcctt ctagaggaag cccagacaat ggtcttctga ccacagaaac aaatgaaatg   2376

aatgtagatc gctagcaaac tctggagtga cagcatttct tttccactga cagaatggtg   2436

tagcttagtt gtcttgatat gggcaagtga tgtcagcaca agaaaatggt gaaaaacaca   2496

cacttgattg tgaacaatgc agaaatactt ggatttctcc aacctgtttg catagataga   2556

cagatgctct gttttctaca aactcaaagc ttttagagag cagctatgtt aataggaatt   2616

aaatgtgcca tgctgaaagg aaagactgaa gttttcaatg cttggcaact tctccgcaat   2676

ttggaggaaa ggtgcggtca tggtttggag aaagcacacc tgcacagagg agtggccttc   2736

ccttcccttc cctctgaggt ggcttctgtg tttcattgtg tatattttta tattctcctt   2796

ttgacattat aactgttggc ttttctaatc ttgttaaata tttctatttt taccaaaggt   2856

atttaatatt ctttttatg acaacctaga gcaattattt ttagcttgat aatttttttt    2916

tctaaacaaa attgttatag ccagaagaac aaagatgatt gatataaaaa tcttgttgct   2976

ctgacaaaaa catatgtatt tcttccttgt atggtgctag agcttagcgt catctgcatt   3036

tgaaaagatg gaatggggaa gtttttagaa ttggtaggtc gcagggacag tttgataaca   3096
```

-continued

```
actgtactat catcaattcc caattctgtt cttagagcta cgaacagaac agagcttgag   3156

taaatatgga gccattgcta acctacccct ttctatggga aataggagta tagctcagag   3216

aagcacgtcc ccagaaacct cgaccatttc taggcacagt gttctgggct atgctgcgct   3276

gtatggacat atcctattta tttcaatact agggttttat tacctttaaa ctctgctcca   3336

tacacttgta ttaatacatg gatattttta tgtacagaag tatatcattt aaggagttca   3396

cttattatac tctttggcaa ttgcaaagaa aatcaacata atacattgct tgtaaatgct   3456

taatctgtgc ccaagttttg tggtgactat ttgaattaaa atgtattgaa tcatcaaata   3516

aaataatctg gctattttgg ggaaaaaaaa aaaaaaaaaa aaaaagggcg gccgc        3571


<210> SEQ ID NO 43
<211> LENGTH: 345
<212> TYPE: PRT
<213> ORGANISM: Mus musculus

<400> SEQUENCE: 43

Met Leu Leu Leu Gly Leu Leu Leu Leu Thr Ser Ala Leu Ala Gly Gln
 1               5                  10                  15

Arg Thr Gly Thr Arg Ala Glu Ser Asn Leu Ser Ser Lys Leu Gln Leu
            20                  25                  30

Ser Ser Asp Lys Glu Gln Asn Gly Val Gln Asp Pro Arg His Glu Arg
        35                  40                  45

Val Val Thr Ile Ser Gly Asn Gly Ser Ile His Ser Pro Lys Phe Pro
    50                  55                  60

His Thr Tyr Pro Arg Asn Met Val Leu Val Trp Arg Leu Val Ala Val
65                  70                  75                  80

Asp Glu Asn Val Arg Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
        115                 120                 125

Val Pro Gly Lys Gln Thr Ser Lys Gly Asn His Ile Arg Ile Arg Phe
    130                 135                 140

Val Ser Asp Glu Tyr Phe Pro Ser Glu Pro Gly Phe Cys Ile His Tyr
145                 150                 155                 160

Ser Ile Ile Met Pro Gln Val Thr Glu Thr Thr Ser Pro Ser Val Leu
                165                 170                 175

Pro Pro Ser Ser Leu Ser Leu Asp Leu Leu Asn Asn Ala Val Thr Ala
            180                 185                 190

Phe Ser Thr Leu Glu Glu Leu Ile Arg Tyr Leu Glu Pro Asp Arg Trp
        195                 200                 205

Gln Val Asp Leu Asp Ser Leu Tyr Lys Pro Thr Trp Gln Leu Leu Gly
    210                 215                 220

Lys Ala Phe Leu Tyr Gly Lys Lys Ser Lys Val Val Asn Leu Asn Leu
225                 230                 235                 240

Leu Lys Glu Glu Val Lys Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Arg Lys Val Thr Lys Lys
```

-continued

```
    290                 295                 300

Tyr His Glu Val Leu Gln Leu Arg Pro Lys Thr Gly Val Lys Gly Leu
305                 310                 315                 320

His Lys Ser Leu Thr Asp Val Ala Leu Glu His His Glu Glu Cys Asp
                325                 330                 335

Cys Val Cys Arg Gly Asn Ala Gly Gly
            340                 345
```

<210> SEQ ID NO 44
<211> LENGTH: 65
<212> TYPE: DNA
<213> ORGANISM: Artificial Sequence
<220> FEATURE:
<223> OTHER INFORMATION: oligonucleotide primer ZC20,572

<400> SEQUENCE: 44
tcaccacgcg aattcggtac cgctggttcc gcgtggatcc ggccagagac aggggactca 60
ggcgg 65

<210> SEQ ID NO 45
<211> LENGTH: 65
<212> TYPE: DNA
<213> ORGANISM: Artificial Sequence
<220> FEATURE:
<223> OTHER INFORMATION: oligonucleotide primer ZC20,573

<400> SEQUENCE: 45
tctgtatcag gctgaaaatc ttatctcatc cgccaaaaca ctatcctcct gtgctccctc 60
tgcac 65

<210> SEQ ID NO 46
<211> LENGTH: 40
<212> TYPE: DNA
<213> ORGANISM: Artificial Sequence
<220> FEATURE:
<223> OTHER INFORMATION: oligonucleotide primer ZC19,372

<400> SEQUENCE: 46
tgtcgatgaa gccctgaaag acgcgcagac taattcgagc 40

<210> SEQ ID NO 47
<211> LENGTH: 60
<212> TYPE: DNA
<213> ORGANISM: Artificial Sequence
<220> FEATURE:
<223> OTHER INFORMATION: oligonucleotide primer ZC19,351

<400> SEQUENCE: 47
acgcgcagac taattcgagc tcccaccatc accatcacca cgcgaattcg gtaccgctgg 60

<210> SEQ ID NO 48
<211> LENGTH: 60
<212> TYPE: DNA
<213> ORGANISM: Artificial Sequence
<220> FEATURE:
<223> OTHER INFORMATION: oligonucleotide primer ZC19,352

<400> SEQUENCE: 48
actcactata gggcgaattg cccgggggat ccacgcggaa ccagcggtac cgaattcgcg 60

<210> SEQ ID NO 49
<211> LENGTH: 42
<212> TYPE: DNA

-continued

```
<213> ORGANISM: Artificial Sequence
<220> FEATURE:
<223> OTHER INFORMATION: oligonucleotide primer ZC19,371

<400> SEQUENCE: 49

acggccagtg aattgtaata cgactcacta tagggcgaat tg                    42


<210> SEQ ID NO 50
<211> LENGTH: 1095
<212> TYPE: DNA
<213> ORGANISM: Artificial Sequence
<220> FEATURE:
<223> OTHER INFORMATION: Fused DNA

<400> SEQUENCE: 50

ctgaaagacg cgcagactaa ttcgagctcc caccatcacc atcaccacgc gaattcggta     60

ccgctggttc cgcgtggatc cggccagaga caggggactc aggcggaatc caacctgagt    120

agtaaattcc agttttccag caacaaggaa cagaacggag tacaagatcc tcagcatgag    180

agaattatta ctgtgtctac taatggaagt attcacagcc caaggtttcc tcatacttat    240

ccaagaaata cggtcttggt atggagatta gtagcagtag aggaaaatgt atggatacaa    300

cttacgtttg atgaaagatt tgggcttgaa gacccagaag atgacatatg caagtatgat    360

tttgtagaag ttgaggaacc cagtgatgga actatattag ggcgctggtg tggttctggt    420

actgtaccag gaaaacagat ttctaaagga aatcaaatta ggataagatt tgtatctgat    480

gaatattttc cttctgaacc agggttctgc atccactaca acattgtcat gccacaattc    540

acagaagctg tgagtccttc agtgctaccc ccttcagctt tgccactgga cctgcttaat    600

aatgctataa ctgcctttag taccttggaa gaccttattc gatatcttga accagagaga    660

tggcagttgg acttagaaga tctatatagg ccaacttggc aacttcttgg caaggctttt    720

gtttttggaa gaaaatccag agtggtggat ctgaaccttc taacagagga ggtaagatta    780

tacagctgca cacctcgtaa cttctcagtg tccataaggg aagaactaaa gagaaccgat    840

accattttct ggccaggttg tctcctggtt aaacgctgtg gtgggaactg tgcctgttgt    900

ctccacaatt gcaatgaatg tcaatgtgtc ccaagcaaag ttactaaaaa ataccacgag    960

gtccttcagt tgagaccaaa gaccggtgtc aggggattgc acaaatcact caccgacgtg   1020

gccctggagc accatgagga gtgtgactgt gtgtgcagag ggagcacagg aggatagtgt   1080

tttggcggat gagat                                                    1095
```